US008802626B2

(12) United States Patent
Rueger et al.

(10) Patent No.: US 8,802,626 B2
(45) Date of Patent: *Aug. 12, 2014

(54) OSTEOGENIC DEVICES AND METHODS OF USE THEREOF FOR REPAIR OF ENDOCHONDRAL BONE, OSTEOCHONDRAL AND CHONDRAL DEFECTS

(75) Inventors: David C. Rueger, Southborough, MA (US); Marjorie M. Tucker, Holliston, MA (US); An-Cheng Chang, Westborough, MA (US)

(73) Assignee: Stryker Corporation, Kalamazoo, MI (US)

( * ) Notice: Subject to any disclaimer, the term of this patent is extended or adjusted under 35 U.S.C. 154(b) by 496 days.

This patent is subject to a terminal disclaimer.

(21) Appl. No.: 13/051,928

(22) Filed: Mar. 18, 2011

(65) Prior Publication Data
US 2013/0149294 A1 Jun. 13, 2013

Related U.S. Application Data

(63) Continuation of application No. 09/045,331, filed on Mar. 20, 1998, now abandoned, which is a continuation-in-part of application No. 08/822,186, filed on Mar. 20, 1997, now Pat. No. 7,041,641.

(51) Int. Cl.
| | |
|---|---|
| A61K 38/18 | (2006.01) |
| A61K 38/39 | (2006.01) |
| A61K 47/02 | (2006.01) |
| A61K 47/38 | (2006.01) |
| C07K 14/51 | (2006.01) |

(52) U.S. Cl.
USPC .......... 514/8.8; 514/16.7; 514/17.1; 514/801; 514/944; 424/426; 424/486; 530/350; 530/356

(58) Field of Classification Search
None
See application file for complete search history.

(56) References Cited

U.S. PATENT DOCUMENTS

| | | | |
|---|---|---|---|
| 4,153,739 A | 5/1979 | Kessler | |
| 4,353,982 A | 10/1982 | Gomez et al. | |
| 4,814,120 A | 3/1989 | Huc et al. | |
| 4,968,590 A | 11/1990 | Kuberasampath et al. | |
| 4,975,526 A | 12/1990 | Kuberasampath et al. | |
| 5,011,691 A | 4/1991 | Oppermann et al. | |
| 5,013,649 A | 5/1991 | Wang et al. | |
| 5,073,373 A | 12/1991 | O'Leary et al. | |
| 5,171,574 A | 12/1992 | Kuberasampath et al. | |
| 5,266,683 A | 11/1993 | Oppermann et al. | |
| 5,281,265 A | 1/1994 | Liu | |
| 5,284,756 A | 2/1994 | Grinna et al. | |
| 5,354,557 A | 10/1994 | Oppermann et al. | |
| 5,366,964 A | 11/1994 | Lindstrom et al. | |
| 5,385,887 A | 1/1995 | Yim et al. | |
| 5,422,340 A | 6/1995 | Ammann et al. | |
| 5,457,093 A | 10/1995 | Cini et al. | |
| 5,468,845 A | 11/1995 | Oppermann et al. | |
| 5,520,923 A | 5/1996 | Tjia et al. | |
| 5,597,897 A | 1/1997 | Ron et al. | |
| 5,641,649 A | 6/1997 | Stanchi et al. | |
| 5,645,591 A | 7/1997 | Kuberasampath et al. | |
| 5,674,292 A | 10/1997 | Tucker et al. | |
| 5,674,844 A | 10/1997 | Kuberasampath et al. | |
| 5,717,006 A | 2/1998 | Daculsi et al. | |
| 5,853,746 A | 12/1998 | Hunziker | |
| 6,013,856 A | 1/2000 | Tucker et al. | |
| 6,232,458 B1 | 5/2001 | Weiss et al. | |
| 6,461,630 B1 * | 10/2002 | Tucker et al. | 424/423 |
| 6,468,308 B1 | 10/2002 | Kuberasampath et al. | |
| 6,504,079 B2 | 1/2003 | Tucker et al. | |
| 6,949,251 B2 | 9/2005 | Dalal et al. | |
| 7,041,641 B2 | 5/2006 | Rueger et al. | |
| 7,410,947 B2 | 8/2008 | Rueger et al. | |
| 8,354,376 B2 * | 1/2013 | Rueger et al. | 514/8.8 |
| 8,372,805 B1 * | 2/2013 | Rueger et al. | 514/8.8 |

FOREIGN PATENT DOCUMENTS

| | | |
|---|---|---|
| EP | 0 723 013 | 7/1996 |
| JP | 63-181770 | 7/1988 |
| JP | 3-011006 | 1/1991 |
| JP | 07-246235 | 9/1995 |
| JP | 8-508922 | 9/1996 |
| JP | 9-502368 | 3/1997 |
| WO | WO 88/00205 | 1/1988 |
| WO | WO 89/09787 | 10/1989 |
| WO | WO 90/11366 | 10/1990 |
| WO | WO 91/18098 | 11/1991 |
| WO | WO 91/18558 | 12/1991 |

(Continued)

OTHER PUBLICATIONS

Alberts et al., "Molecular Biology of the Cell," (Garland Publishing, Inc., New York), pp. 692-693, 705 (1983).
Arnaud et al., "Potentiation of transforming growth factor (TGF.beta. 1) by natural coral and fibrin in a rabbit cranioplasty model," *Calcif Tissue Int.*, 54:493-498 (1994).
Aydelotte et al., "Differences between sub-populations of cultured bovine articular chondrocytes. I. Morphology and cartilage matrix production," *Conn. Tiss. Res.*, 18:205-222 (1988).

(Continued)

*Primary Examiner* — David Romeo
(74) *Attorney, Agent, or Firm* — Ropes & Gray LLP; James F. Haley, Jr.; Karen Mangasarian

(57) ABSTRACT

Disclosed herein are improved osteogenic devices and methods of use thereof for repair of bone and cartilage defects. The devices and methods promote accelerated formation of repair tissue with enhanced stability using less osteogenic protein than devices in the art. Defects susceptible to repair with the instant invention include, but are not limited to: critical size defects, non-critical size defects, non-union fractures, fractures, osteochondral defects, subchondral defects, and detects resulting from degenerative diseases such as osteochondritis dessicans.

26 Claims, 2 Drawing Sheets

(56) References Cited

FOREIGN PATENT DOCUMENTS

| WO | WO 92/00382 | 1/1992 |
|---|---|---|
| WO | WO 93/00432 | 1/1993 |
| WO | WO 93/16099 | 8/1993 |
| WO | WO 94/10203 | 5/1994 |
| WO | WO 94/15653 | 7/1994 |
| WO | WO 94/15949 | 7/1994 |
| WO | WO 94/15965 | 7/1994 |
| WO | WO 94/15966 | 7/1994 |
| WO | WO 94/20133 | 9/1994 |
| WO | WO 94/21681 | 9/1994 |
| WO | WO 94/26892 | 11/1994 |
| WO | WO 94/26893 | 11/1994 |
| WO | WO 95/01802 | 1/1995 |
| WO | WO 95/07108 | 3/1995 |
| WO | WO 95/10539 | 4/1995 |
| WO | WO 95/16035 | 6/1995 |
| WO | WO 95/24210 | 9/1995 |
| WO | WO 95/25546 | 9/1995 |
| WO | WO 95/33830 | 12/1995 |
| WO | WO 96/01316 | 1/1996 |
| WO | WO 96/01845 | 1/1996 |
| WO | WO 96/09078 | 3/1996 |
| WO | WO 96/14335 | 5/1996 |
| WO | WO 96/36710 | 11/1996 |
| WO | WO 96/39169 | 12/1996 |
| WO | WO 96/39170 | 12/1996 |
| WO | WO 96/40297 | 12/1996 |

OTHER PUBLICATIONS

Basler et al., "Control of cell pattern in the neural tube: regulation of cell differentiation by dorsalin-1, a novel TGFβ family member," *Cell*, 73:687-702 (1993).
Beck et al., "TGF-.beta.1 Induces Bone Closure of Skull Defects," *Journal of Bone and Mineral Research*, 6:1257-1265 (1991).
Beck et al., "The Single Application of TGF-.beta.1 Induces Closure of Skull Defects," *Journal of Bone and Mineral Research*, 6(suppl 1):155 (1991).
Bowie et aL, "Deciphering the Message in Protein Sequences: Tolerance to Amino Acid Substitutions", *Science*, 247:1306-1310 (1990).
Bulletin VC-543C, "Rheology of Aqualon.RTM. Water-Soluble Polymers in Solution," Hercules Incorporated, Aqualon Division, Hercules Plaza, 1313 North Market Street, Wilingtohn, DE 19897-0001, 2001.
Cao et al., "Water Vapour-Treated Hydroxyapatite Coatings After Plasma Spraying and Their Characteristics," *Biomaterials*, 17:419-424 (1996).
Carroll, "Patient Status and Contrast Agents" in Fuchs's Radiographic Exposure, Processing and Quality Control, 5th ed. (Charles C. Thomas Publisher, Illinois), pp. 151-154 (1993).
Celeste et al., "Identification of transforming growth factor beta family members present in bone-inductive protein purified from bovine bone," *Proc. Natl. Acad. Sci.*, 87:9843-9847 (1990).
Cook et al., "Recombinant Human Bone Morphogenetic Protein-7 Induces Healing in a Canine Long-Bone Segmental Defect Model," *Clinical Orthopaedics and Related Research*, 301:302-312 (1994).
Cook et al., "In vivo evaluation of recombinant human osteogenic protein (rhOP-1) implants as a bone graft substitute for spinal fusions," *Spine*, Phila Pa 1976), 19:1655-1663 (1994).
Cook et al., "The Effect of Recombinant Human Osteogenic Protein-1 on Healing of Large Segmental Bone Defects," *The Journal of Bone and Joint Surgery*, 76-A:827-838 (1994).
Cook et al., "Effect of recombinant human osteogenic protein-1 on healing of segmental defects in non-human primates," J Bone Joint Surg Am., 77:734-750 (1995).
Dayhoff et al., "A Model of Evolutionary Change in Proteins," Chapter 22 Atlas of Protein Sequence and Structure, 5(suppl. 3):345-352 (1978).
Doll et al., "The Osteogenic Potential of Two Composite Graft Systems Using Osteogenin," *Journal of Periodontology*, 61:745-750 (1990).

Ehrlich et al., "Contrast Media and Special Imaging Techniques" in *Patient Care in Radiography*, 4th ed. (Mosby, St. Louis), pp. 211-254 (1993).
FMC Corp., Technical Bulletin RC-16, pp. 1-8 (1986).
Handbook of Pharmaceutical Excipients, 2nd ed., A Wade and P.J. Weller (eds), American Pharmaceutical Association, Washington, DC, Jan. 1994, p. xiii.
Hogan, "Bone morphogenetic proteins: Multifunctional regulators of vertebrate development," *Genes & Development*, 10:1580-1594 (1996).
Hollinger et al., "Poly(alpha-hydroxy acids): carriers for bone morphogenetic proteins," *Biomaterials*, 17:187-194 (1996).
Johnson et al., "Porous Ceramics as Bone Graft Substitutes in Long Bone Defects: A Biomechanical, Histological, and Radiographic Analysis," *Journal of Orthopaedic Research*, 14:351-369 (1996).
Kenley et al., "Osseous Regeneration in the Rat Calvarium Using Novel Delivery Systems for Recombinant Human Bone Morphogenetic Protein-2 (rhBMP-2)," *Journal of Biomedical Materials Research*, 28:1139-1147 (1994).
Lee et al., "Demineralized bone matrix and spinal arthrodesis," *Spine Journal*, 5 (6 Suppl.): 217S-223S (2005).
Lee, "Expression of growth/differentiation factor 1 in the nervous system: conservation of a bicistronic structure," *Proc. Natl. Acad. Sci.*, 88:4250-4254 (1991).
LeGeros et al., "In Vivo Transformation of Biphasic Calcium Phosphate Ceramics: Ultrastructural and Physicochemical Characterizations," in CRC Handbook of Bioactive Ceramics (CRC Press), vol. II, pp. 17-28 (1990).
LeGeros, "Calcium Phosphate Materials in Restorative Dentistry: A Review," *Advances in Dental Research*, 2:164-180 (1988).
Lyons et al., "Vgr-1, a mammalian gene related to Xenopus Vg-1, is a member of the transforming growth factor beta gene superfamily," *Proc. Natl. Acad. Sci.*, 86:4554-4558 (1989).
Maddox et al., "Optimizing Human Demineralized Bone Matrix for Clinical Application," *Tissue Engineering*, 6:441-448 (2000).
Massague, "The transforming growth factor-beta family," *Annu. Rev. Cell Biol.*, 6:597-641 (1990).
Muschler et al., "Evaluation of human bone morphogenetic protein 2 in a canine spinal fusion model," *Clin Orthop Relat Res.*, 308:229-240 (1994).
Needleman et al., "A general method applicable to the search for similarities in the amino acid sequence of two proteins," *J. Mol. Biol.*, 48:443-453 (1970).
Ngo et al., in The Protein Folding Problem and Tertiary Structure Prediction, Merz and Le Grand (Eds), Aug. 1994, Springer Verlag, pp. 433 and 492-495.
Ogawa et al., "Bovine Bone Activin Enhances Bone Morphogenetic Protein-induced Ectopic Bone Formation", *J. Biol. Chem.*, 267:14233-14237 (1992).
Özkaynak et al., "OP-1 cDNA encodes an osteogenic protein in the TGF-beta family," *EMBO J.*, 9:2085-2093 (1990).
Özkaynak et al., "Osteogenic protein-2—a new member of the transforming growth factor-β superfamily expressed early in embryogenesis," *J. Biol. Chem.*, 267:25220-25227 (1992).
Padgett et al., "A transcript from a drosophila pattern gene predicts a protein homologous to the transforming growth factor-beta family," *Nature*, 325:81-84 (1987).
Piatelli et al., "Clinical and Histologic Aspects of Biphasic Calcium Phosphate Ceramic (BCP) Used in Connection With Implant Placement," *Biomaterials*, 17(18):1767-1770 (1996).
Poole et al., "Morphological and functional interrelationships of articular cartilage matrices," *J. Anat.*, 138:113-138 (1984).
Reddi, "Symbiosis of Biotechnology and Biomaterials: Applications in Tissue Engineering of Bone and Cartilage," *Journal of Cellular Biochemistry*, 56(2):192-195 (1994).
Rutherford et al., "A New Biological Approach to Vital Pulp Therapy", *Crit. Rev. Oral Biol. Med.*, 6:218-229 (1995).
Sampath et al., "Homology of Bone-inductive Proteins from Human, Monkey, Bovine, and Rat Extracellular Matrix," *Proc. Natl. Acad. Sci. USA*, 80:6591-6595 (1983).
Sampath et al., "Bovine osteogenic protein is composed of dimers of OP-1 and BMP-2A, two members of the transforming growth factor-β superfamily," *J. Biol. Chem.*, 265:13198-13205 (1990).

(56) References Cited

OTHER PUBLICATIONS

Sato et al., "Bone Morphogenesis of Rabbit Bone Morphogenetic Protein-bound Hydroxyapatite-fibrin Composite." *Clin. Orthop. and Related Research*, 263:254-262 (1991).

Schmitz et al., "The Critical Size Defect as an Experimental Model for Craniomandibulofacial Nonunions," *Clin. Orthop. and Related Research*, 205:299-308 (1986).

Shapiro, "Cell Origin and Differentiation in the Repair of Full-Thickness Defects of Articular Cartilage," *The Journal of Bone and Joint Surgery* 75-A:532-553 (1993).

Sierra, "Fibrin Sealant Adhesive Systems: A Review of Their Chemistry, Material Properties and Clinical Applications," *J. Biomaterials and Applications*, 7:309-352 (1993).

Snopek, "Contrast Media" in Fundamentals of Special Radiographic Procedures, 3rd ed. (Harcourt, Pennsylvania), pp. 66-76 (1992).

Storm et al., "Limb alterations in brachypodism mice due to mutations in a new member of the TGFβ-superfamily," *Nature*, 368:639-643 (1994).

Takao et al., "Identification of rat bone morphogenetic protein-3b (BMP-3b), a new member of BMP-3," *Biochem. Biophys. Res. Comm.*, 219:656-662 (1996).

Turco, "Intravenous Admixtures," Chapter 95, in Remington's Pharmaceutical Sciences, 18th Ed. (Mack Pub. Co., Easton, PA), pp. 1570 (1990).

Von Heijne, "A new method for predicting signal sequence cleavage sites," *Nucleic Acids Research*, 14:4683-4691 (1986).

Vukicevic et al., "Extracellular Matrix and Bone Morphogenetic Proteins in Cartilage and Bone Development and Repair," *Advances in Molecular and Cell Biology*, 6:207-224 (1993).

Weeks et al., "A maternal mRNA localized to the vegetal hemisphere in Xenopus eggs codes for a growth factor related to TGF-beta," *Cell*, 51:861-867 (1987).

Wharton et al., "Drosophila 60A gene, another transforming growth factor β family member, is closely related to human bone morphogenetic proteins," *Proc. Natl. Acad. Sci.*, 88:9214-9218 (1991).

Wozney et al., "Novel regulators of bone formation: molecular clones and activities," *Science*, 242:1528-1534 (1988).

Zanetti et al., "Two subpopulations of differentiated chondrocytes identified with a monoclonal antibody to keratan sulfate," *J. Cell Biol.*, 101:53-59 (1985).

Aqualon® Sodium Carboxymethylcellulose, Physical and Chemical Properties, Bulletin 250-10H Rev. 4-02, 30pages, date unknown.

Celleosize Hydroxyethyl Cellulose, Form No. 325-000001-0805 AMS, 28 pages, Aug. 2005.

Inoue et al., "The combined use of composite ceramic granules and fibrin glue for cranioplasties: Results of a rat model study and clinical findings with regard to biocompatibility," Japan J. Neurosurg., 4(6):543-547 (1995) (with English translation).

\* cited by examiner

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1822 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: HOMO SAPIENS
      (F) TISSUE TYPE: HIPPOCAMPUS (ix) FEATURE:
      (A) NAME/KEY: CDS
      (B) LOCATION: 49..1341
      (C) IDENTIFICATION METHOD: experimental
      (D) OTHER INFORMATION: /function= "OSTEOGENIC PROTEIN"
         /product= "OP1"
         /evidence= EXPERIMENTAL
         /standard_name= "OP1"

(xi) SEQUENCE DESCRIPTION: SEQ ID NO:1:

```
GGTGCGGGCC CGGAGCCCGG AGCCCGGGTA GCGCGTAGAG CCGGCGCG ATG CAC GTG        57
                                                    Met His Val
                                                      1

CGC TCA CTG CGA GCT GCG GCG CCG CAC AGC TTC GTG GCG CTC TGG GCA       105
Arg Ser Leu Arg Ala Ala Ala Pro His Ser Phe Val Ala Leu Trp Ala
      5              10                  15

CCC CTG TTC CTG CTG CGC TCC GCC CTG GCC GAC TTC AGC CTG GAC AAC       153
Pro Leu Phe Leu Leu Arg Ser Ala Leu Ala Asp Phe Ser Leu Asp Asn
 20              25                  30                  35

GAG GTG CAC TCG AGC TTC ATC CAC CGG CGC CTC CGC AGC CAG GAG CGG       201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC       249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG       297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC       345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC       393
Gly Gln Gly Phe Ser Tyr Pro Tyr Lys Ala Val Phe Ser Thr Gln Gly
```

```
             100                 105                 110                 115
CCC CCT CTG GCC AGC CTG CAA GAT AGC CAT TTC CTC ACC GAC GCC GAC        441
Pro Pro Leu Ala Ser Leu Gln Asp Ser His Phe Leu Thr Asp Ala Asp
            120                 125                 130

ATG GTC ATG AGC TTC GTC AAC CTC GTG GAA CAT GAC AAG GAA TTC TTC        489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC        537
His Pro Arg Tyr His His Arg Glu Phe Arg Phe Asp Leu Ser Lys Ile
            150                 155                 160

CCA GAA GGG GAA GCT GTC ACG GCA GCC GAA TTC CGG ATC TAC AAG GAC        585
Pro Glu Gly Glu Ala Val Thr Ala Ala Glu Phe Arg Ile Tyr Lys Asp
            165                 170                 175

TAC ATC CGG GAA CGC TTC GAC AAT GAG ACG TTC CGG ATC AGC GTT TAT        633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC        681
Gln Val Leu Gln Glu His Leu Gly Arg Glu Ser Asp Leu Phe Leu Leu
            200                 205                 210

GAC AGC CGT ACC CTC TGG GCC TCG GAG GAG GGC TGG CTG GTG TTT GAC        729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG        777
Ile Thr Ala Thr Ser Asn His Trp Val Val Asn Pro Arg His Asn Leu
            230                 235                 240

GGC CTG CAG CTC TCG GTG GAG ACG CTG GAT GGG CAG AGC ATC AAC CCC        825
Gly Leu Gln Leu Ser Val Glu Thr Leu Asp Gly Gln Ser Ile Asn Pro
            245                 250                 255

AAG TTG GCG GGC CTG ATT GGG CGG CAC GGG CCC CAG AAC AAG CAG CCC        873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC        921
Phe Met Val Ala Phe Phe Lys Ala Thr Glu Val His Phe Arg Ser Ile
            280                 285                 290

CGG TCC ACG GGG AGC AAA CAG CGC AGC CAG AAC CGC TCC AAG ACG CCC        969
Arg Ser Thr Gly Ser Lys Gln Arg Ser Gln Asn Arg Ser Lys Thr Pro
            295                 300                 305

AAG AAC CAG GAA GCC CTG CGG ATG GCC AAC GTG GCA GAG AAC AGC AGC       1017
Lys Asn Gln Glu Ala Leu Arg Met Ala Asn Val Ala Glu Asn Ser Ser
            310                 315                 320

AGC GAC CAG AGG CAG GCC TGT AAG AAG CAC GAG CTG TAT GTC AGC TTC       1065
Ser Asp Gln Arg Gln Ala Cys Lys Lys His Glu Leu Tyr Val Ser Phe
            325                 330                 335

CGA GAC CTG GGC TGG CAG GAC TGG ATC ATC GCG CCT GAA GGC TAC GCC       1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG       1161
Ala Tyr Tyr Cys Glu Gly Glu Cys Ala Phe Pro Leu Asn Ser Tyr Met
            360                 365                 370

AAC GCC ACC AAC CAC GCC ATC GTG CAG ACG CTG GTC CAC TTC ATC AAC       1209
Asn Ala Thr Asn His Ala Ile Val Gln Thr Leu Val His Phe Ile Asn
            375                 380                 385

CCG GAA ACG GTG CCC AAG CCC TGC TGT GCG CCC ACG CAG CTC AAT GCC       1257
Pro Glu Thr Val Pro Lys Pro Cys Cys Ala Pro Thr Gln Leu Asn Ala
            390                 395                 400

ATC TCC GTC CTC TAC TTC GAT GAC AGC TCC AAC GTC ATC CTG AAG AAA       1305
Ile Ser Val Leu Tyr Phe Asp Asp Ser Ser Asn Val Ile Leu Lys Lys
            405                 410                 415

TAC AGA AAC ATG GTG GTC CGG GCC TGT GGC TGC CAC TAGCTCCTCC            1351
```

```
Tyr Arg Asn Met Val Arg Ala Cys Gly Cys His
420             425             430

GAGAATTCAG ACCCTTTGGG GCCAAGTTTT TCTGGATCCT CCATTGCTCG CCTTGGCCAG   1411

GAACCAGCAG ACCAACTGCC TTTTGTGAGA CCTTCCCCTC CCTATCCCCA ACTTTAAAGG   1471

TGTGAGAGTA TTAGGAAACA TGAGCAGCAT ATGGCTTTTG ATCAGTTTTT CAGTGGCAGC   1531

ATCCAATGAA CAAGATCCTA CAAGCTGTGC AGGCAAAACC TAGCAGGAAA AAAAACAAC   1591

GCATAAAGAA AAATGGCCGG GCCAGGTCAT TGGCTGGGAA GTCTCAGCCA TGCACGGACT   1651

CGTTTCCAGA GGTAATTATG AGCGCCTACC AGCCAGGCCA CCCAGCCGTG GGAGGAAGGG   1711

GGCGTGGCAA GGGGTGGGCA CATTGGTGTC TGTGCGAAAG GAAATTGAC CCGGAAGTTC   1771

CTGTAATAAA TGTCACAATA AACGAATGA ATGAAAAAAA AAAAAAAAA A              1822

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255
```

```
Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430
```

(2) INFORMATION FOR SEQ ID NO:3:

(i) SEQUENCE CHARACTERISTICS:
(A) LENGTH: 102 amino acids
(B) TYPE: amino acid
(C) STRANDEDNESS:
(D) TOPOLOGY: linear (ii) MOLECULE TYPE: protein (ix) FEATURE:
(A) NAME/KEY: Protein
(B) LOCATION: 1..102
(D) OTHER INFORMATION: /label= OPX
/note= "wherein each Xaa is independently selected from a group of one or more specified amino acids as defined in the specification."

(xi) SEQUENCE DESCRIPTION: SEQ ID NO:3:

```
Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100
```

(2) INFORMATION FOR SEQ ID NO:4:

(i) SEQUENCE CHARACTERISTICS:

```
          (A) LENGTH: 97 amino acids
          (B) TYPE: amino acid
          (C) STRANDEDNESS:
          (D) TOPOLOGY: linear (ii) MOLECULE TYPE: protein (ix) FEATURE:
          (A) NAME/KEY: Protein
          (B) LOCATION: 1..97
          (D) OTHER INFORMATION: /label= Generic-Seq-7
              /note= "wherein each Xaa is independently selected from a
              group of one or more specified amino acids as defined in
              the specification."

(xi) SEQUENCE DESCRIPTION: SEQ ID NO:4:

Leu Xaa Xaa Xaa Phe Xaa Xaa Xaa Gly Trp Xaa Xaa Xaa Xaa Xaa
 1               5                  10                  15

Pro Xaa Xaa Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Xaa
            35                  40                  45

Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Leu Xaa Xaa Xaa Xaa Xaa Xaa Xaa
 65                  70                  75                  80

Val Xaa Leu Xaa Xaa Xaa Xaa Xaa Met Xaa Val Xaa Xaa Cys Xaa Cys
            85                  90                  95

Xaa (2) INFORMATION FOR SEQ ID NO:5:

(i) SEQUENCE CHARACTERISTICS:
          (A) LENGTH: 102 amino acids
          (B) TYPE: amino acid
          (C) STRANDEDNESS:
          (D) TOPOLOGY: linear (ii) MOLECULE TYPE: protein (ix) FEATURE:
          (A) NAME/KEY: Protein
          (B) LOCATION: 1..102
          (D) OTHER INFORMATION: /label= Generic-Seq-8
              /note= "wherein each Xaa is independently selected from a
              group of one or more specified amino acids as defined in
              the specification."

(xi) SEQUENCE DESCRIPTION: SEQ ID NO:5:

Cys Xaa Xaa Xaa Xaa Leu Xaa Xaa Xaa Phe Xaa Xaa Xaa Gly Trp Xaa
 1               5                  10                  15

Xaa Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
            35                  40                  45

Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
 65                  70                  75                  80

Xaa Xaa Xaa Xaa Xaa Val Xaa Leu Xaa Xaa Xaa Xaa Xaa Met Xaa Val
            85                  90                  95

Xaa Xaa Cys Xaa Cys Xaa
            100
```

(2) INFORMATION FOR SEQ ID NO:6:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= Generic-Seq-9
            /note= "wherein each Xaa is independently selected from a
            group of one or more specified amino acids as defined in
            the specification."

(xi) SEQUENCE DESCRIPTION: SEQ ID NO:6:

```
Xaa Xaa Xaa Xaa Xaa Xaa Xaa Xaa Xaa Xaa Xaa Xaa Xaa Xaa Xaa
  1               5                  10                  15

Pro Xaa Xaa Xaa Xaa Xaa Xaa Xaa Cys Xaa Gly Xaa Cys Xaa Xaa
                 20                  25                  30

Xaa Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Cys Xaa Pro
         50                  55                  60

Xaa Xaa Xaa Xaa Xaa Xaa Xaa Leu Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Cys Xaa Cys
                 85                  90                  95

Xaa
```

(2) INFORMATION FOR SEQ ID NO:7:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= Generic-Seq-10
            /note= "wherein each Xaa is independently selected from a
            group of one or more specified amino acids as defined in
            the specification."

(xi) SEQUENCE DESCRIPTION: SEQ ID NO:7:

```
Cys Xaa Xaa Xaa Xaa Xaa Xaa Xaa Xaa Xaa Xaa Xaa Xaa Xaa Xaa
  1               5                  10                  15

Xaa Xaa Xaa Xaa Xaa Pro Xaa Xaa Xaa Xaa Xaa Xaa Cys Xaa Gly
                 20                  25                  30

Xaa Cys Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa
         50                  55                  60

Xaa Xaa Cys Xaa Pro Xaa Xaa Xaa Xaa Xaa Xaa Xaa Leu Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95
```

```
Xaa Xaa Cys Xaa Cys Xaa
            100

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Protein
        (B) LOCATION: 1..5
        (D) OTHER INFORMATION: /note= "wherein each Xaa is
             independently selected from a group of one or more
             specified amino acids as defined in the specification"

(xi) SEQUENCE DESCRIPTION: SEQ ID NO:8:

Cys Xaa Xaa Xaa Xaa
1               5

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Protein
        (B) LOCATION: 1..5
        (D) OTHER INFORMATION: /note= "wherein each Xaa is
             independently selected from a group of one or more
             specified amino acids as defined in the specification"

(xi) SEQUENCE DESCRIPTION: SEQ ID NO:9:

Cys Xaa Xaa Xaa Xaa
1               5
```

_

OSTEOGENIC DEVICES AND METHODS OF USE THEREOF FOR REPAIR OF ENDOCHONDRAL BONE, OSTEOCHONDRAL AND CHONDRAL DEFECTS

CONTINUING APPLICATION DATA

This application is a continuation application of U.S. application Ser. No. 09/045,331, filed Mar. 20,1998, which is a continuation-in-part of U.S. application Ser. No. 08/822,186, filed Mar. 20,1997, now U.S. Pat. No. 7,041,641, the entire disclosures of each of which are incorporated by reference herein.

FIELD OF THE INVENTION

The invention disclosed herein relates to materials and methods for repairing bone and cartilage defects using osteogenic proteins.

BACKGROUND OF THE INVENTION

A class of proteins now has been identified that is competent to act as true chondrogenic tissue morphogens. That is, these proteins are able, on their own, to induce the proliferation and differentiation of progenitor cells into functional bone, cartilage, tendon, and/or ligamentous tissue. This class of proteins, referred to herein as "osteogenic proteins" or "morphogenic proteins" or "morphogens," includes members of the family of bone morphogenetic proteins (BMPs) which were initially identified by their ability to induce ectopic, endochondral bone morphogenesis. The osteogenic proteins generally are classified in the art as a subgroup of the TGF-β superfamily of growth factors (Hogan (1996) *Genes & Development* 10:1580-1594). Members of the morphogen family of proteins include the mammalian osteogenic protein-1 (OP-1, also known as BMP-7, and the *Drosophila* homolog 60A), osteogenic protein-2 (OP-2, also known as BMP-8), osteogenic protein-3 (OP-3), BMP-2 (also known as BMP-2A or CBMP-2A, and the *Drosophila* homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF3 (also known as Vgr2), GDF8, GDF9, GDF10, GDF11, GDF12, BMP-13, BMP-14, BMP-15, GDF-5 (also known as CDMP-1 or MP52), GDF-6 (also known as CDMP-2), GDF-7 (also known as CDMP-3), the *Xenopus* homolog Vg1 and NODAL, UNIVIN, SCREW, ADMP, and NEURAL. Members of this family encode secreted polypeptide chains sharing common structural features, including processing from a precursor "pro-form" to yield a mature polypeptide chain competent to dimerize and containing a carboxy terminal active domain, of approximately 97-106 amino acids. All members share a conserved pattern of cysteines in this domain and the active form of these proteins can be either a disulfide-bonded homodimer of a single family member or a heterodimer of two different members (see, e.g., Massague (1990) *Annu. Rev. Cell Biol,* 6:597; Sampath, et al. (1990) *J. Biol. Chem.* 265:13198). See also, U.S. Pat. No. 5,011,691; U.S. Pat. No. 5,266,683, Ozkaynak et al. (1990) *EMBO J.* 2: 2085-2093, Wharton et al. (1991) *PNAS* 88:9214-9218), (Ozkaynak (1992) *J. Biol. Chem.*, 267: 25220-25227 and U.S. Pat. No. 5,266,683); (Celeste et al. (1991) *PNAS* 87:9843-9847); (Lyons et al. (1989) *PNAS* 86:4554-4558). These disclosures describe the amino acid and DNA sequences, as well as the chemical and physical characteristics, of these osteogenic proteins. See also, Wozney et al. (1988) *Science* 242:1528-1534); BMP9 (WO93/00432, published Jan. 7, 1993); DPP (Padgett et al. (1987) *Nature* 325:81-84; and Vg-1 (Weeks (1987) *Cell* 51:861-867).

Thus true osteogenic proteins capable of inducing the above-described cascade of morphogenic events resulting in endochondral bone formation, have now been identified, isolated, and cloned. Whether naturally-occurring or synthetically prepared, these osteogenic factors, when implanted in a mammal in association with a matrix or substrate that allows attachment, proliferation and differentiation of migratory progenitor cells, can induce recruitment of accessible progenitor cells and stimulate their proliferation, thereby inducing differentiation into chondrocytes and osteoblasts, and further inducing differentiation of intermediate cartilage, vascularization, bone formation, remodeling, and, finally, marrow differentiation. Furthermore, numerous practitioners have demonstrated the ability of these osteogenic proteins, when admixed with either naturally-sourced matrix materials such as collagen or synthetically-prepared polymeric matrix materials, to induce bone formation, including endochondral bone formation, under conditions where true replacement bone otherwise would not occur. For example, when combined with a matrix material, these osteogenic proteins induce formation of new bone in large segmental bone defects, spinal fusions, and fractures.

Naturally-sourced matrices, such as collagen, can be replaced with inert materials such as plastic, but plastic is not a suitable substitute since it does not resorb and is limited to applications requiring simple geometric configurations. To date, biodegradable polymers and copolymers have also been used as matrices admixed with osteogenic proteins for repair of non-union defects. While such matrices may overcome some of the above-described insufficiencies, use of these matrices necessitates determination and control of features such as polymer chemistry, particle size, biocompatibility and other particulars critical for operability. For example, pores must be formed in the polymer in a manner which ensures adsorption of protein into the matrix and biodegradation of the matrix. Prior to use of the polymeric matrix, therefore, it is necessary to undergo the extra step of treating the polymer to induce the formation of pores of the appropriate size.

Standard osteogenic devices, which include either collagen or polymer matrices in admixture with osteogenic protein, lend themselves less amenable to manipulation during surgery. Standard osteogenic devices often have a dry, sandy consistency and can be washed away whenever the defect site is irrigated during surgery, and/or by blood and/or other fluids infiltrating the site post-surgery. The addition of certain materials to these compositions can aid in providing a more manageable composition for handling during surgery. U.S. Pat. Nos. 5,385,887; 5,520,923; 5,597,897 and International Publication WO 95/24210 describe compositions containing a synthetic polymer matrix, osteogenic protein, and a carrier for such a purpose. Such compositions have been limited, however, to synthetic polymer matrices because of a desire to overcome certain alleged adverse immunologic reactions contemplated associated with other types of matrices especially biologically-derived matrices, including some forms of collagen. These compositions, therefore, suffer from the same feasibility concerns for optimizing polymer chemistry, particle size, biocompatibility, etc., described above.

Needs remain for compositions and methods for repairing bone and cartilage defects which provide greater ease in handling during surgery and which do not rely on synthetic polymer matrices. Needs also remain for methods and compositions that can enhance the rate and quality of new bone and cartilage formation.

Accordingly, it is an object of the instant invention to provide improved osteogenic devices and methods of use thereof for repairing bone defects, cartilage defects and/or osteochondral defects that: are easier to manipulate during surgery; circumvent the concerns of polymer chemistry, particle size and biocompatibility associated with the use of synthetic polymer matrices; and, which permit accelerated bone formation and more stable cartilage repair using lower doses of osteogenic protein than can be achieved using devices and methods now in the art. It is a further object of the instant invention to provide osteogenic devices and methods of use thereof for repairing non-healing, non-union defects and for promoting articular cartilage repair in chondral or osteochondral defects. Yet another object of the instant invention is to provide devices and methods for repair of bone and cartilage defects without surgical intervention. These and other objects, along with advantages and features of the invention disclosed herein, will be apparent from the description, drawings and claims that follow.

SUMMARY OF THE INVENTION

The present invention is based on the discovery that admixing osteogenic protein and a non-synthetic, non-polymeric matrix such as collagen or β-tricalcium phosphate (β-TCP) with a binding agent yields an improved osteogenic device with enhanced bone and cartilage repair capabilities. Not only can such improved devices accelerate, the rate of repair, these devices also can promote formation of high quality, stable repair tissue, particularly cartilage tissue. Additionally, the foregoing benefits can be achieved using significantly less osteogenic protein than required by standard osteogenic devices. While not wishing to be bound by theory, the aforementioned unexpected properties likely can be attributed to a complementary or synergistic interaction between the non-polymeric matrix and the binding agent. In view of existing orthopedic and reconstructive technologies, these discoveries are unexpected and were heretofore unappreciated.

The invention provides, in one aspect, a novel device for inducing local bone and cartilage formation comprising osteogenic protein, matrix derived from non-synthetic, non-polymeric material, and binding agent. As contemplated herein, the device preferably comprises osteogenic proteins such as, but not limited to OP-1, OP-2, BMP-2, BMP-4, BMP-5 and BMP-6. A currently preferred osteogenic protein is OP-1. As used herein, the terms "morphogen", "bone morphogen", "bone morphogenic protein", "BMP", "osteogenic protein" and "osteogenic factor" embrace the class of proteins typified by human osteogenic protein 1 (hOP-1). Nucleotide and amino acid sequences for hOP-1 are provided in Seq. ID Nos. 1 and 2, respectively. For ease of description, hOP-1 is recited herein below as a representative osteogenic protein. It will be appreciated by the artisan of ordinary skill in the art, however, that OP-1 merely is representative of the TGF-β subclass of true tissue morphogens competent to act as osteogenic proteins, and is not intended to limit the description. Other known, and useful proteins include, BMP-2, BMP-3, BMP-3b, BMP-4, BMP-5, BMP-6, BMP-8, BMP-9, BMP-10, BMP-11, BMP-12, BMP-13, BMP-15, GDF-1, GDF-2, GDF-3, GDF-5, GDF-6, GDF-7, GDF-8, GDF-9, GDF-10, GDF-11, GDF-12, NODAL, UNIVIN, SCREW, ADMP, NEURAL and osteogenically active amino acid variants thereof. In one preferred embodiment, the proteins useful in the invention include biologically active species variants of any of these proteins, including conservative amino acid sequence variants, proteins encoded by degenerate nucleotide sequence variants, and osteogenically active proteins sharing the conserved seven cysteine skeleton as defined herein and encoded by a DNA sequence competent to hybridize to a DNA sequence encoding an osteogenic protein disclosed herein, including, without limitation, OP-1, BMP-5, BMP-6, BMP-2, BMP-4 or GDF-5, GDF-6 or GDF-7. In another embodiment, useful osteogenic proteins include those sharing the conserved seven cysteine domain and sharing at least 70% amino acid sequence homology (similarity) within the C-terminal active domain, as defined herein. In still another embodiment, the osteogenic proteins of the invention can be defined as osteogenically active proteins having any one of the generic sequences defined herein, including OPX (SEQ ID No: 3) and Generic Sequences 7 and 8, or Generic Sequences 9 and 10.

OPX accommodates the homologies between the various species of the osteogenic OP-1 and OP-2 proteins, and is described by the amino acid sequence presented herein below and in SEQ ID NO: 3. Generic sequence 9 is a 96 amino acid sequence containing the six cysteine skeleton defined by hOP-1 (residues 335-431 of SEQ ID NO: 2) and wherein the remaining residues accommodate the homologies of OP-1, OP-2, OP-3, BMP-2, BMP-3, BMP-4, BMP-5, BMP-6, BMP-8, BMP-9, BMP-10, BMP-11, BMP-15, GDF-1, GDF-3, GDF-5, GDF-6, GDF-7, GDF-8, GDF-9, GDF-10, GDF-11, UNIVIN, NODAL, DORSALIN, NURAL, SCREW and ADMP. That is, each of the non-cysteine residues is independently selected from the corresponding residue in this recited group of proteins. Generic Sequence 10 is a 102 amino acid sequence which includes a 5 amino acid sequence added to the N-terminus of the Generic Sequence 9 and defines the seven cysteine skeleton of hOP-1 (330-431 SEQ ID NO: 2). Generic Sequences 7 and 8 are 96 and 102 amino acid sequences, respectively, containing either the six cysteine skeleton (Generic Sequence 7) or the seven cysteine skeleton (Generic Sequence 8) defined by hOP-1 and wherein the remaining residues non-cysteine accommodate the homologies of: OP-1, OP-2, OP-3, BMP2, BMP3, BMP4, 60A, DPP, Vg1, BMP5, BMP6, Vgr-1, and GDF-1.

As taught below, preferred matrices are non-synthetic, non-polymeric materials and can be naturally-sourced or derived from biological materials. Examples of preferred matrices include, but are not limited to, collagen, demineralized bone and β-TCP. One currently preferred matrix is collagen. Another currently preferred matrix is β-TCP. Thus, the devices of the instant invention do not comprise as a primary component synthetic polymeric matrices such as homopolymers or copolymers of α-hydroxy acetic acid and/or α-hydroxy propionic acid, including racemic mixtures thereof.

With respect to binding agents, the instant devices preferably comprise agents useful as gel-forming, viscosity-increasing, suspending and/or emulsifying agents. A currently preferred group of binding agents is the alkycellulose group; especially methylcelluloses such as carboxymethylcellulose. Other suitable binding agents include other cellulose gums, sodium alginate, dextrans and gelatin powder. Another particularly preferred binding agent is fibrin glue. As used herein the term "fibrin glue" means a composition comprising mammalian fibrinogen and thrombin. In certain embodiments, the improved devices of the instant invention further comprise a wetting agent such as, but not limited to, saline or other aqueous physiological solution.

The improved devices of the instant invention can assume a variety of configurations. The configuration will depend, in part, upon the type of binding agent and wetting agent employed. As disclosed herein, one currently preferred embodiment can have a putty consistency. This particular configuration is especially suitable for treating open defects in accordance with the methods of the instant invention. Another currently preferred embodiment of improved osteogenic device can have a viscous fluid consistency. This particular configuration is especially suitable for treating closed defects in accordance with the methods disclosed herein. Depending upon the configuration of the improved device, providing it to a defect site can be accomplished by a variety of delivery modes. For example, a putty can be packed in and/or around the defect or extruded as a bead from a large-bore apparatus. Alternatively, a viscous liquid can be injected into and/or around the defect, or alternatively brushed and/or painted on the defect's surface(s). Exploitation of a variety of these possible embodiments to repair bone and cartilage defects is exemplified herein.

Among the characteristics of a preferred binding agent is an ability to render the device: pliable, shapeable and/or malleable; injectable; adherent to bone, cartilage, muscle and other tissues; resistant to disintegration upon washing and/or irrigating during surgery; and, resistant to dislodging during surgery, suturing and post-operatively, to name but a few. Additionally, in certain preferred embodiments, a binding agent can achieve the aforementioned features and benefits when present in low proportions. For example, a currently preferred improved device comprises approximately 1 part binding agent and approximately 5 parts matrix. Certain other preferred embodiments comprise approximately 1 part binding agent and approximately 10 parts matrix, while still others comprise approximately 1 part binding agent and approximately 25 parts matrix. Another currently preferred device comprises approximately 3 parts binding agent to 5 parts matrix. Certain binding agents can be used in equal or greater proportions relative to matrix. Another currently preferred device comprises 1 part binding agent and 3 parts matrix. As exemplified herein, improved devices of widely divergent proportions can induce bone and cartilage formation. Exemplified herein are improved devices having parts of binding agent to parts of matrix ranging from approximately 1:1 to 4:1 as well as from approximately 1:2 to 1:5 and 1:10 to 1:25, as well as 1:25 to 1:50. Any proportion of binding agent to matrix can be used to practice the instant invention.

Furthermore, the instant invention contemplates that an improved osteogenic device can comprise more than one matrix material in combination; the relative proportions can be varied to achieve the desired clinical outcome and can be routinely determined using ordinary skill. A currently preferred matrix is collagen, especially bovine collagen. Another suitable matrix is demineralized bone. Yet other suitable matrices are hydroxyapatites (HAp) of varying calcium:phosphate (Ca/P) molar ratios, porosity and crystallinity; bioactive ceramics; and calcium phosphate ceramics, to name but a few. Additionally, admixtures of the foregoing wherein HAp/tricalciumphosphate ratios are manipulated are also contemplated herein. In a particularly preferred embodiment, the matrix is β-tricalcium phosphate (β-TCP).

In another aspect, the instant invention provides methods for inducing local bone or cartilage formation for repair of bone, cartilage or osteochondral defects. The instant methods are contemplated as useful to induce formation of at least endochondral bone, intramembranous bone, and articular cartilage. As disclosed herein, methods of repair include treatment of both closed and open defects with the above-described improved osteogenic devices. As taught herein, the methods of the instant invention can be practiced using improved devices that are of sufficient volume to fill the defect site, as well as using improved devices that are not. Moreover, as a result of this discovery, embodiments are now available for promoting bone and/or cartilage defect repair without requiring surgical intervention. Availability of such methods has implications for compromised individuals such as diabetics, smokers, obese individuals and others whose overall health and impaired blood flow to their extremities are placed at risk when surgical intervention is required. Examples of defects include, but are not limited to, critical size defects, non-critical size defects, non-union fractures, fractures, osteochondral defects, chondral defects and periodontal defects.

In another aspect, the instant invention provides a kit for practice of the above-described methods. As contemplated herein, one embodiment of a kit for inducing local bone formation or cartilage formation comprises an improved device wherein the osteogenic protein and matrix are packaged in the same receptacle. In other embodiments, the osteogenic protein, matrix and binding agent are in the same receptacle. In yet other embodiments, wetting agent is also provided and packaged separately from the other kit components.

Because the instant invention provides practitioners with improved materials and methods for bone and cartilage repair, including repair of articular cartilage present in mammalian joints, it overcomes problems otherwise encountered using the methods and devices of the art. For example, the instant invention can induce formation of bona fide hyaline cartilage rather than fibrocartilage at a defect site. Functional hyaline cartilage forms on the articulating surface of bone at a defect site and does not degenerate over time to fibrocartilage. By contrast, prior art methods generally ultimately result in development of fibrocartilage at the defect site. Unlike hyaline cartilage, fibrocartilage lacks the physiological ability to restore articulating joints to their full capacity. Thus, when improved osteogenic devices are used in accordance with the instant methods, the practitioner can substantially restore an osteochondral or a chondral defect in a functionally articulating joint and avoid the undesirable formation of fibrocartilage typical of prior art methods. As contemplated herein, the invention further embodies allogenic replacement materials for repairing avascular tissue in a skeletal joint which results in formation of mechanically and functionally viable replacement tissues at a joint.

In summary, the methods, devices, and kits of the present invention can be used to induce endochondral or intramembranous bone formation for repairing bone defects which do not heal spontaneously, as well as for promoting and enhancing the rate and/or quality of new bone formation, particularly in the repair of fractures and fusions, including spinal fusions. The methods, devices, and kits also can induce repair of osteochondral and/or subchondral defects, i.e., can induce formation of new bone and/or the overlying surface cartilage. The present invention is particularly suitable for use in repair of defects resulting from deteriorative or degenerative diseases such as, but not limited to, osteochondritis dessicans. It is also particularly suitable for use in patients requiring repetitive reconstructive surgeries, as well as cancer patients. Other applications include, but are not limited to, prosthetic repair, spinal fusion, scoliosis, cranial/facial repair, and massive allograft repair.

BRIEF DESCRIPTION OF THE DRAWINGS

The foregoing and other objects and features of the invention, as well as the invention itself, may be more fully understood from the following description, when read together with the accompanying drawings, in which.

DETAILED DESCRIPTION OF PREFERRED EMBODIMENTS

Figure 1:
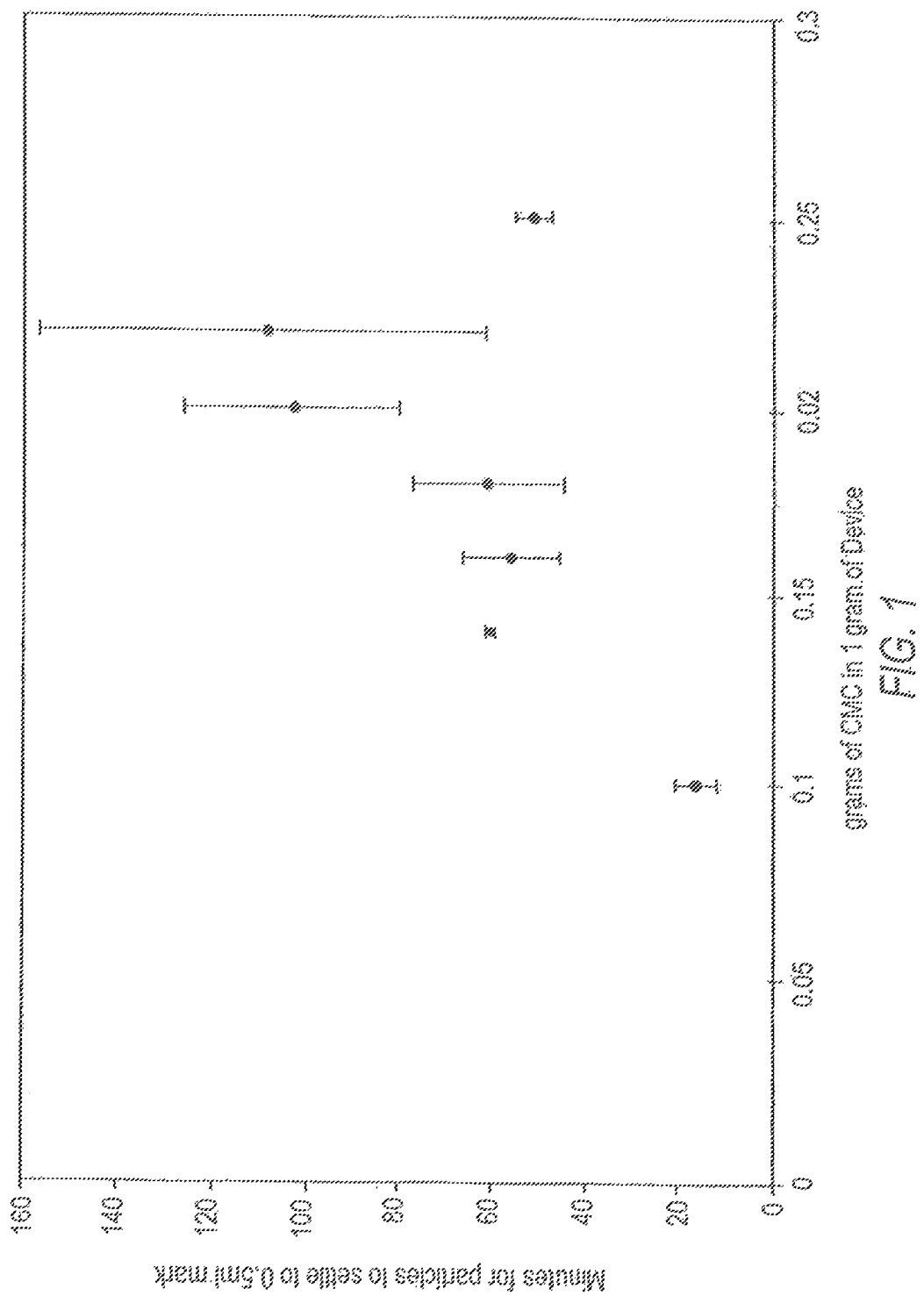
FIG. 1 is a graph depicting cohesiveness properties of varying parts (w/w) of binding agent to parts (w/w) of standard OP device.

In order to more clearly and concisely describe the subject matter of the claimed invention, the following definitions are intended to provide guidance as to the meaning of specific terms used in the following written description and appended claims.

"Bone formation" means formation of endochondral bone or formation of intramembranous bone. In humans, bone formation begins during the first 6-8 weeks of fetal development. Progenitor stem cells of mesenchymal origin migrate to predetermined sites, where they either: (a) condense, proliferate, and differentiate into bone-forming cells (osteoblasts), a process observed in the skull and referred to as "intramembranous bone formation;" or, (b) condense, proliferate and differentiate into cartilage-forming cells (chondroblasts) as intermediates, which are subsequently replaced with bone-forming cells. More specifically, mesenchymal stem cells differentiate into chondrocytes. The chondrocytes then become calcified, undergo hypertrophy and are replaced by newly formed bone made by differentiated osteoblasts, which now are present at the site. Subsequently, the mineralized bone is extensively remodeled, thereafter becoming occupied by an ossicle filled with functional bone-marrow elements. This process is observed in long bones and referred to as "endochondral bone formation." In postfetal life, bone has the capacity to repair itself upon injury by mimicking the cellular process of embryonic endochondral bone development. That is, mesenchymal progenitor stem cells from the bone-marrow, periosteum, and muscle can be induced to migrate to the defect site and begin the cascade of events described above. There, they accumulate, proliferate, and differentiate into cartilage, which is subsequently replaced with newly formed bone.

"Bone" refers to a calcified (mineralized) connective tissue primarily comprising a composite of deposited calcium and phosphate in the form of hydroxyapatite, collagen (primarily Type I collagen) and bone cells such as osteoblasts, osteocytes and osteoclasts, as well as to bone marrow tissue which forms in the interior of true endochondral bone. Bone tissue differs significantly from other tissues, including cartilage tissue. Specifically, bone tissue is vascularized tissue composed of cells and a biphasic medium comprising a mineralized, inorganic component (primarily hydroxyapatite crystals) and an organic component (primarily of Type I collagen). Glycosaminoglycans constitute less than 2% of this organic component and less than 1% of the biphasic medium itself, or of bone tissue per se. Moreover, relative to cartilage tissue, the collagen present in bone tissue exists in a highly-organized parallel arrangement. Bony defects, whether from degenerative, traumatic or cancerous etiologies, pose a formidable challenge to the reconstructive surgeon. Particularly difficult is reconstruction or repair of skeletal parts that comprise part of a multi-tissue complex, such as occurs in mammalian joints.

"Cartilage formation" means formation of connective tissue containing chondrocytes embedded in an extracellular network comprising fibrils of collagen (predominantly Type II collagen along with other minor types such as Types IX and XI), various proteoglycans, other proteins and water. "Articular cartilage" refers specifically to hyaline or articular cartilage, an avascular non-mineralized tissue which covers the articulating surfaces of the portions of bones in joints and allows movement in joints without direct bone-to-bone contact, thereby preventing wearing down and damage of opposing bone surfaces. Normal healthy articular cartilage is referred to as "hyaline," i.e. having a characteristic frosted glass appearance. Under physiological conditions, articular cartilage tissue rests on the underlying, mineralized bone surface called subchondral bone, which contains highly vascularized ossicles. The articular, or hyaline cartilage, found at the end of articulating bones is a specialized, histologically distinct tissue and is responsible for the distribution of load resistance to compressive forces, and the smooth gliding that is part of joint function. Articular cartilage has little or no self-regenerative properties. Thus, if the articular cartilage is torn or worn down in thickness or is otherwise damaged as a function of time, disease or trauma, its ability to protect the underlying bone surface is comprised. In normal articular cartilage, a balance exists between synthesis and destruction of the above-described extracellular network. However, in tissue subjected to repeated trauma, for example, due to friction between misaligned bones in contact with one another, or in joint diseases characterized by net loss of articular cartilage, e.g., osteoarthritis, an imbalance occurs between synthesis and degradation.

Other types of cartilage in skeletal joints include fibrocartilage and elastic cartilage. Secondary cartilaginous joints are formed by discs of fibrocartilage that join vertebrae in the vertebral column. In fibrocartilage, the mucopolysaccharide network is interlaced with prominent collagen bundles and the chondrocytes are more widely scattered than in hyaline cartilage. Elastic cartilage contains collagen fibers that are histologically similar to elastin fibers. Cartilage tissue, including articular cartilage, unlike other connective tissues, lacks blood vessels, nerves, lymphatics and basement membrane. Cartilage is composed of chondrocytes, which synthesize an abundant extracellular milieu composed of water, collagens, proteoglycans and noncollagenous proteins and lipids. Collagen serves to trap proteoglycans and to provide tensile strength to the tissue. Type II collagen is the predominant collagen in cartilage tissue. The proteoglycans are composed of a variable number of glycosaminoglycan chains, keratin sulphate, chondroitin sulphate and/or dermatan sulphate, and N-lined and O-linked oligosaccharides covalently bound to a protein core.

Articular, or hyaline, cartilage can be distinguished from other forms of cartilage by both its morphology and its biochemistry. Certain collagens such as the fibrotic cartilaginous tissues, which occur in scar tissue, for example, are keloid and typical of scar-type tissue, i.e., composed of capillaries and abundant, irregular, disorganized bundles of Type I and Type II collagen. In contrast, articular cartilage is morphologically characterized by superficial versus mid versus deep zones which show a characteristic gradation of features from the surface of the tissue to the base of the tissue adjacent to the bone. In the superficial zone, for example, chondrocytes are flattened and lie parallel to the surface embedded in an extracellular network that contains tangentially arranged collagen and few proteoglycans. In the mid zone, chondrocytes are spherical and surrounded by an extracellular network rich in proteoglycans and obliquely organized collagen fibers. In the deep zone, close to the bone, the collage fibers are vertically oriented. The keratin sulphate rich proteoglycans increase in concentration with increasing distance from the cartilage surface. For a detailed description of articular cartilage microstructure, see, for example, (Aydelotte and Kuettner, (1988), *Conn. Tiss. Res.* 18:205; Zanetti et al., (1985), *J. Cell Biol.* 101:53; and Poole et al., (1984), *J. Anat.* 138:13. Biochemically, articular collagen can be identified by the presence of Type II and Type IX collagen, as well as by the presence of well-characterized proteoglycans, and by the absence of Type X collagen, which is associated with endochondral bone formation.

Two types of defects are recognized in articular surfaces, i.e., full-thickness defects and superficial defects. These defects differ not only in the extent of physical damage to the cartilage, but also in the nature of the repair response each type of lesion can elicit. Full-thickness defects, also referred to herein as "osteochondral defects," of an articulating surface include damage to the hyaline cartilage, the calcified cartilage layer and the subchondral bone tissue with its blood vessels and bone marrow. Full-thickness defects can cause severe pain, since the bone plate contains sensory nerve endings. Such defects generally arise from severe trauma and/or during the late stages of degenerative joint disease, such a osteoarthritis. Full-thickness defects may, on occasion, lead to bleeding and the induction of a repair reaction from the subchondral bone. In such instances, however, the repair tissue formed is a vascularized fibrous type of cartilage with insufficient biomechanical properties, and does not persist on a long-term basis. In contrast, superficial defects in the articular cartilage tissue are restricted to the cartilage tissue itself. Such defects, also referred to herein as "chondral" or "subchondral defects", are notorious because they do not heal and show no propensity for repair reactions. Superficial defects may appear as fissures, divots, or clefts in the surface of the cartilage. They contain no bleeding vessels (blood spots), such as those seen in full-thickness defects. Superficial defects may have no known cause, but they are often the result of mechanical derangements that lead to a wearing down of the cartilaginous tissue. Such mechanical derangements may be caused by trauma to the joint, e.g., a displacement of torn meniscus tissue into the joint, meniscectomy, a laxation of the joint by a torn ligament, malalignment of joints, or bone fracture, or by hereditary diseases. Superficial defects are also characteristic of early stages of degenerative joint diseases, such as osteoarthritis. Since the cartilage tissue is not innervated or vascularized, superficial defects do not heal and often degenerate into full-thickness defects.

"Defect" or "defect site", as contemplated herein, can define a bony structural disruption requiring repair. The defect further can define an osteochondral defect, including a structural disruption of both the bone and overlying cartilage. A defect can assume the configuration of a "void", which is understood to mean a three-dimensional defect such as, for example, a gap, cavity, hole or other substantial disruption in the structural integrity of a bone or joint. A defect can be the result of accident, disease, surgical manipulation, and/or prosthetic failure. In certain embodiments, the defect is a void having a volume incapable of endogenous or spontaneous repair. Such defects are generally twice the diameter of the subject bone and are also called "critical size" defects. For example, in a canine ulna defect model, the art recognizes such defects to be approximately 3-4 cm, generally at least approximately 2.5 cm, gap incapable of spontaneous repair. See, for example, Schmitz et al., *Clinical Orthopaedics and Related Research* 205:299-308 (1986); and Vukicevic et al., in *Advanced in Molecular and Cell Biology*, Vol. 6, pp. 207-224 (1993)(JAI Press, Inc.), the disclosures of which are incorporated by reference herein. In rabbit and monkey segmental defect models, the gap is approximately 1.5 cm and 2.0 cm, respectively. In other embodiments, the defect is a non-critical size segmental defect. Generally, these are capable of some spontaneous repair, albeit biomechanically inferior to those made possible by practice of the instant innovation. In certain other embodiments, the defect is an osteochondral defect, such as an osteochondral plug. Such a defect traverses the entirety of the overlying cartilage and enters, at least in part, the underlying bony structure. In contrast, a chondral or subchondral defect traverses the overlying cartilage, in part or in whole, respectively, but does not involve the underlying bone. Other defects susceptible to repair using the instant invention include, but are not limited to, non-union fractures; bone cavities; tumor resection; fresh fractures (distracted or undistracted); cranial/facial abnormalities; periodontal defects and irregularities; spinal fusions; as well as those defects resulting from diseases such as cancer, arthritis, including osteoarthritis, and other bone degenerative disorders such as osteochondritis dessicans.

"Repair" is intended to mean new bone and/or cartilage formation which is sufficient to at least partially fill the void or structural discontinuity at the defect. Repair does not, however, mean, or otherwise necessitate, a process of complete healing or a treatment which is 100% effective at restoring a defect to its pre-defect physiological/structural/mechanical state.

"Matrix", as contemplated herein, means a non-polymeric, non-synthetic material that can act as an osteoconductive substrate and has a scaffolding structure on which infiltrating cells can attach, proliferate and participate in the morphogenic process culminating in bone formation. As contemplated herein, matrix does not include polymeric, synthetic materials such as polymeric matrices comprising homopolymers or copolymers of $\alpha$-hydroxy acetic acid and/or $\alpha$-hydroxy proponic acid, including racemic mixtures thereof. Specifically, matrices as contemplated herein do not include homopolymers or copolymers of glycolic acid, lactic acid, and butyric acid, including derivatives thereof. For example, the matrix of the instant invention can be derived from biological, or naturally-sourced, or naturally-occurring materials. A suitable matrix must be particulate and porous, with porosity being a feature critical to its effectiveness in inducing bone formation, particularly endochondral bone formation. It is understood that the term "matrix" means a structural component or substrate intrinsically having a three-dimensional form upon which certain cellular events involved in endochondral bone morphogenesis will occur; a matrix acts as a temporary scaffolding structure for infiltrating cells having interstices for attachment, proliferation and differentiation of such cells. The instant invention contemplates that an improved osteogenic device can comprise more than one matrix material in combination; the relative proportions can be varied to achieve the desired clinical outcome and can be routinely determined using ordinary skill. A currently preferred matrix is collagen, especially bovine collagen. Another suitable matrix is demineralized bone. Yet other suitable matrices are hydroxyapatites (HAp) of varying calcium:phosphate (Ca/P) molar ratios, porosity and crystallinity; bioactive ceramics; and calcium phosphate ceramics, to name but a few. Additionally, admixtures of the foregoing wherein HAp/tricalciumphosphate ratios are manipulated are also contemplated herein. These matrices can be obtained commercially in the form of granules, blocks and powders. For example, Pyrost® is a HAp block derived from bovine bone (Osteo AG, Switzerland); Collapta® is a HAp sponge containing collagen (Osteo AG, Switzerland); tricalcium phosphates ($\beta$-TCP) can be obtained from Pharma GmbH (Germany) as Cerasob®, as well as from Clarkson Chromatography Products, Inc. (S. Williamsport, Pa.) or Osteonics (Netherlands); TCP/HAp granule admixtures can be obtained from Osteonics (Netherlands); and 100% HAp powder or granules can be obtained from CAM (a subsidiary of Osteotech, N.J.). Preparation and characterization of certain of the aforementioned matrices have been extensively described in the art and necessitates no more than routine experimentation and ordinary skill. See, for example, U.S. Pat. Nos. 4,975,526; 5,011,691; 5,171,574; 5,266,683; 5,354,557; and U.S. Pat. No. 5,468,845, the disclosures of which are herein incorporated by reference. Other of the aforementioned matrices have also been well described in the art. See, for example, biomaterials treatises such as LeGeros and Daculsi in Handbook of Bioactive Ceramics, II pp. 17-28 (1990, CRC Press); and other published descriptions such as Yang Cao, Jie Weng Biomaterials 17, (1996) pp. 419-424; LeGeros, *Adv. Dent. Res.* 2, 164 (1988); Johnson et al., *J. Orthopaedic Research,* 1996, Vol. 14, pp. 351-369; and Piittelli et al., *Biomaterials* 1996, Vol. 17, pp. 1767-1770, the disclosures of which are herein incorporated by reference.

Sintered, high fired β-TCP (β-tricalcium phosphate) is a currently preferred matrix. Sintered β-TCP has a higher dissolution rate than sintered HAps and sintered biphasic calcium phosphate (BCP). The ability of β-TCP to support bone formation appears to be based, in part, on the size of the Ca/P granules in the matrix. Sintered β-TCP having particle sizes of between about 212 μm and about 425 μm are most preferred and may be obtained from Clarkson Chromatography Products, Inc. (S. Williamsport, Pa.) or Osteonics (Netherlands). Upon implantation, devices containing particles sized within this range show high rates of resorption by image analysis and low inflammatory responses when implanted at a rat sub-cutaneous site, as described elsewhere herein.

"Osteogenic device" is understood to mean a composition comprising at least osteogenic protein dispersed in a matrix. As disclosed herein, an "improved osteogenic device" comprises osteogenic protein, a matrix as defined above, and a binding agent as defined below. In contrast, a "standard osteogenic device" comprises osteogenic protein and a matrix, but not a binding agent; standard osteogenic devices can comprise either a synthetic, polymeric or a matrix as defined above. In the Examples and teachings set forth below, standard osteogenic devices are further designated; standard devices, OP device, OP-1 device, or OP. Improved osteogenic devices are further designated: CMC-containing device, CMC-containing standard device, CMC/OP-1 device, OP-1/CMC/collagen, OPCMC/collagen, and fibrin glue-containing improved device. As used herein, a "mock device" does not contain osteogenic protein and is formulated free of any known osteoinductive factor. The instant invention also contemplates improved devices comprising at least two different osteogenic proteins and/or at least two different matrices; as defined herein. Other embodiments of improved device can further comprise at least two different binding agents, as defined herein. In still other embodiments, any one of the aforementioned improved devices can further comprise a wetting agent, as defined herein. Any of the aforementioned embodiments can also include radiopaque components, such as commercially available contrast agents. Generally, there are three well-known types of such agents—hydroxyapatites, barium sulfate, and organic iodine. Devices containing radiopaque components are particularly useful for device administration at a closed defect site, as discussed elsewhere herein. Identification of a suitable radiopaque component requires only ordinary skill and routine experimentation. See, for example, radiographic treatises including, Ehrlich and McCloskey, *Patient Care in Radiography* (Mosby Publisher, 1993); Carol, *Fuch's Radiographic Exposure, Processing and Quality Control* (Charles C. Thomas Publisher, 1993); and Snopek, *Fundamentals of Special Radiographic Procedures,* (W.B. Saunders Company, 1992), the disclosures of which are herein incorporated by reference.

Preferred embodiments of improved devices are adherent to bone, cartilage, muscle and/or other tissue. They have improved handling properties and are resistant to dislodging upon irrigation during surgery and upon suturing. Similarly, they are cohesive and not washed away, disintegrated or diluted by irrigation and/or infiltrating body fluids such as blood. Preferred embodiments remain adherent post-surgery, even at an articulating joint. Of particular importance is that improved devices are readily confined to the defect site. Functionally, the improved osteogenic device of the instant invention induces accelerated bone and/or cartilage formation, as well as higher quality, more stable repair tissue and can achieve those benefits at doses of osteogenic protein lower than required with a standard osteogenic device. Thus, the admixture of osteogenic protein with non-synthetic, non-polymeric matrix and a binding agent has unexpected properties upon which the skilled practitioner can now capitalize as exemplified herein. One currently preferred embodiment comprises OP-1, collagen matrix and the binding agent carboxymethylcellulose (CMC). As discussed below, an advantage associated with the binding agent, CMC, is its effectiveness even when present in low relative amounts. For example, in certain embodiments exemplified herein, OP-1 can be used in amounts ranging from approximately 1.25 to 2.50 mg per approximately 1000 mg collagen and per approximately 180 to 200 mg CMC. Other currently preferred embodiments comprise OP-1, collagen matrix and the binding agent fibrin glue; or OP-1, β-TCP matrix and the binding agent fibrin glue. In certain embodiments exemplified herein, approximately 40 mg fibrin glue can be used with 1000 mg β-TCP or 1000 mg collagen. In yet other embodiments, approximately 20 mg fibrin glue can be used with 1000 mg collagen to support bone and/or cartilage formation. These matrices and binding agents exhibit all of the aforementioned preferred handling characteristics associated with an improved osteogenic device.

In certain other embodiments, these amounts of protein, matrix and binding agent can be increased or decreased according to the conditions and circumstances related to defect repair. A wetting agent such as saline can be further added. As exemplified below, a preferred configuration for implantation at an open defect site assumes a putty consistency. It can be molded and shaped by the surgeon prior to implantation. This configuration is achieved by adjusting the proportion of matrix to binding agent to wetting agent in a manner similar to that taught herein. As further exemplified below, closed defects can be treated with a looser, more fluid device configuration resembling a viscous liquid. Such configurations can be injected without surgical intervention at a defect site. Again, merely adjusting the proportions of matrix to binding agent to wetting agent can achieve this embodiment. Currently, a preferred improved device comprises approximately 1 part binding agent (w/w) to approximately 5 parts matrix (w/w). As described herein below, other proportions can be used to prepare improved devices, depending upon the nature of binding agent and/or matrix.

Of course, an essential feature of any formulation of improved osteogenic device is that it must be effective to provide at least a local source of osteogenic protein at the defect site, even if transient. As exemplified below, the binding agent content of an improved osteogenic device does not affect protein release/retention kinetics. This is unexpected in view of contrary observations that polymer-containing standard devices failed to show clinically significant osteoinducing effects in the absence of sequestering material (defined to include cellulosic materials) because protein desorbtion was too great. (See, for example, U.S. Pat. No. 5,597,897.) As exemplified below, even when a binding agent as defined herein is present, protein is still desorbed from the improved device yet osteoinductive effects are readily apparent. While not wishing to be bound by theory, the unexpected features and benefits associated with the instant invention appear to relate less to a protein-binding agent interaction and more to a binding agent-matrix interaction. Specifically, binding agents as defined herein appear to complement and/or interact synergistically with the matrix required by the instant invention. This has heretofore been unappreciated, and this combination is discouraged by the teachings of the prior art. (See, for example, U.S. Pat. Nos. 5,520,923; 5,597,897; and WO 95/24210.)

The term "unitary" device refers to an improved osteogenic device provided to the practitioner as a single, pre-mixed formulation comprising osteogenic protein, matrix and binding agent. The term "non-unitary" device refers to an improved osteogenic device provided to the practitioner in at least two separate packages for admixing prior to use. Typically, a non-unitary device comprises at least binding agent packaged separately from the osteogenic protein and the matrix. The term "carrier" refers to an admixture of binding agent and matrix, as each is defined herein. Thus, for example, an improved osteogenic device as disclosed herein comprises osteogenic protein and a carrier.

In addition to osteogenic proteins, various growth factors, hormones, enzymes, therapeutic compositions, antibiotics, or other bioactive agents can also be contained within an improved osteogenic device. Thus, various known growth factors such as EGF, PDGF, IGF, FGF, TGF-α, and TGF-β can be combined with an improved osteogenic device and delivered to the defect site. An improved osteogenic device can also be used to deliver chemotherapeutic agents, insulin, enzymes, enzyme inhibitors and/or chemoattractant/chemotactic factors.

"Osteogenic protein", or bone morphogenic protein, is generally understood to mean a protein which can induce the full cascade of morphogenic events culminating in endochondral bone formation. As described elsewhere herein, the class of proteins is typified by human osteogenic protein (hOP-1). Other osteogenic proteins useful in the practice of the invention include osteogenically active forms of OP-1, OP-2, OP-3, BMP2, BMP3, BMP4, BMP5, BMP6, BMP9, DPP, Vg1, Vgr, 60A protein, GDF-1, GDF-3, GDF-5, 6, 7, BMP10, BMP11, BMP13, BMP15, UNIVIN, NODAL, SCREW, ADMP or NEURAL and amino acid sequence variants thereof. In one currently preferred embodiment, osteogenic protein includes any one of: OP-1, OP-2, OP-3, BMP2, BMP4, BMP5, BMP6, BMP9, and amino acid sequence variants and homologs thereof, including species homologs thereof. Particularly preferred osteogenic proteins are those comprising an amino acid sequence having at least 70% homology with the C-terminal 102-106 amino acids, defining the conserved seven cysteine domain, of human OP-1, BMP2, and related proteins. Certain preferred embodiments of the instant invention comprise the osteogenic protein, OP-1. Certain other preferred embodiments comprise mature OP-1 solubilized in a physiological saline solution. As further described elsewhere herein, the osteogenic proteins suitable for use with Applicants' invention can be identified by means of routine experimentation using the art-recognized bioassay described by Reddi and Sampath. "Amino acid sequence homology" is understood herein to mean amino acid sequence similarity. Homologous sequences share identical or similar amino acid residues, where similar residues are conservative substitutions for, or allowed point mutations of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. Examples of conservative variations include the substitution of one hydrophobic residue, such as isoleucine, valine, leucine or methionine, for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid, provided that antibodies raised to the substituted polypeptide also immunoreact with the unsubstituted polypeptide.

Proteins useful in this invention include eukaryotic proteins identified as osteogenic proteins (see U.S. Pat. No. 5,011,691, incorporated herein by reference), such as the OP-1, OP-2, OP-3 and CBMP-2 proteins, as well as amino acid sequence-related proteins, such as DPP (from *Drosophila*), Vg1 (from *Xenopus*), Vgr-1 (from mouse), GDF-1 (from humans, see Lee (1991), *PNAS* 88:4250-4254), 60A (from *Drosophila*, see Wharton et al. (1991) *PNAS* 88:9214-9218), dorsalin-1 (from chick, see Basler et al. (1993) *Cell* 73:687-702 and GenBank accession number L12032) and GDF-5 (from mouse, see Storm et al. (1994) *Nature* 368:639-643). BMP-3 is also preferred. Additional useful proteins include biosynthetic morphogenic constructs disclosed in U.S. Pat. No. 5,011,691, e.g., COP-1,3-5, 7 and 16, as well as other proteins known in the art. Still other proteins include osteogenically active forms of BMP-3b (see Takao, et al., (1996), *Biochem. Biophys. Res. Comm.* 219: 656-662. BMP-9 (see WO95/33830), BMP-15 (see WO96/35710), BMP-12 (see WO95/16035), CDMP-1 (see WO 94/12814), CDMP-2 (see WO94/12814), BMP-10 (see WO94/26893), GDF-1 (see WO92/00382), GDF-10 (see WO95/10539), GDF-3 (see WO94/15965) and GDF-7 (WO95/01802).

Still other useful proteins include proteins encoded by DNAs competent to hybridize to a DNA encoding an osteogenic protein as described herein, and related analogs, homologs, muteins (biosynthetic variants) and the like (see below). Certain embodiments of the improved osteogenic devices contemplated herein comprise osteogenic protein functionally and/or stably linked to matrix.

"Binding Agent", as used herein, means any physiologically-compatible material which, when admixed with osteogenic protein and matrix as defined herein, promotes bone and/or cartilage formation. Certain preferred binding agents promote such repair using less osteogenic protein than standard osteogenic devices. Other preferred binding agents can promote repair using the same amount of the osteogenic protein than the standard osteogenic devices while some require more to promote repair. As taught herein, the skilled artisan can determine an effective amount of protein for use with any suitable binding agent using only routine experimentation. Among the other characteristics of a preferred binding agent is an ability to render the device: pliable, shapeable and/or malleable; injectable; adherent to bone, cartilage, muscle and other tissues; resistant to disintegration upon washing and/or irrigating during surgery; and, resistant to dislodging during surgery, suturing and post-operatively, to name but a few. Additionally, in certain preferred embodiments, a binding agent can achieve the aforementioned features and benefits when present in low proportions. For example, a currently preferred improved device comprises approximately 1 part binding agent and approximately 5 parts matrix. Another currently preferred device comprises approximately 3 parts binding agent to 5 parts matrix. Yet other preferred devices comprise approximately 1 part binding agent and approximately 10 parts matrix while others comprise approximately 1 part binding agent and approximately 25 or 50 parts matrix. Certain binding agents can be used in equal or greater proportions relative to matrix, but, such agents should be tested as taught below to identify possible matrix dilution effects.

Those binding agents contemplated as useful herein include, but are not limited to: art-recognized suspending agents, viscosity-producing agents and emulsifying agents. In particular, art-recognized agents, such as cellulose gum derivatives, sodium alginate, and gelatin powder can be used. More particularly, cellulosic agents such as alkylcelluloses, are preferred including agents such as methylcellulose, methylhydroxyethylcellulose, hydroxyethylcellulose, hydroxypropylmethylcellulose, carboxymethylcellulose, sodium carboxymethylcellulose, and hydroxyalkylcelluloses, to name but a few. Currently, among the most preferred is carboxymethylcellulose, including the sodium salt thereof. As exemplified below, other binding agents suitable for use in the instant invention include, but are not limited to, dextran, mannitol, white petrolatum, sesame oil and admixtures thereof. Finally, also among the most preferred binding agents is fibrin glue, which comprises a mixture of mammalian fibrinogen and thrombin. In view of the teachings set forth herein, the artisan can identify suitable equivalents of the above-identified binding agents using merely routine experimentation and ordinary skill.

"Wetting Agent", as used herein, means any physiologically-compatible aqueous solution, provided it does not interfere with bone and/or cartilage formation. In certain embodiments of the instant invention, wetting agent is admixed with an improved device to achieve the consistency necessitated by the mode of defect repair. As taught herein, wetting agent can be used to achieve a putty configuration or, alternatively, a viscous liquid configuration. A currently preferred wetting agent is physiological saline. Equivalents can be identified by the artisan using no more than routine experimentation and ordinary skill.

The means for making and using the methods, implants and devices of the invention, as well as other material aspects concerning their nature and utility, including how to make and how to use the subject matter claimed, will be further understood from the following, which constitutes the best mode currently contemplated for practicing the invention. It will be appreciated that the invention is not limited to such exemplary work or to the specific details set forth in these examples.

I. Protein Considerations

A. Biochemical, Structural and Functional Properties of Bone Morphogenic Proteins Naturally occurring proteins identified and/or appreciated herein to be osteogenic or bone morphogenic proteins form a distinct subgroup within the loose evolutionary grouping of sequence-related proteins known as the TGF-β superfamily or supergene family. The naturally occurring bone morphogens share substantial amino acid sequence homology in their C-terminal regions (domains). Typically, the above-mentioned naturally occurring osteogenic proteins are translated as a precursor, having an N-terminal signal peptide sequence typically less than about 30 residues, followed by a "pro" domain that is cleaved to yield the mature C-terminal domain. The signal peptide is cleaved rapidly upon translation, at a cleavage site that can be predicted in a given sequence using the method of Von Heijne (1986) *Nucleic Acids Research* 14:4683-4691. The pro domain typically is about three times larger than the fully processed mature C-terminal domain.

In preferred embodiments, the pair of morphogenic polypeptides have amino acid sequences each comprising a sequence that shares a defined relationship with an amino acid sequence of a reference morphogen. Herein, preferred osteogenic polypeptides share a defined relationship with a sequence present in osteogenically active human OP-1, SEQ ID NO: 2. However, any one or more of the naturally occurring or biosynthetic sequences disclosed herein similarly could be used as a reference sequence. Preferred osteogenic polypeptides share a defined relationship with at least the C-terminal six cysteine domain of human OP-1, residues 335-431 of SEQ ID NO: 2. Preferably, osteogenic polypeptides share a defined relationship with at least the C-terminal seven cysteine domain of human OP-1, residues 330-431 of SEQ ID NO: 2. That is, preferred polypeptides in a dimeric protein with bone morphogenic activity each comprise a sequence that corresponds to a reference sequence or is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include those wherein one or more amino acid residues differs from the corresponding residue of a reference sequence, e.g., the C-terminal seven cysteine domain (also referred to herein as the conserved seven cysteine skeleton) of human OP-1, provided that this difference does not destroy bone morphogenic activity. Accordingly, conservative substitutions of corresponding amino acids in the reference sequence are preferred. Amino acid residues that are conservative substitutions for corresponding residues in a reference sequence are those that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. (1978), 5 *Atlas of Protein Sequence and Structure*, Suppl. 3, ch. 22 (pp. 354-352), Natl. Biomed. Res. Found., Washington, D.C. 20007, the teachings of which are incorporated by reference herein.

Examples of conservative substitutions include: Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. The term "conservative variation" also includes the use of a substituted amino acid in place of an unsubstituted parent amino acid provided that antibodies raised to the substituted polypeptide also immunoreact with the unsubstituted polypeptide.

Natural-sourced osteogenic protein in its mature, native form is a glycosylated dimer typically having an apparent molecular weight of about 30-36 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein, which also has osteogenic activity, has an apparent molecular weight of about 27 kDa. When reduced, the 27 kDa protein gives rise to two unglycosylated polypeptides, having molecular weights of about 14 kDa to 16 kDa, capable of inducing endochondral bone formation in a mammal. As described above, particularly useful sequences include those comprising the C-terminal 96 or 102 amino acid sequences of DPP (from *Drosophila*), Vg1 (from *Xenopus*), Vgr-1 (from mouse), the OP-1 and OP-2 proteins, proteins (see U.S. Pat. No. 5,011,691 and Oppermann et al., as well as the proteins referred to as BMP2, BMP3, BMP4 (see WO88/00205, U.S. Pat. No. 5,013,649 and WO91/18098), BMP5 and BMP6 (see WO90/11366, PCT/US90/01630), BMP8 and BMP9.

Other morphogenic proteins useful in the practice of the invention include morphogenically active forms of OP-1, OP-2, OP-3, BMP2, BMP3, BMP4, BMP5, BMP6, BMP9, GDF-5, GDF-6, GDF-7, DPP, Vg1, Vgr, 60A protein, GDF-1, GDF-3, GDF-5, GDF-6, GDF-7, BMP10, BMP11, BMP13, BMP15, UNIVIN, NODAL, SCREW, ADMP or NURAL and amino acid sequence variants thereof. In one currently preferred embodiment, osteogenic protein include any one of: OP-1, OP-2, OP-3, BMP2, BMP4, BMP5, BMP6, BMP9, and amino acid sequence variants and homologs thereof, including species homologs, thereof.

Publications disclosing these sequences, as well as their chemical and physical properties, include: OP-1 and OP-2: U.S. Pat. No. 5,011,691, U.S. Pat. No. 5,266,683, Ozkaynak et al. (1990) *EMBO J.* 9: 2085-2093; OP-3: WO94/10203 (PCT US93/10520); BMP2, BMP3, BMP4: WO88/00205, Wozney et al. (1988) *Science* 242: 1528-1534); BMP5 and BMP6: Celeste et al. (1991) *PNAS* 87: 9843-9847; Vgr-1: Lyons et al. (1989) *PNAS* 86: 4554-4558; DPP: Padgett et al. (1987) *Nature* 325: 81-84; Vg-1: Weeks (1987) *Cell* 51: 861-867; BMP-9: WO95/33830 (PCT/US95/07084); BMP10: WO94/26893 (PCT/US94/05290); BMP-11: WO94/26892 (PCT/US94/05288); BMP12: WO95/16035 (PCT/US94/14030); BMP-13: WO95/16035 (PCT/US94/14030); GDF-1: WO92/00382 (PCT/US91/04096) and Lee et al. (1991) *PNAS* 88: 4250-4254; GDF-8: WO94/21681 (PCT/US94/03019); GDF-9: WO94/15966 (PCT/US94/00685); GDF-10: WO95/10539 (PCT/US94/11440); GDF-11: WO96/01845 (PCT/US95/08543); BMP-15: WO96/36710 (PCT/US96/06540); MP121: WO96/01316 (PCT/EP95/02552); GDF-5 (CDMP-1, MP52): WO94/15949 (PCT/US94/00657) and WO96/14335 (PCT/US94/12814) and WO93/16099 (PCT/EP93/00350); GDF-6 (CDMP-2, BMP13): WO95/01801 (PCT/US94/07762) and WO96/14335 and WO95/10635 (PCT/US94/14030); GDF-7 (CDMP-3, BMP12): WO95/10802 (PCT/US94/07799) and WO95/10635 (PCT/US94/14030). In another embodiment, useful proteins include biologically active biosynthetic constructs, including novel biosynthetic morphogenic proteins and chimeric proteins designed using sequences from two or more known morphogens. See also the biosynthetic constructs disclosed in U.S. Pat. No. 5,011,691, the disclosure of which is incorporated herein by reference (e.g., COP-1, COP-3, COP-4, COP-5, COP-7, and COP-16).

In certain preferred embodiments, bone morphogenic proteins useful herein include those in which the amino acid sequences comprise a sequence sharing at least 70% amino acid sequence homology or "similarity", and preferably 80% homology or similarity, with a reference morphogenic protein selected from the foregoing naturally occurring proteins.

Preferably, the reference protein is human OP-1, and the reference sequence thereof is the C-terminal seven cysteine domain present in osteogenically active forms of human OP-1, residues 330-431 of SEQ ID NO: 2. In certain embodiments, a polypeptide suspected of being functionally equivalent to a reference morphogen polypeptide is aligned therewith using the method of Needleman, et al. (1970) J. Mol. Biol. 48:443-453, implemented conveniently by computer programs such as the Align program (DNAstar, Inc.). As noted above, internal gaps and amino acid insertions in the candidate sequence are ignored for purposes of calculating the defined relationship, conventionally expressed as a level of amino acid sequence homology or identity, between the candidate and reference sequences. "Amino acid sequence homology" is understood herein to include both amino acid sequence identity and similarity. Homologous sequences share identical and/or similar amino acid residues, where similar residues are conservation substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. In a currently preferred embodiment, the reference sequence is OP-1. Bone morphogenic proteins useful herein accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins, including those set forth and identified above. Certain particularly preferred morphogenic polypeptides share at least 60% amino acid identity with the preferred reference sequence of human OP-1, still more preferably at least 65% amino acid identity therewith.

In other preferred embodiments, the family of bone morphogenic polypeptides useful in the present invention, and members thereof, are defined by a generic amino acid sequence. For example, Generic Sequence 7 (SEQ ID NO: 4) and Generic Sequence 8 (SEQ ID NO: 5) disclosed below, accommodate the homologies shared among preferred protein family members identified to date, including at least OP-1, OP-2, OP-3, CBMP-2A, CBMP-2B, BMP-3, 60A, DPP, Vg1, BMP-5, BMP-6, Vgr-1, and GDF-1. The amino acid sequences for these proteins are described herein and/or in the art, as summarized above. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences provide an appropriate cysteine skeleton where inter- or intramolecular disulfide bonds can form, and contain certain critical amino acids likely to influence the tertiary structure of the folded proteins. In addition, the generic sequences allow for an additional cysteine at position 36 (Generic Sequence 7) or position 41 (Generic Sequence 8), thereby encompassing the morphogenically active sequences of OP-2 and OP-3.

Generic Sequence 7

Leu Xaa Xaa Xaa Phe Xaa Xaa
 1               5

Xaa Gly Trp Xaa Xaa Xaa Xaa Xaa Xaa Pro
     10                      15

```
                        Generic Sequence 7

Xaa Xaa Xaa Xaa Ala Xaa Tyr Cys Xaa Gly
                 20                  25

Xaa Cys Xaa Xaa Pro Xaa Xaa Xaa Xaa Xaa
                 30                  35

Xaa Xaa Xaa Asn His Ala Xaa Xaa Xaa Xaa
                 40                  45

Xaa Xaa Xaa Xaa Xaa Xaa Xaa Xaa Xaa Xaa
                 50                  55

Xaa Xaa Xaa Cys Cys Xaa Pro Xaa Xaa Xaa
                 60                  65

Xaa Xaa Xaa Xaa Xaa Leu Xaa Xaa Xaa Xaa
                 70                  75

Xaa Xaa Xaa Val Xaa Leu Xaa Xaa Xaa Xaa
                 80                  85

Xaa Met Xaa Val Xaa Xaa Cys Xaa Cys Xaa
                 90                  95
``` wherein each Xaa independently is selected from a group of one or more specified amino acids defined as follows: "Res." means "residue" and Xaa at res. 2=(Tyr or Lys); Xaa at res. 3=Val or Ile); Xaa at res. 4=(Ser, Asp or Glu); Xaa at res. 6=(Arg, Gln, Ser, Lys or Ala); Xaa at res. 7=(Asp or Glu); Xaa at res. 8=(Leu, Val or Ile); Xaa at res. 11=(Gln, Leu, Asp, His, Asn or Ser); Xaa at res. 12=(Asp, Arg, Asn or Gly); Xaa at res. 13=(Trp or Ser); Xaa at res. 14=(Ile or Val); Xaa at res. 15=(Ile or Val); Xaa at res. 16 (Ala or Ser); Xaa at res. 18=(Glu., Gln, Leu, Lys, Pro or Arg); Xaa at res. 19=(Gly or Ser); Xaa at res. 20=(Tyr or Phe); Xaa at res. 21=(Ala, Ser, Asp, Met, His, Gln, Leu or Gly); Xaa at res. 23=(Tyr, Asn or Phe); Xaa at res. 26=(Glu, His, Tyr, Asp, Gln, Ala or Ser); Xaa at res. 28=(Glu, Lys, Asp, Gln or Ala); Xaa at res. 30=(Ala, Ser, Pro, Gln, Ile or Asn); Xaa at res. 31=(Phe, Leu or Tyr); Xaa at res. 33=(Leu, Val or Met); Xaa at res. 34 (Asn, Asp, Ala, Thr or Pro); Xaa at res. 35=(Ser, Asp, Glu, Leu, Ala or Lys); Xaa at res. 36=(Tyr, Cys, His, Ser or Ile); Xaa at res. 37=(Met, Phe, Gly or Leu); Xaa at res. 38=(Asn, Ser or Lys); Xaa at res. 39=(Ala, Ser, Gly or Pro); Xaa at res. 40=(Thr, Leu or Ser); Xaa at res. 44=(Ile, Val or Thr); Xaa at res. 45=(Val, Leu, Met or Ile); Xaa at res. 46=(Gln or Arg); Xaa at res. 47=(Thr, Ala or Ser); Xaa at res. 48=(Leu or Ile); Xaa at res. 49=(Val or Met); Xaa at res. 50=(His, Asn or Arg); Xaa at res. 51=(Phe, Leu, Asn, Ser, Ala or Val); Xaa at res. 52=(Ile, Met, Asn, Ala, Val, Gly or Leu); Xaa at res. 53=(Asn, Lys, Ala, Glu, Gly or Phe); Xaa at res. 54=(Pro, Ser or Val); Xaa at res. 55=(Glu, Asp, Asn, Gly, Val, Pro or Lys); Xaa at res. 56=(Thr, Ala, Val, Lys, Asp, Tyr, Ser, Gly, Ile or His); Xaa at res. 57=(Val, Ala or Ile); Xaa at res. 58=(Pro or Asp); Xaa at res. 59=(Lys, Leu or Glu); Xaa at res. 60=(Pro, Val or Ala); Xaa at res. 63=(Ala or Val); Xaa at res. 65=(Thr, Ala or Glu); Xaa at res. 66=(Gln, Lys, Arg or Glu); Xaa at res. 67=(Leu, Met or Val); Xaa at res. 68=(Asn, Ser, Asp or Gly); Xaa at res. 69=(Ala, Pro or Ser); Xaa at res. 70=(Ile, Thr, Val or Leu); Xaa at res. 71=(Ser, Ala or Pro); Xaa at res. 72=(Val, Leu, Met or Ile); Xaa at res. 74=(Tyr or Phe); Xaa at res. 75=(Phe, Tyr, Leu or His); Xaa at res. 76=(Asp, Asn or Leu); Xaa at res. 77=(Asp, Glu, Asn, Arg or Ser); Xaa at res. 78=(Ser, Gln, Asn, Tyr or Asp); Xaa at res. 79=(Ser, Mn, Asp, Glu or Lys); Xaa at res. 80=(Asn, Thr or Lys); Xaa at res. 82=(Ile, Val or Asn); Xaa at res. 84=(Lys or Arg); Xaa at res. 85=(Lys, Asn, Gln, His, Arg or Val); Xaa at res. 86=(Tyr, Glu or His); Xaa at res. 87=(Arg, Gln, Glu or Pro); Xaa at res. 88=(Asn, Glu, Trp or Asp); Xaa at res. 90=(Val, Thr, Ala or Ile); Xaa at res. 92=(Arg, Lys, Val, Asp, Gln or Glu); Xaa at res. 93=(Ala, Gly, Glu or Ser); Xaa at res. 95=(Gly or Ala) and Xaa at res. 97=(His or Arg).

Generic Sequence 8 (SEQ ID NO: 5) includes all of Generic Sequence 7 and in addition includes the following sequence (SEQ ID NO: 8) at its N-terminus:

```
                    Cys Xaa Xaa Xaa Xaa
                     1               5
```

Accordingly, beginning with residue 7, each "Xaa" in Generic Sequence 8 is a specified amino acid defined as for Generic Sequence 7, with the distinction that each residue number described for Generic Sequence 7 is shifted by five in Generic Sequence 8. Thus, "Xaa at res. 2=(Tyr or Lys)" in Generic Sequence 7 refers to Xaa at res. 7 in Generic Sequence 8. In Generic Sequence 8, Xaa at res. 2=(Lys, Arg, Ala or Gln); Xaa at res. 3=(Lys, Arg or Met); Xaa at res. 4=(His, Arg or Gln); and Xaa at res. 5=(Glu, Ser, His, Gly, Arg, Pro, Thr, or Tyr).

In another embodiment, useful osteogenic proteins include those defined by Generic Sequences 9 and 10, defined as follows.

Specifically, Generic Sequences 9 and 10 are composite amino acid sequences of the following proteins: human OP-1, human OP-2, human OP-3, human BMP-2, human BMP-3, human BMP-4, human BMP-5, human BMP-6, human BMP-8, human BMP-9, human BMP10, human BMP-11, *Drosophila* 60A, *Xenopus* Vg-1, sea urchin UNIVIN, human CDMP-1 (mouse GDF-5), human CDMP-2 (mouse GDF-6, human BMP-13), human CDMP-3 (mouse GDF-7, human BMP-12), mouse GDF-3, human GDF-1, mouse GDF-1, chicken DORSALIN, dpp, *Drosophila* SCREW, mouse NODAL, mouse GDF-8, human GDF-8, mouse GDF-9, mouse GDF-10, human GDF-11, mouse GDF-11, human BMP-15, and rat BMP3b. Like Generic Sequence 7, Generic Sequence 9 accommodates the C-terminal six cysteine skeleton and, like Generic Sequence 8, Generic Sequence 10 accommodates the seven cysteine skeleton.

```
                        Generic Sequence 9
                                                  (SEQ ID NO: 6)
        Xaa Xaa Xaa Xaa Xaa Xaa Xaa Xaa Xaa Xaa
         1               5                  10

Xaa Xaa Xaa Xaa Xaa Xaa Pro Xaa Xaa Xaa
                 15                  20

Xaa Xaa Xaa Xaa Cys Xaa Gly Xaa Cys Xaa
                         25                  30

Xaa Xaa Xaa Xaa Xaa Xaa Xaa Xaa Xaa Xaa
                 35                  40

Xaa Xaa Xaa Xaa Xaa Xaa Xaa Xaa Xaa Xaa
                 45                  50

Xaa Xaa Xaa Xaa Xaa Xaa Xaa Xaa Xaa Xaa
                 55                  60

Xaa Cys Xaa Pro Xaa Xaa Xaa Xaa Xaa Xaa
                         65                  70

Xaa Xaa Leu Xaa Xaa Xaa Xaa Xaa Xaa Xaa
                 75                  80
```

```
Generic Sequence 9

Xaa Xaa Xaa Xaa Xaa Xaa Xaa Xaa Xaa Xaa
                         85                              90

Xaa Xaa Xaa Cys Xaa Cys Xaa
                 95
``` wherein each Xaa is independently selected from a group of one or more specified amino acids defined as follows: "Res." means "residue" and Xaa at res. 1=(Phe, Leu or Glu); Xaa at res. 2=(Tyr, Phe, His, Arg, Thr, Lys, Gln, Val or Glu); Xaa at res. 3=(Val, Ile, Leu or Asp); Xaa at res. 4=(Ser, Asp, Glu, Asn or Phe); Xaa at res. 5=(Phe or Glu); Xaa at res. 6=(Arg, Gln, Lys, Ser, Glu, Ala or Asn); Xaa at res. 7=(Asp, Glu, Leu, Ala or Gln); Xaa at res. 8=(Leu, Val, Met, Ile or Phe); Xaa at res. 9=(Gly, His or Lys); Xaa at res. 10=(Trp or Met); Xaa at res. 11=(Gln, Leu, His, Glu, Asn, Asp, Ser or Gly); Xaa at res. 12=(Asp, Asn, Ser, Lys, Arg, Glu or His); Xaa at res. 13=(Trp or Ser); Xaa at res. 14=(Ile or Val); Xaa at res. 15=(Ile or Val); Xaa at res. 16=(Ala, Ser, Tyr or Trp); Xaa at res. 18=(Glu, Lys, Gln, Met, Pro, Leu, Arg, His or Lys); Xaa at res. 19=(Gly, Glu, Asp, Lys, Ser, Gln, Arg or Phe); Xaa at res. 20=(Tyr or Phe); Xaa at res. 21=(Ala, Ser, Gly, Met, Gln, His, Glu, Asp, Leu, Asn, Lys or Thr); Xaa at res. 22=(Ala or Pro); Xaa at res. 23=(Tyr, Phe, Asn, Ala or Arg); Xaa at res. 24=(Tyr, His, Glu, Phe or Arg); Xaa at res. 26=(Glu, Asp, Ala, Ser, Tyr, His, Lys, Arg, Gln or Gly); Xaa at res. 28=(Glu, Asp, Leu, Val, Lys, Gly, Thr, Ala or Gln); Xaa at res. 30=(Ala, Ser, Ile, Asn, Pro, Glu, Asp, Pile, Gln or Leu); Xaa at res. 31=(Phe, Tyr, Leu, Asn, Gly or Arg); Xaa at res. 32=(Pro, Ser, Ala or Val); Xaa at res. 33=(Leu, Met, Glu, Phe or Val); Xaa at res. 34=(Asn, Asp, Thr, Gly, Ala, Arg, Leu or Pro); Xaa at res. 35=(Ser, Ala, Glu, Asp, Thr, Leu, Lys, Gln or His); Xaa at res. 36=(Tyr, leis, Cys, Ile, Arg, Asp, Asn, Lys, Ser, Glu or Gly); Xaa at res. 37=(Met, Leu, Phe, Val, Gly or Tyr); Xaa at res. 38=(Asn, Glu, Thr, Pro, Lys, His, Gly, Met, Val or Arg); Xaa at res. 39=(Ala, Ser, Gly, Pro or Phe); Xaa at res. 40=(Thr, Ser, Leu, Pro, His or Met); Xaa at res. 41=(Asn, Lys, Val, Thr or Gln); Xaa at res. 42=(His, Tyr or Lys); Xaa at res. 43=(Ala, Thr, Leu or Tyr); Xaa at res. 44=(Ile, Thr, Val, Phe, Tyr, Met or Pro); Xaa at res. 45=(Val, Leu, Met, Ile or His); Xaa at res. 46=(Gln, Arg or Thr); Xaa at res. 47=(Thr, Ser, Ala, Asn or His); Xaa at res. 48=(Leu, Asn or Ile); Xaa at res. 49=(Val, Met, Leu, Pro or Ile); Xaa at res. 50=(His, Asn, Arg, Lys, Tyr or Gln); Xaa at res. 51=(Phe, Leu, Ser, Asn, Met, Ala, Arg, Glu, Gly or Gln); Xaa at res. 52=(Ile, Met, Leu, Val, Lys, Gln, Ala or Tyr); Xaa at res. 53=(Asn, Phe, Lys, Glu, Asp, Ala, Gln, Gly, Leu or Val); Xaa at res. 54=(Pro, Asn, Ser, Val or Asp); Xaa at res. 55=(Glu, Asp, Asn, Lys, Arg, Ser, Gly, Thr, Gln, Pro or His); Xaa at res. 56=(Thr, His, Tyr, Ala, Ile, Lys, Asp, Ser, Gly or Arg); Xaa at res. 57=(Val, Ile, Thr, Ala, Leu or Ser); Xaa at res. 58=(Pro, Gly, Ser, Asp or Ala); Xaa at res. 59=(Lys, Leu, Pro, Ala, Ser, Glu, Arg or Gly); Xaa at res. 60=(Pro, Ala, Val, Thr or Ser); Xaa at res. 61=(Cys, Val or Ser); Xaa at res. 63=(Ala, Val or Thr); Xaa at res. 65=(Thr, Ala, Glu, Val, Gly, Asp or Tyr); Xaa at res. 66=(Gln, Lys, Glu, Arg or Val); Xaa at res. 67=(Leu, Met, Thr or Tyr); Xaa at res. 68=(Asn, Ser, Gly, Thr, Asp, Glu, Lys or Val); Xaa at res. 69=(Ala, Pro, Gly or Ser); Xaa at res. 70=(Ile, Thr, Leu or Val); Xaa at res. 71=(Ser, Pro, Ala, Thr, Asn or Gly); Xaa at res. 2=(Val, Ile, Leu or Met); Xaa at res. 74=(Tyr, Phe, Arg, Thr, Tyr or Met); Xaa at res. 75=(Phe, Tyr, His, Leu, Ile, Lys, Gln or Val); Xaa at res. 76=(Asp, Leu, Asn or Glu); Xaa at res. 77=(Asp, Ser, Arg, Asn, Glu, Ala, Lys, Gly or Pro); Xaa at res. 78=(Ser, Asn, Asp, Tyr, Ala, Gly, Gln, Met, Glu, Asn or Lys); Xaa at res. 79=(Ser, Asn, Glu, Asp, Val, Lys, Gly, Gln or Arg); Xaa at res. 80=(Asn, Lys, Thr, Pro, Val, Ile, Arg, Ser or Gln); Xaa at res. 81=(Val, Ile, Thr or Ala); Xaa at res. 82=(1le, Asn, Val, Leu, Tyr, Asp or Ala); Xaa at res. 83=(Leu, Tyr, Lys or Ile); Xaa at res. 84=(Lys, Arg, Asn, Tyr, Phe, Thr, Glu or Gly); Xaa at res. 85=(Lys, Arg, His, Gln, Asn, Glu or Val); Xaa at res. 86=(Tyr, His, Glu or Ile); Xaa at res. 87=(Arg, Glu, Gln, Pro or Lys); Xaa at res. 88=(Asn, Asp, Ala, Glu, Gly or Lys); Xaa at res. 89=(Met or Ala); Xaa at res. 90=(Val, Ile, Ala, Thr, Ser or Lys); Xaa at res. 91=(Val or Ala); Xaa at res. 92=(Arg, Lys, Gln, Asp, Glu, Val, Ala, Ser or Thr); Xaa at res. 93=(Ala, Ser, Glu, Gly, Arg or Thr); Xaa at res. 95=(Gly, Ala or Thr); Xaa at res. 97=(His, Arg, Gly, Leu or Ser). Further, after res. 53 in rBMP3b and mGDF-10 there is an Ile; after res. 54 in GDF-1 there is a T; after res. 54 in BMP3 there is a V; after res. 78 in BMP-8 and Dorsalin there is a G; after res. 37 in hGDF-1 there is Pro, Gly, Gly, Pro.

Generic Sequence 10 (SEQ ID NO: 7) includes all of Generic Sequence 9 (SEQ ID NO: 6) and in addition includes the following sequence (SEQ ID NO: 9) at its N-terminus:

```
                                        SEQ ID NO: 9
Cys Xaa Xaa Xaa Xaa
 1               5
```

Accordingly, beginning with residue 6, each "Xaa" in Generic Sequence 10 is a specified amino acid defined as for Generic Sequence 9, with the distinction that each residue number described for Generic Sequence 9 is shifted by five in Generic Sequence 10. Thus, "Xaa at res. 1=(Tyr, Phe, His, Arg, Thr, Lys, Gln, Val or Glu)" in Generic Sequence 9 refers to Xaa at res. 6 in Generic Sequence 10. In Generic Sequence 10, Xaa at res. 2=(Lys, Arg, Gln, Ser, His, Glu, Ala, or Cys); Xaa at res. 3=(Lys, Arg, Met, Lys, Thr, Leu, Tyr, or Ala); Xaa at res. 4=(His, Gln, Arg, Lys, Thr, Leu, Val, Pro, or Tyr); and Xaa at res. 5=(Gln, Thr, His, Arg, Pro, Ser, Ala, Gln, Asn, Tyr, Lys, Asp, or Leu).

As noted above, certain currently preferred bone morphogenic polypeptide sequences useful in this invention have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the *Drosophila* 60A protein. Accordingly, in certain particularly preferred embodiments, useful morphogenic proteins include active proteins comprising pairs of polypeptide chains within the generic amino acid sequence herein referred to as "OPX" (SEQ ID NO: 3), which defines the seven cysteine skeleton and accommodates the homologies between several identified variants of OP-1 and OP-2. As described therein, each Xaa at a given position independently is selected from the residues occurring at the corresponding position in the C-terminal sequence of mouse or human OP-1 or OP-2.

```
Cys Xaa Xaa His Glu Leu Tyr Val Ser Phe Xaa Asp Leu Gly Trp Xaa Asp Trp
 1           5                  10                  15

Xaa Ile Ala Pro Xaa Gly Tyr Xaa Ala Tyr Tyr Cys Glu Gly Glu Cys Xaa Phe Pro
        20              25              30                  35

Leu Xaa Ser Xaa Met Asn Ala Thr Asn His Ala Ile Xaa Gln Xaa Leu Val His Xaa
        40              45              50                      55

Xaa Xaa Pro Xaa Xaa Val Pro Lys Xaa Cys Cys Ala Pro Thr Xaa Leu Xaa Ala
            60              65              70

Xaa Ser Val Leu Tyr Xaa Asp Xaa Ser Xaa Asn Val Ile Leu Xaa Lys Xaa Arg
75              80              85                  90

Asn Met Val Val Xaa Ala Cyn Gly Cys His
        95              100
``` wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In still another preferred embodiment, useful osteogenically active proteins have polypeptide chains with amino acid sequences comprising a sequence encoded by a nucleic acid that hybridizes, under low, medium or high stringency hybridization conditions, to DNA or RNA encoding reference morphogen sequences, e.g., C-terminal sequences defining the conserved seven cysteine domains of OP-1, OP-2, BMP2, 4, 5, 6, 60A, GDF3, GDF6, GDF7 and the like. As used herein, high stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringence conditions are well characterized in commercially available, standard molecular cloning texts. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984).

As noted above, proteins useful in the present invention generally are dimeric proteins comprising a folded pair of the above polypeptides. Such morphogenic proteins are inactive when reduced, but are active as oxidized homodimers and when oxidized in combination with others of this invention to produce heterodimers. Thus, members of a folded pair of morphogenic polypeptides in a morphogenically active protein can be selected independently from any of the specific polypeptides mentioned above.

The bone morphogenic proteins useful in the materials and methods of this invention include proteins comprising any of the polypeptide chains described above, whether isolated from naturally-occurring sources, or produced by recombinant DNA or other synthetic techniques, and includes allelic and phylogenetic counterpart variants of these proteins, as well as muteins thereof, and various truncated and fusion constructs. Deletion or addition mutants also are envisioned to be active, including those which may alter the conserved C-terminal six or seven cysteine domain, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The bone morphogenic proteins contemplated herein can be expressed from intact or truncated cDNA or from synthetic DNAs in prokaryotic or eukaryotic host cells, and purified, cleaved, refolded, and dimerized to form morphogenically active compositions. Currently preferred host cells include, without limitation, prokaryotes including *E. coli*, or eukaryotes including yeast, or mammalian cells, such as CHO, COS or BSC cells. One of ordinary skill in the art will appreciate that other host cells can be used to advantage. Detailed descriptions of the bone morphogenic proteins useful in the practice of this invention, including how to make, use and test them for osteogenic activity, are disclosed in numerous publications, including U.S. Pat. Nos. 5,266,683 and 5,011,691, the disclosures of which are incorporated by reference herein, as well as in any of the publications recited herein, the disclosures of which are incorporated herein by reference.

Thus, in view of this disclosure and the knowledge available in the art, skilled genetic engineers can isolate genes from cDNA or genomic libraries of various different biological species, which encode appropriate amino acid sequences, or construct DNAs from oligonucleotides, and then can express them in various types of host cells, including both prokaryotes and eukaryotes, to produce large quantities of active proteins capable of stimulating endochondral bone morphogenesis in a mammal.

II. Binding Agent Considerations

As already explained, "binding agent", as used herein, means any physiologically-compatible material which, when admixed with osteogenic protein and matrix as defined herein promotes bone and/or cartilage formation. In certain currently preferred embodiments, binding agents promote such repair using less osteogenic protein than standard osteogenic devices. Among the other characteristics of a preferred binding agent is an ability to render the device: pliable, shapeable and/or malleable; injectable; adherent to bone, cartilage, muscle and other tissues; resistant to disintegration upon washing and/or irrigating during surgery; and, resistant to dislodging during surgery, suturing and post-operatively, to name but a few. Additionally, in a currently preferred embodiment, binding agent can achieve the aforementioned features and benefits when present in relatively low proportions. For example, a currently preferred improved device comprises approximately 1 part binding agent and approximately 5 parts matrix. Another currently preferred device comprises 1 part binding agent and 3 parts matrix. As exemplified herein, improved devices of widely divergent proportions can induce bone and cartilage formation. Exemplified herein are improved devices having parts of binding agent to parts of matrix ranging from approximately 1:1 to 4:1 up to and including at least 10:1, as well as from approximately 1:2 to 1:5, up to and including at least 1:10, and further including 1:25 to 1:50. Any proportion of binding agent to matrix can be used to practice the instant invention. All that is required is admixing binding agent with matrix and osteogenic protein so as to achieve bone and cartilage formation. As discussed below, certain binding agents can be used in equal or greater proportions relative to matrix, but such agents should be tested as taught herein to measure any matrix dilution effects.

Those binding agents contemplated as useful herein include, but are not limited to: art-recognized gelling agents, suspending agents, viscosity-producing agents and emulsifying agents. In particular, art-recognized agents, such as cellulose gum derivatives and sodium alginate, gelatin powder and dextrans can be used. More particularly, cellulosic agents such as alkylcelluloses, including agents such as methylcellulose, methylhydroxyethylcellulose, hydroxyethylcellulose, hydroxypropylmethylcellulose, carboxymethylcellulose, sodium carboxymethylcellulose, and hydroxyalkylcelluloses, to name but a few. Currently among the most preferred is carboxymethylcellulose, including the sodium salt thereof. As exemplified below, other binding agents suitable for use in the instant invention include, but are not limited to, dextran, mannitol, white petrolatum, sesame oil and admixtures thereof.

Finally, also among the most preferred binding agents is a fibrin glue, which comprises a mixture of mammalian fibrinogen and thrombin. As exemplified herein, fibrin glue as a preferred binding agent can comprise wide ranges of fibrinogen and thrombin. In certain embodiments comprising 1 part fibrin glue and 25 parts β-TCP matrix, thrombin content can range from about 2.0 U to 25 U, preferably 5 U to 10 U and most preferably about 2.5 U to 5 U. In certain other devices comprising fibrin glue and collagen matrix, thrombin content can range from about 2.0 U to 25 U; preferably 5 U to 25 U, more preferably 2.0 U to 10 U and most preferably 2.5 U to 5 U. Fibrinogen content can range from about 40 mg per 1000 mg β-TCP, for example. In a collagen-containing improved device, fibrinogen content can range from about 20 mg per 1000 mg collagen to about 180 mg per 1000 mg collagen, for example.

In view of the teachings set forth herein, the artisan can identify suitable equivalents of the above-identified binding agents using merely routine experimentation and ordinary skill. Suitable binding agent candidates can be identified, characterized, tested and then used in osteogenic devices as set forth below.

In general, agents which are recognized in the art as suspending or viscosity-producing agents in pharmaceutical technologies are suitable fox use as a binding agent in the instant invention. Reference manuals such as the USP XXII-NF XVII (*The Nineteen Ninety U.S. Pharmacopeia and the National Formulary* (1990)) categorize and describe such agents. For example, binding agent candidates are those described as useful as emulsifying agents, gel-forming agents, binders, or viscosity-producing agents for injectables and parenterals. Other candidates are agents used to suspend ingredients for topical, oral or parenteral administration. Yet other candidates are agents useful as tablet binders, disintegrants or emulsion stabilizers. Still other candidates are agents used in cosmetics, toiletries and food products. When used for any of the foregoing applications, candidate agents are described as typically present for conventional applications at concentrations ranging from approximately 0.1 to 6.0%. At the highest standard concentrations (4-6%), certain of the foregoing candidate agents are used in the pharmaceutical industry, for example, to produce medicaments in the form of gels or pastes.

Thus the skilled artisan can identify binding agent candidates accordingly and can similarly recognize equivalents of the preferred binding agents specifically identified herein using only routine skill and routine experimentation. Having identified a suitable candidate(s), the skilled artisan can then follow the guidelines set forth below as to final selection of a preferred binding agent.

Based on studies similar to those described herein, examples of suitable binding agents useful in the improved devices disclosed herein include, but are not limited to: mannitol/dextran combination; dextran alone; mannitol/white petrolatum combination; and sesame oil. A mannitol/dextran-containing improved device was formulated as follows. One part dextran 40, 3 parts mannitol, 1 part OP device. Such improved devices were formulated with 2.5 mg osteogenic protein per g collagen or per 0.5 g collagen, thereby varying the dose of osteogenic protein. For use in the instant method, the formulation was wetted with approximately 0.8 ml saline per 2.5 g mannitol/dextran-containing device. Next, a dextran alone-containing device was formulated from either 4 parts dextran or 1 part dextran to 1 part OP device, and wetted with approximately 0.8 ml saline per 2.0 g device. Dextran can range from 3,000 to 40,000 m.w. Next, a mannitol/white petrolatum device was formulated from 1.5 parts mannitol, 1.5 parts petrolatum, and 1 part OP device. This formulation does not require wetting. Finally, a sesame oil-containing improved device was formulated from 1 part oil and 1 part OP device. This formulation does not require wetting. The above-described improved devices illustrate the range of: specific binding agents, proportions in improved devices, and volumes of wetting agent which can be used in the improved devices of the instant invention. Chemistries, proportions and wetting requirements are varied, yet all are within the skill of the art. Each of the aforementioned improved devices induced bone formation (as measured by calcium content and % bone) when tested in the rat subcutaneous bioassay described herein.

A. CMC as a Binding Agent

As taught herein, carboxymethylcellulose (CMC) is a currently preferred binding agent. CMC is commercially available from suppliers such as, but not limited to: Hercules Inc., Aqualon®Division, Delaware; FMC Corporation, Pennsylvania; British Celanese, Ltd., United Kingdom; and Henkel KGaA, United Kingdom. Carboxymethylcellulose sodium is the sodium salt of a polycarboxymethyl ether of cellulose with a typical molecular weight ranging from 90,000-700,000. CMC was identified as a candidate binding agent based, in part, on the following: CMC is widely used in oral and topical pharmaceutical formulations as a viscosity-increasing agent. CMC is also used in cosmetics, toiletries and foods as an emulsifying agent (0.25-1.0%); gel forming agent (4.0-6.0%), injectable (0.05-0.75%), and tablet binder (1.0-6.0%).

While the foregoing characteristics are suggestive of suitability as a binding agent, the experiments detailed below confirmed that CMC was suitable for use in the improved osteogenic devices disclosed herein. Such confirmatory experiments were necessary because none of the aforementioned applications are similar to the repair of bone or cartilage for which the improved osteogenic devices disclosed herein are useful. For example, none of the aforementioned applications require CMC above 6%, yet a currently preferred implantable improved device of the instant invention comprises more than approximately 6% (w/w) CMC and preferably at least approximately 10%, more preferably approximately 12-20%, with approximately about 16% (w/w) or 1 part CMC to 5 parts standard osteogenic device being among the most currently preferred for an implantable device. These approximate percentages are based on calculations of total weight of matrix admixed with binding agent, excluding osteogenic protein and wetting agent.

Of significance to practice of the instant invention is the fact that various grades of carboxymethylcellulose sodium are commercially available which have differing viscosities. Viscosities of various grades of carboxymethylcellulose sodium are reported and shown in Table 1 below (see, *Handbook of Pharmaceutical Excipients* (2nd Edition), American Pharmaceutical Association & Royal Pharmaceutical Society of Great Britain).

TABLE 1

Standard Viscosity Grades of Carboxymethylcellulose

| Grade | Concentration (% w/v) | Viscosity (cP) |
| --- | --- | --- |
| Low viscosity | 4 | 50-200 |
| Medium viscosity | 2 | 400-800 |
| High viscosity | 1 | 1500-3000 |

A number of grades of carboxymethylcellulose are commercially available, the most frequently used grade having a degree of substitution (DS) of 0.7. The DS is defined as the average number of hydroxyl groups substituted per anhydroglucose unit. It is this DS which determines the aqueous solubility of the polymer. The degree of substitution and the standard viscosity of an aqueous solution of stated concentration is indicated on any carboxymethylcellulose sodium labelling. Low viscosity CMC (Aqualon® Division, Hercules Inc., Wilmington, Del.) is currently preferred. The currently preferred degrees of substitution range from 0.65-0.90 (DS=0.7, Aqualon® Type 7L).

As described above, CMC is available in several grades—low, medium and high viscosity. In this regard, the viscosity of the carboxymethylcellulose (CMC) used to formulate an improved osteogenic device was determined to be critical for bone formation. Contrary to teachings in the art, it has now been discovered that high viscosity CMC adversely affects bone formation when used in an improved osteogenic device comprising a matrix as defined herein. U.S. Pat. No. 5,587,897 ("the '897 patent") teaches the use of high viscosity (2480 cP) (see Table 1 above) CMC to induce bone formation. The devices in the '897 patent, however, require a synthetic polymer matrix, rather than a biological matrix such as collagen. Unexpectedly, when a biological material such as collagen is used as a matrix, the improved device must be formulated with low viscosity CMC (approximately 10-50 cP, or 50-200) in order to induce bone and/or cartilage formation, as taught herein.

Toxicity Study Using a CMC Device

A toxicity study was conducted comparing a CMC-containing improved device to that of a standard device. The standard device was prepared with 2.5 mg OP-1/gram collagen matrix. The CMC containing improved device was prepared by adding low viscosity CMC (Aqualon®) to a standard device at the ratio of 1:5 followed by irradiation. 25 mg aliquots of a standard device or mock device (i.e., no osteogenic protein) and 30 mg aliquots of CMC containing improved device or mock CMC device were implanted at a rat sub-cutaneous site as described elsewhere herein (one implant per animal). Three implants from each formulation were removed at 7 days, 14 days, 21 days and 28 days post-implantation, and evaluated histologically for bone and cartilage formation and for local tissue reaction. No adverse cellular reaction was observed, and there was no evidence to indicate any adverse effects of CMC, as determined by evaluating inflammation and fibrous formation. The histological profile of the CMC-containing-improved device was generally similar to the standard OP-device. Serum calcium and alkaline phosphatase levels, measured using standard teachings also followed that of the standard osteogenic device. Finally, using standard toxicity analyses on immature and mature rats, no significant lesions were detected.

Improved Device Bioactivity Studies

Based on a series of routine studies described below, the bioactivity of a standard osteogenic device was not adversely affected by admixture with CMC. Rather, bioactivity is at least comparable for both device configurations, but the ability to manipulate the device intraoperatively and to retain the device at the defect site during surgery and wound closure is enhanced by CMC. For these studies, irradiated CMC was added to the standard device prior to implantation.

Briefly, two studies were conducted measuring the in vivo release of OP-1 from a standard device+/−CMC. In one experiment, 75 mg of irradiated device+/−15 mg of irradiated CMC were implanted in a subcutaneous site in rats as described herein. The implanted devices were removed 1 hour, 1 day, 3 days and 6 days after implantation, followed by extraction with 8M urea buffer; the OP-1 content was analyzed by routine ELISA and western blot analysis. OP-1 device (not implanted into the animals) was extracted with 8M urea buffer and used as the internal standard. In general, the kinetics of in vivo release of OP-1 from the standard OP device and the CMC-containing improved device were similar. The observation that there is no difference in OP-1 sequestration or retention by a standard device versus an improved device containing a combination of collagen matrix and CMC is an unexpected result. It has been reported that, when combined with non-biological polymeric matrices, CMC acts to sequester osteogenic protein. (See, for example, U.S. Pat. No. 5,597,897).

In vitro studies were also conducted. In these studies, released OP-1 was measured in contrast to the above-described in vivo studies, in which OP-1 remaining in the device was measured. In one study, 25 mg of OP device or CMC device was wetted with saline. 1 ml of bovine serum was then added to each device, and the devices were incubated at 37° C. The supernatant was removed and replaced with fresh serum at 1 and 3 hours. At 6 hours 8M urea was added to extract any OP-1 still associated with the device. OP-1 concentrations in the supernatants were analyzed by routine ELISA and western blot techniques. Both the standard OP device and the CMC-containing improved device had similar protein release kinetics for the six hours studied. Again, these results were unexpected in view of earlier reports that CMC acts to sequester osteogenic protein and thereby retard and/or prevent its release from admixtures with synthetic, polymeric matrices. (See, for example, U.S. Pat. No. 5,597,897).

In conclusion, CMC does not substantially inhibit the retention or release of OP-1 from a collagen matrix-containing osteogenic device in vivo or in vitro.

Stability Studies

A study (see Table 2) was conducted comparing the stability of the standard OP device to a standard device containing CMC. Based on both in vitro analyses and a bone-forming bioassay (described elsewhere herein), the CMC-containing improved device was observed to be at least as stable as the standard device when stored at 30 degrees for one year. The data also suggest that CMC can be premixed with the standard OP device and terminally sterilized for a unitary product configuration. Such a unitary product is useful for repair of local bone and cartilage defects as exemplified below.

TABLE 2

Stability Of Various Osteogenic Device Formulations

| Formulation | Pre-Irradiation OP-1 Recovery* | Post-Irradiation OP-1 Recovery | OP-1 Recovery after 4 weeks | OP-1 Recovery after 3 months | OP-1 Recovery after 6 months | OP-1 Recovery after 12 months |
|---|---|---|---|---|---|---|
| Standard Device | 91% | 63% | 66% | 58% | 47.4% | 37.4% |
| CMC Device | 77% | 57% | 53% | 50% | 43.5% | 34.8% |

*Based on theoretical OP-1 content of 2.5 mg/gram

During formulation of a standard device containing CMC, the CMC and osteogenic proteins may be sterilized separately, for example, by exposure to gamma irradiation and then the sterilized components combined to produce the standard device containing CMC. Furthermore, the CMC can be premixed with the standard OP device and the resulting formulation sterilized, for example, by exposure to gamma irradiation. The latter process is referred to in the art as terminal sterilization and has been used to sterilize other osteogenic devices. See, for example, PCT/US96/10377, published as WO 96/40297 on Dec. 19, 1996, and U.S. Pat. No. 5,674,292 issued on Oct. 7, 1997 the disclosures of which are incorporated by reference. As used herein, the terms "sterilization" and "sterilized" refer to a process using either physical or chemical means for eliminating substantially all viable organisms, especially micro-organisms, viruses and other pathogens, associated with the device of the invention. The sterilized devices of the invention preferably have a sterility assurance level of $10^{-6}$ as determined by Federal Drug Administration (FDA) standards. In the case of gamma irradiated devices, for example, the appropriate dosages of irradiation necessary for sterilizing a particular device can be determined readily by consulting the reference text "Associate for the Advancement of Medical Instrumentation Guidelines," published 1992. Guidelines are provided therein for determining the radiation dose necessary to achieve a given sterility assurance level for a particular bioburden of the device. Dosages for sterilizing devices of the invention preferably are within the range of about 0.5 to about 4.0 megarods and most preferably are within the range of about 2.0 to about 3.5 megarods.

Additionally, a study was conducted to evaluate the short term stability of an osteogenic device to which CMC and saline had been added. The study used a standard device to which 200 mg of separately packaged, irradiated CMC was added. Samples of CMC-containing improved device were removed and wet with saline. At 0, 1, 3, 6 and 22 hours the OP-1 was extracted with 8 M urea buffer and analyzed by reverse-phase HPLC under reducing conditions. The extracts were also analyzed for OP-1 biological activity a standard cell-based assay for measuring alkaline phosphatase. The data indicated that OP-1 retains biological activity under these conditions. These data also suggested that the configuration of CMC-containing improved device resulting from admixture of these component parts (standard osteogenic device/CMC/saline) is useable for several hours after it has been prepared, providing the practitioner with significant intraoperative time during which the product remains efficacious.

Testing of Binding Agent Integrity and Other Characteristics

Art-recognized USP methods were used for identification and characterization of bulk binding agents such as CMC. Tests included tests for chemical identity, viscosity, pH, loss on drying and heavy metals. Material was also tested for bioburden prior to sterilization, as well as endotoxins, pH, appearance and sterility after irradiation. A stability study was conducted to monitor the viscosity, appearance and pH of the irradiated material. All levels and characteristics were acceptable as determined using standard methods and techniques.

For example, CMC (Aqualon®-low viscosity) was evaluated for bioburden and endotoxin content. Aqualon® CMC, Lot FP10 12342, was evaluated for the presence of endotoxins (LAL) using the Kinetic Chromogenic LAL assay from BioWhittaker (Walkersville, Md., 21793).

"Bioburden" can be measured as follows. For example 200 mg samples of CMC were solubilized in 100 ml of phosphate buffered water and filtered through 0.45 µm filters. The filters were placed on a TSA plate and incubated for 48 hours. Two samples of solubilized CMC were inoculated with 10-100 CPUs of *Bacillus subtilis* to be used as growth controls. The data suggest that the bioburden of the CMC is low, and that CMC does not interfere in the analysis by killing bacteria or inhibiting cell growth.

CMC Characterization Post-Irradiation

A study was conducted comparing the viscosity of CMC pre- and post-irradiation (gamma irradiation, 2.5-3.0 mega rads). The data indicated that, as reported in the art, viscosity decreases after irradiation. While this does not affect bioactivity or its overall utility as a binding agent (see studies set forth herein), the skilled practitioner should take this feature into consideration when assessing viscosity or fluidity properties of an improved osteogenic device. A study was also conducted to evaluate the stability of irradiated CMC. The results indicated that irradiated CMC was stable for at least six months at both 4 and 30° C. Viscosity was measured as the parameter of stability. Similar analyses and assessments can be carried out for other binding agents or device materials used in a desired formulation.

B. Fibrin Glue as a Binding Agent

As taught herein, "fibrin glue" is another currently preferred binding agent. Fibrin glue comprises a mixture of mammalian fibrinogen and thrombin. Human fibrinogen is commercially available in products such as, but not limited to: Tissucol® (ImmunoAG, Vienna, Austria), Beriplast® (Behringwerke, Marburg, Germany), Biocoll® (Centre de Transfusion Sanguine de Lille (Pours, France) and Transglutine® (CNTS Fractionation Centre, Strasbourg, France). Human thrombin is commercially available from ImmunoAG, Vienna, Austria. Fibrin glue may also be made of fibrinogen and thrombin from other mammalian sources, such as, for example, bovine and murine sources.

Fibrin glue was identified as a candidate binding agent based on its gel-like properties and its improved handling characteristics when admixed with a matrix material, such as, for example, collagen or β-TCP. Fibrin glue was also shown to elicit a low inflammatory response (see below) and to promote bone formation.

Toxicity Study Using a Fibrin Glue Device

A toxicity study was conducted comparing a fibrin glue-containing improved device to that of a standard device. The standard device was prepared by mixing 10 μg OP-1 in 47.5% ethanol/0.01% TFA and 25 mg collagen and lyophilizing the mixture overnight. The standard device was wetted with 100 μL phosphate buffered saline (PBS) prior to implantation. The fibrin glue-containing improved device was prepared by adding 50 μL bovine fibrinogen (Sigma F8630, 10 mg/ml) and 50 μL bovine thrombin (50 U/mL) to the standard device, prepared as described above, immediately prior to implantation. The standard device and the fibrin glue-containing improved device were then implanted at a rat sub-cutaneous site as described elsewhere herein. The implants were evaluated histologically for bone and cartilage formation and for local tissue reaction. The fibrin glue-containing improved device elicited a low inflammatory response and low fibrous formation. The histological profile of the fibrin glue-containing improved device was generally similar to that of the standard device. There did not appear to be any correlation between the inflammatory response and the ability of the fibrin glue-containing improved device to promote bone formation.

Improved Device Bioactivity Studies

A study was done to evaluate the release kinetics of OP-1 from a fibrin glue-containing improved device at different thrombin concentrations in vitro. Release kinetics were improved by the addition of larger amounts of thrombin. For this study, 12.5 μl, of OP-1 in a 5% lactose solution was mixed with 50 mg β-TCP, 25 μL human fibrinogen, and either 25 U/mL of human thrombin or 50 U/mL human thrombin. The mixtures were transferred to a glass vial and 1 mL of calf serum added to each. The samples were then allowed to incubate at 37° C./60 rpm. Serum samples were taken and analyzed by routine ELISA at 0-1 hours, 1-3 hours, 3-5 hours and 5-24 hours. The results are summarized in the table below.

TABLE 2A

| Thrombin conc. | % OP-1 release at 0-1 hours | % OP-1 release at 1-3 hours | % OP-1 release at 3-5 hours | % OP-1 release at 5-24 hours | Total % OP-1 release |
|---|---|---|---|---|---|
| 25 U/mL | 6.4 +/− 0.7 | 5.2 +/− 0.4 | 3.0 +/− 0.6 | 13.0 +/− 0.6 | 27.5 +/− 2.2 |
| 50 U/ml | 9.9 +/− 2.1 | 5.8 +/− 0.7 | 3.3 +/− 0.5 | 15.1 +/− 1.7 | 34.1 +/− 4.8 |

III. Formulation and Delivery Considerations

General Considerations

The devices of the invention can be formulated using routine methods. All that is required is determination of the desired final concentration of osteogenic protein per device, keeping in mind that the delivered volume of device can be, but is not necessarily required to be, less than the volume at the defect site. The desired final concentration of protein will depend on the specific activity of the protein as well as the type, volume, and/or anatomical location of the defect. Additionally, the desired final concentration of protein can depend on the age, sex and/or overall health of the recipient. Typically, for a critical size segmental defect approximately at least 2.5 cm in length, 0.5-1.75 mg osteogenic protein has been observed using the standard device to induce bone formation sufficient to repair the gap. In the case of a non-critical size defect or a fresh fracture, approximately 0.1-0.5 mg protein has been observed using the standard osteogenic device to repair the defect. In general, protein concentrations for use with preferred matrices described herein can range from about 0.4 mg to about 3.0 mg per device. Optimization of dosages requires no more than routine experimentation and is within the skill level of one of ordinary skill in the art.

As exemplified herein, osteogenic protein and a binding agent such as carboxymethylcellulose (low viscosity, Aqualon®) or fibrin glue can be admixed to form a putty. In some embodiments, saline is added to binding agent to form a paste or putty in which an osteogenic protein such as OP-1 is dispersed. A paste configuration can be used to paint the surfaces of a defect, such as a cavity. Pastes can be used to paint fracture defects, chondral or osteochondral defects, as well as bone defects at a prosthetic implant site. A more fluid configuration can be injected or extruded into or along the surfaces of a defect, in a manner similar to extruding toothpaste or caulking from a tube, such that a bead of device is delivered along the length of the defect site. Typically, the diameter of the extruded bead is determined by the type of defect as well as the volume of the void at the defect site.

As mentioned above, other binding agents as defined herein can be used to formulate a device with a configuration like putty. As will be obvious to the skilled artisan, such a configuration results from adjusting the proportion of carrier to wetting agent, with less wetting agent producing a drier device and more producing a wetter device. The precise device configuration suitable to repair a defect will at least depend on the type of defect and the size of the defect. The skilled artisan will appreciate the variables.

A. CMC as a Binding Agent—Formulation Studies

Based on the following type of studies, it was established that approximately 0.2 g of CMC to approximately 1.0 g standard osteogenic device yields an improved device with the currently preferred handling properties. Varying ratios of CMC and collagen were combined and then wet with saline. Each resulting mixture of CMC and matrix was suspended in a 15 ml conical centrifuge tube of water and placed on a rotary shaker (100 rpm). Settling time was recorded when loosened or released collagen matrix particles settled to a predetermined mark on the tube. The data summarized in Table 3 and FIG. 1 suggest that a range of approximately 0.15 to 0.25 g CMC/g collagen can maximize cohesiveness, integrity and handling properties.

TABLE 3

Effect Of CMC/Collagen Ratio On Dispersion Time

| g CMC/g Collagen | Settling Time |
|---|---|
| 0.20 g | 19 min |
| 0.19 | 17 |
| 0.18 | 6 |
| 0.15 | 4 |
| 0.12 | 0.5 sec |

Figure 2:
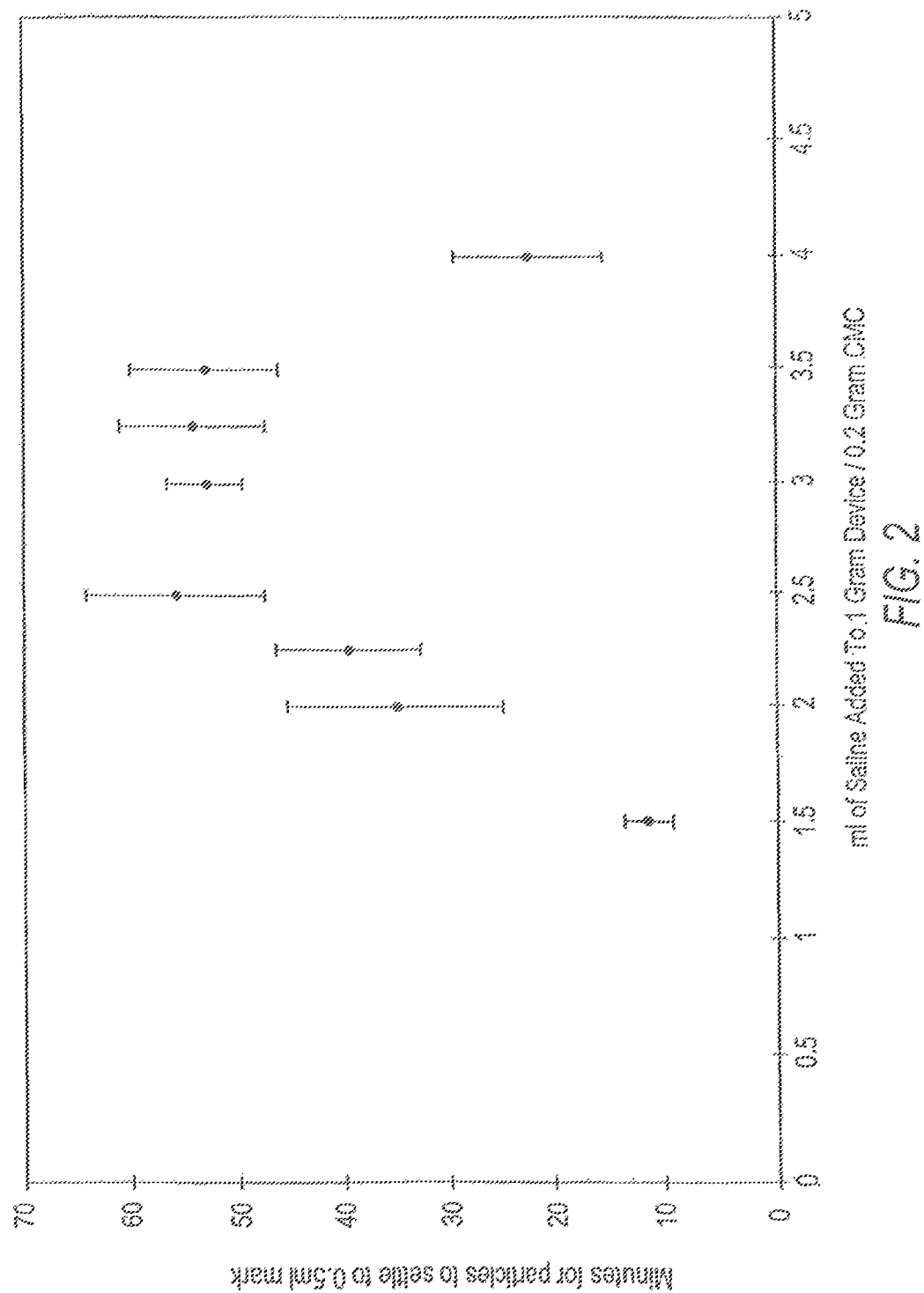
FIG. 2 is a graph depicting the effect of varying volumes of wetting agent on the integrity of an improved osteogenic device.

The preferred amount of saline for wetting the CMC device was also studied. In this study, approximately 0.2 g of CMC were mixed with approximately 1 g standard osteogenic device. Varying amounts of saline were added, and the consistency of the resulting device was noted. The qualitative and quantitative results from this study are summarized in Table 4 and FIG. 2, respectively. Generally, these data illustrate that there is a range of wetting agent volumes which can accommodate the practitioner while enabling the device to retain its integrity and cohesiveness. For a binding agent like CMC, the data suggest that more than approximately 1.5 ml, approximately 1.8 to 2.5 ml of saline, is the currently preferred wetting volume (for approximately 1 gram of device admixed with approximately 200 mg of a binding agent such as CMC) to achieve an implantable device with the currently preferred putty consistency. Amounts of saline in excess of this achieve an injectable device with the currently preferred fluid consistency. As exemplified elsewhere herein, an implantable device configuration is suitable for use at an open defect site, while an injectable device configuration is suitable for use at a closed defect site. In terms of gram equivalents, approximately 0.5 g to approximately 3.0 g saline has been determined to yield improved devices with desirable consistencies; the higher the weight, the more injectable is the configuration.

TABLE 4

Wetting of the CMC-Containing Device

| 1 gram Standard Device plus 200 mg CMC | | |
|---|---|---|
| | Amount of Saline Added | Observations |
| | 1.5 ml | Dry |
| | 1.75 | Rolls into a ball; paste |
| | 2.0 | Currently preferred handling consistency; putty. Rolls into a ball. |
| | 2.5 | Acceptable handling consistency; still putty-like. |
| | 2.75 | Leaves small particles of matrix on vessel wall. |
| | 3.0 | Sticky; soft paste. |
| | 3.5 | Sticky; soft paste. |
| | 3.75 | Loose paste. |
| | 4.0 | Consistency same as above. |
| | 4.25 | Liquid |

In certain embodiments of the present invention, preparation of the actual improved osteogenic device can occur immediately prior to its delivery to the defect site. As exemplified herein, CMC-containing improved devices can be prepared on-site, suitable for admixing immediately prior to surgery. In one embodiment, low viscosity CMC (Aqualone) was packaged and irradiated separately from the osteogenic protein. OP-1 and collagen matrix. The OP-1 protein in collagen matrix then was admixed with the binding agent. Devices prepared in this manner were observed to be at least as biologically active as the standard device without CMC.

B. Fibrin Glue as a Binding Agent—Formulation Studies

Based on the following type of studies, it was established that approximately 500 μL fibrinogen (80 mg/mL in PBS at pH 7.4) and 500 μL thrombin (50 U/mL or 25 U/mL in 0.9% NaCl) added to approximately 1 μm of β-TCP yields an improved device with the currently preferred handling properties. Issues related to handling properties include the clotting time of the fibrin glue and the consistency of the fibrin glue-containing improved device. A device having a consistency of a moldable putty is preferred. Once the glue clots, it becomes more difficult to change the shape of the putty. A longer clotting time is, therefore, also a preferred feature of the device.

The clotting time of bovine fibrin glue was determined by mixing 20 μL bovine fibrinogen solution (80 mg/mL in PBS at pH 7.4) with 20 μL bovine thrombin solution (500 U/mL or 25 U/mL in saline) continuously in a weight boat using a capillary glass rod. The clotting times were also evaluated with or without addition of 0.6% $CaCl_2$ solution. The results are shown in the following table:

TABLE 4A

| Thrombin (U/mL) | Clotting time in seconds w/o $CaCl_2$ | Clotting time in seconds with 0.6% $CaCl_2$ |
|---|---|---|
| 500 | 23 +/− 2 | 20 +/− 2 |
| 250 | 40 +/− 5 | 29 +/− 2 |
| 100 | 61 +/− 2 | 49 +/− 1 |
| 50 | 90 +/− 2 | 74 +/− 1 |
| 25 | — | 185 +/− 5 |

The consistency of the fibrin glue-containing device was evaluated using a device containing β-TCP as an exemplary matrix. Differing amounts of bovine fibrin glue were added to 100 mg or 1000 mg of β-TCP granules and the consistency determined. The results are summarized in the table below:

TABLE 4B

| Amount of β-TCP | Fibrinogen μL (80 mg/mL in PBS, pH 7.4) | Thrombin μL | Consistency |
|---|---|---|---|
| 100 mg | 12.5 | 12.5 (100 U/mL in saline w/0.6% $CaCl_2$) | β-TCP not wetted completely |
| 100 mg | 25 | 25 (100 U/mL in saline w/0.6% $CaCl_2$) | slightly moldable |
| 100 mg | 50 | 50 (100 U/mL in saline w/0.6% $CaCl_2$) | putty, moldable at 1-2 min. |
| 100 mg | 50 | 50 (50 U/mL in saline w/0.6% $CaCl_2$) | moldable putty |
| 100 mg | 50 | 50 (5 U/mL in saline w/0.6% $CaCl_2$) | clotting very slow, particles separated |
| 1000 mg | 500 | 500 (100 U/mL in saline w/0.6% $CaCl_2$) | mixing too slow, inhomogenous, particles separated |
| 1000 mg | 500 | 500 (50 U/mL in saline) | putty, moldable at 1-2 min. |
| 1000 mg | 500 | 500 (25 U/mL in saline) | putty, moldable at 2-3 min. |

As can be seen by these two studies, a fibrin glue-containing device of approximately 500 μL fibrinogen (80 mg/mL in PBS at pH 7.4) and 500 μL thrombin (50 U/mL or 25 U/mL in 0.9% NaCl) added to approximately 1 μm of β-TCP has a clotting time and consistency suitable for the improved osteogenic device.

Rat Sub-Cutaneous Study

In the study set forth below, β-TCP (Clarkson, #211096, BD=0.86, 212-425 μm, 9/6/97) is formulated in a CMC/blood paste with or without 10 μg OP-1 and implanted into rat subcutaneous sites. The implants are removed after 6 and 12 weeks in vivo and analyzed using the image analysis method described above. Results at six weeks are summarized in Table 4D below. Results indicate that after six weeks the size of β-TCP decreases from 334 μm to 184 μm (without OP-1) and to 166 μm (with OP-1). The difference in size between OP-1 treated and non-treated samples is not significant. However, there is about 50% reduction in the diameter of the β-TCP after six weeks.

TABLE 4C

Representative Information Relating to the Composition of Fibrin Glue

|  | Autocolle ® | Tissucol ® | Beriplast ® | Transglutine ® | Biocoll ® |
|---|---|---|---|---|---|
| Fibrinogen (mg/mL) | 50-65 | 70-110 | 20-140 | >70 | 116 +/− 2.4 |
| Fibronectin (mg/mL) | 4-10 | 2-9 |  |  | 5.9 +/− 0.51 |
| Factor XIII (PEU) | 25-30 | 10-50 | 40-60 |  | 35 +/− 2.88 |
| Thromboglobulin (μg/mL) | 250-400 |  |  |  |  |
| PDGF (ng/mL) | 350 |  |  |  |  |
| TGF (ng/mL) | 750 |  |  |  |  |
| Plasminogen (μg/mL) |  | 40-120 |  |  | 31 |
| Aprotinin (KIU/mL) |  | 3000 |  |  |  |
| Albumin (mg/mL) |  |  |  | 10 |  |

1. Autocolle ® and Biocoll ® are from Centre de Transfusion Sanguine de Lille (Tours, France)
2. Tissucol ® is from Immuno AG (Vienna, Austria)
3. Beriplast ® is from Behringwerke (Marburg, Germany)
4. Transglutine ® is from CNTS Franctionation Centre (Strasbourg, France)

Based on the above-described studies, it was established that approximately 40 mg fibrin glue to approximately 1000 mg β-TCP yields an improved device as contemplated herein. Based on the same studies, it was established that approximately 20 mg fibrin glue to approximately 1000 mg collagen yields a device with the preferred properties set forth herein. Generally, the data suggest that a range of approximately 20-220 mg fibrin glue/1000 mg matrix can maximize cohesiveness, integrity and handling properties, depending on the precise circumstances and intended use.

IV. Other Materials Considerations

In certain embodiments of the invention, the preferred matrix material is β-TCP. Preferred characteristics of a non-synthetic, non-polymeric material for use as a matrix in the claimed invention include, but are not limited to: a high rate of resorption of the matrix by the surrounding tissue and a low inflammatory response. As discussed above, sintered, high fired β-TCP having particle sizes ranging from about 212 μm to about 425 μm are currently most preferred, but other particle sizes can be used to practice the instant invention.

Image Analysis Method

The rate of resorption of the β-TCP matrix was determined using a standard image analysis method. Image analysis is a method of evaluating the particle size distribution of Ca/P granules. The particle size of Ca/P granules is compared before and after implantation in rats. The soft tissues of the explants are dissolved by sodium hypochlorite, and the remaining Ca/P granules are washed several times with water and dried at room temperature. The particles are mixed with glycerol and mounted onto glass slides. Particle size is determined by microscopy using a standard image analysis system, such as Bioquant OS/2 linked by a video camera to the microscope. Arrays denoting the area and the longest diameter are selected to express the individual particle dimensions. Image of the particles showing gray scale of 0 to 88 on a 256-level set were chosen and measured. The raw data from individual particles are used to calculate the mean and standard deviation. At least 50 particles are measured in each data set.

TABLE 4D

IN VIVO RESORPTION OF β-TCP AT 6 WEEKS

| Samples (n = 4) | time in vivo | OP-1 (μg) | Particle size (μm) | Particle area (mm²) |
|---|---|---|---|---|
| β-TCP/CMC/Blood | 6 weeks | 0 | 184 +/− 29 | 0.022 +/− 0.008 |
| β-TCP/CMC/Blood | 6 weeks | 10 | 166 +/− 22 | 0.016 +/− 0.004 |
| β-TCP alone (212-425 μm) | 0 | — | 334 +/− 16 | 0.068 +/− 0.007 |

TABLE 4E

Source and Composition of Some Preferred Matrix Materials and Preferred Components of Fibrin Glue.

| Item | Source | Composition |
|---|---|---|
| Ca/P particles | Clarkson Chromatography Products, Inc. (S. Williamsport, PA) | Range from 50-2000 μm, for example, hydroxyapatite $(Ca_{10}(PO_4)_6(OH)_2)$ or β-TCP $(Ca_3(PO_4)_2)$ |
| Bovine Fibrinogen | Sigma (F8630) (St. Louis, MO) | 75% protein, 10% sodium citrate, 15% NaCl |
| Human Thrombin | Immuno AG (Vienna, Austria) | 500 U or 4U per vial, reconstituted in 2 mL 40 mM $CaCl_2$ |
| β-TCP granules | Clarkson Chromatography Products, Inc. (S. Williamsport, PA) | Range from 50-2000 μm, composition is $(Ca_3(PO_4)_2)$ |

TABLE 4E-continued

Source and Composition of Some Preferred Matrix Materials and Preferred Components of Fibrin Glue.

| Item | Source | Composition |
| --- | --- | --- |
| Calf serum | Life Technologies (16170-078) (Gaithersburg, MD) | n.a. |
| bovine thrombin | Sigma (T4648) (St. Louis, MO) | 50-100 U/mg protein |
| Rat thrombin | Sigma (T5772) (St. Louis, MO) | 1000 U/mg protein |
| Rat Fibrinogen | Sigma (F6755) (St. Louis, MO) | 70% protein, 12% sodium citrate, 18% NaCl |

Inflammation

In general, it can be assumed that small particles will be resorbed faster than large particles. Results indicated that, without OP-1, β-TCP (212-425 μm) elicited a slightly elevated inflammatory response. However, the inflammatory reaction was reduced as the dose of OP-1 increases from 10 μg to 20 μg. Previous animal studies have shown that small particles, less than 10 μm elicit a high inflammatory response. Therefore, use of sintered p-TCP (100%) particles of the size of 212 to 425 μm is a balance between resorption rate, low inflammation, and ability to support bone formation in the rat subcutaneous model.

V. Bioassay

A. Bioassay of Osteogenic Activity: Endochondral Bone Formation and Related Properties The following sets forth exemplary protocols for identifying and characterizing bona fide osteogenic or bone morphogenic proteins as well as osteogenic devices within the scope of Applicants' invention.

The art-recognized bioassay for bone induction as described by Sampath and Reddi (Proc. Natl. Acad. Sci. USA (1983) 80:6591-6595) and U.S. Pat. No. 4,968,590, the disclosures of which are herein incorporated by reference, is used to establish the efficacy of the purification protocols. Briefly, this assay consists of depositing the test samples in subcutaneous sites in allogenic recipient rats under ether anesthesia. A vertical incision (1 cm) is made under sterile conditions in the skin over the thoracic region, and a pocket is prepared by blunt dissection. In certain circumstances, approximately 25 mg of the test sample is implanted deep into the pocket and the incision is closed with a metallic skin clip. The heterotropic site allows for the study of bone induction without the possible ambiguities resulting from the use of orthotopic sites.

The sequential cellular reactions occurring at the heterotropic site are complex. The multistep cascade of endochondral bone formation includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

In rats, this bioassay model exhibits a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoblastic and bone remodeling on days twelve to eighteen; and (8) hematopoietic bone marrow differentiation in the ossicle on day twenty-one.

Histological sectioning and staining is preferred to determine the extent of osteogenesis in the implants. Staining with toluidine blue or hemotoxylin/eosin clearly demonstrates the ultimate development of endochondral bone. Twelve day bioassays are sufficient to determine whether bone inducing activity is associated with the test sample.

Additionally, alkaline phosphatase activity can be used as a marker for osteogenesis. The enzyme activity can be determined spectrophotometrically after homogenization of the excised test material. The activity peaks at 9-10 days in vivo and thereafter slowly declines. Samples showing no bone development by histology should have no alkaline phosphatase activity under these assay conditions. The assay is useful for quantitation and obtaining an estimate of bone formation very quickly after the test samples are removed from the rat. For example, samples containing osteogenic protein at several levels of purity have been tested to determine the most effective dose/purity level, in order to seek a formulation which could be produced on an industrial scale. The results as measured by alkaline phosphatase activity level and histological evaluation can be represented as "bone forming units". One bone forming unit represents the amount of protein that is needed for half maximal bone forming activity on day 12. Additionally, dose curves can be constructed for bone inducing activity in vivo at each step of a purification scheme by assaying various concentrations of protein. Accordingly, the skilled artisan can construct representative dose curves using only routine experimentation.

B. Cartilage Formation: Immunohistochemistry Histology and Polarized Light Microscopy 1. Immunohistochemistry and Histology.

Briefly, it is well known in the art that identification of bona fide articular cartilage can be accomplished using ultrastructural and/or biochemical parameters. For example, articular cartilage forms a continuous layer of cartilage tissue possessing identifiable zones. The superficial zone is characterized by chondrocytes having a flattened morphology and an extracellular network which does not stain, or stains poorly, with toluidine blue, indicating the relative absence of sulphated proteoglycans. Toluidine blue is commonly used for the staining of bone and cartilage. It is a metachromatic stain that yields different colors based on the presence of densely spaced negative charges in the tissues leading to the aggregation and polymerization of the dye which shifts the color from blue to purple. Bone is stained blue whereas the cartilage, with its acidic mucopolysaccharides, is stained a dark purple. Chondrocytes in the mid and deep zones have a spherical appearance, and the matrix contains abundant sulphated proteoglycans, as evidenced by staining with toluidine blue. Collagen fibers are present diffusely throughout the matrix. The chondrocytes possess abundant rough endoplasmic reticulum and are surrounded by an extracellular network. The pericellular network contains numerous thin, non-banded collagen fibers. The collagen in the interterritorial network is less compacted and embedded in electron translucent amorphous material, similar to articular cartilage. Collagen fibers in the interterritorial region of the network exhibit the periodic banding characteristic of collagen fibers in the interterritorial zone of cartilage tissue.

Von Kossa staining shows a dense black staining of the mineralized tissue This stain clearly depicts the existing and newly regenerated bone through the deposition of silver on the calcium salts. Typically, the counter stain is Safranin O, which stains the cartilage red-orange. New and existing bone can usually be easily distinguished morphologically in sections stained accordingly. Safranin O/Fast Green is able to distinguish more features than the Toluidine blue. Safranin O is a basic dye that stains the acidic mucopolysaccharides in the articular cartilage red-orange and the underlying subchondral bone only lightly. Fast Green is an acidic dye that stains the cytoplasm gray-green. Stain is not only able to clearly identify the existing and regenerated cartilage, but can also distinguish differences between two regions in the reparative tissue indicating differences in the content of proteoglycans.

Hematoxylin/eosin stains which depict bone a darker red and the carbohydrate rich cartilage only very lightly, can also be used. Masson Trichrome is able to distinguish differences in the reparative tissue. Cartilage and acidic polysaccharide-rich reparative tissue, muscle, and erythrocytes are stained red, with the collagen of the bone stained blue.

Histological evaluations can also involve assessment of: glycosaminoglycan content in the repair cartilage; cartilage and chondrocyte morphology; and, structural integrity and morphology at the defect interface. The morphology of repair cartilage can be identified by the type of cartilage formed: articular vs. fibrotic by evaluating glycosaminoglycan content, degree of cartilage deposition, and the like.

Histological evaluations using standard methodologies well characterized in the art also allows assessment of new bone and bone marrow formation. See, for example, U.S. Pat. No. 5,266,683, the disclosure of which is incorporated herein by reference.

Additionally, it is well known in the art that biochemically, the presence of Type. II and Type IX collagen in the cartilage tissue is indicative of the differentiated phenotype of chondrocytes. The presence of Type II and/or Type IX collagen can be determined by standard gel electrophoresis, Western blot analysis and/or immunohisto-chemical staining using, for example, commercially available antibody as described below. Other biochemical markers include hematoxylin, eosin, Goldner's Trichrome and Safranin-O.

Immunohistochemical methods, such as the following, can be utilized to identify formation of cartilage tissue, including articular cartilage. Tissue sections are prepared using routine embedding and sectioning techniques known in the art. Epitopes for Type II collagen are first exposed by protease pretreatment. For example, tissue specimens are pretreated with 1 mg/ml pronase type XIV from Sigma (St. Louis, Mo.; catalog number. P5147) in tris-buffered saline (TBS) for approximately 10 min at room temperature. Specimens are then washed in TBS with 0.2% glycine. Specimens are blocked for 30 min, in a tris-buffered saline solution containing 1% Tween 20 (TBST) and bovine serum albumin (BSA), and washed with TBST. Specimens are then incubated with affinity purified polyclonal goat anti-human collagen Types I and II antibodies for approximately 1 hr, or overnight, at room temperature. In certain of the Examples set forth below, goat anti-human Type I collagen antibody was obtained from Southern Biotechnology Associates (Birmingham, Ala.), catalog number 1310-01, for example, lot number L055-X916; goat anti-human Type II collagen antibody was also obtained from Southern Biotechnology Associates, catalog number 1320-01, for example, lot number C153-T826. Anti-human Types I and II collagen antibodies generated in mouse or rabbit can also be used. The skilled artisan will appreciate the circumstances under which use of one species versus another is appropriate. For certain of the examples set forth below, the concentrations of goat anti-human Types I and II collagen antibodies used for incubation is, for example, 20 µg/ml for each antibody diluted into 1% BSA in TBST. After incubation with antibodies, the specimens are rinsed with TBST and held in a bath. A commercially available link antibody is then added. For example, specimens treated with goat anti-human collagen Types I and II antibodies can be incubated with goat-link antibody from BioGenex Laboratories (San Ramon, Calif.); catalog number HK209-5G) for at least 10 min at room temperature. For those samples incubated with mouse or rabbit antibodies, a Dako LSAB2 kit number K0610 from Dako Corporation (Carpinteria, Calif.) can be used as the link antibody. The specimens are again rinsed with TBST and held in a bath. Next, the specimens are allowed to incubate with Strepavidin/Alkaline Phosphatase commercially available from any of the above-identified sources for at least approximately 10 min at room temperature. The specimens are again rinsed with TBST. The specimens are then developed by treatment with an appropriate substrate solution for approximately 10 min or less. For example, for alkaline phosphatase detection, approximately 100 µl of 50× lavamesole is used. For color development, Fast Red from Dako Corporation is used. After development, the specimens are counterstained by washing for 2 min with Harris hematoxylin and 1% lithium carbonate. The specimens are then mounted in an aqueous mounting media, and cartilage formation is subsequently evaluated.

Staining for types I and II collagen is useful to determine the boundary between regenerated subchondral bone and reparative tissue. Generally, reparative tissue that is fibrous stains less intensely. Additionally, newly formed subchondral bone can be identified by type II collagen localization in small spicules of remnant cartilage. Toluidene blue and Safranin-O are also useful for staining acidic proteoglycans in a cartilage layer as well as reparative tissues.

2. Polarized Light Microscopy

Polarized light microscopy can be used to assess fibril interdigitation at the junction between the margins of repair tissue and the residual articular cartilage adjacent to the defect. Such microscopy can be performed using Safranin-O stained sections from a defect. In certain instances, polarized light microscopy offers the skilled artisan a more accurate view of the repair process. For example, using light microscopy, repair tissue at the periphery of a defect can appear well apposed with the residual cartilage. Using polarized light microscopy, however, it can be observed that the collagen fibrils of the repair tissue are not well integrated with those of the residual cartilage. Lack of fibril continuity between repair and persisting cartilage is indicative of sub-optimal repair.

Thus, when evaluating qualitatively the interface between repair cartilage and residual viable cartilage, fibrillar continuity is preferably assessed using polarized light microscopy as exemplified herein below. (See, also, Shapiro et al., *Journal of Bone and Joint Surgery* 532-553 (1993), the disclosure of which is herein incorporated by reference.)

Practice of the invention will be still more fully understood from the following examples, which are presented herein for illustration only and should not be construed as limiting the invention in any way.

VI. Animal Studies: Methods of Use of Improved Osteogenic Devices

A. Repair of Critical Size Segmental Defects Using Improved Osteogenic Devices Containing Carboxymethylcellulose 1. Experiment 1: Unitary Device Configuration (Dogs)

This study illustrates the efficacy of OP-1 combined with collagen matrix and carboxymethylcellulose for repairing critical-size ulna segmental defects in the art-recognized canine model.

Briefly, the data set forth below indicate at least comparable radiographic healing at sites that received a CMC/OP-1 device relative to segmental defects treated with the standard OP device. The final radiographic grade (maximum=6.0) for defects treated with CMC/OP-1 was 5.33±0.58 compared to 4.67±0.58 for defect receiving the standard OP-1 device. In general, new bone formation was evident as early as two weeks post-operative in all defects. The new bone continued to densify, consolidate and remodel until sacrifice at twelve post-operative weeks. The mean load to failure of the defects treated with the CMC/OP-1 device was 59.33 N±26.77. This was 70% of the mean load to failure of the contralateral sides which received the standard OP-1 implants. Histologically, the final volume, quality and degree of remodelling were at least equivalent in defects treated with the CMC/OP-1 and standard OP-1 device, although a variation in the final new bone formation and degree of remodelling was noted in animal to animal comparisons. The mean histologic grade for defects treated with the CMC/OP-1 device was 12.67±1.04 out of 16 total possible points. The mean histologic grade for defects treated with the standard OP-1 device was 11.41±0.95 out of 16 total possible points.

Test Device Description

As already described, standard devices consisted of recombinant human osteogenic protein-1 (rhOP-1) admixed with bovine bone Type I collagen matrix at a ratio of 2.5 mg rhOP-1 per gram of collagen matrix. The improved device consisted of rhOP-1 admixed with bovine bone Type I collagen matrix and carboxymethylcellulose (CMC). The unitary devices were supplied in sterile vials.

As earlier-described, the currently preferred CMC-containing device for open defects has a putty consistency. The unitary CMC/OP-1 device was placed dry into a small bowl and mixed with saline. Using fingers, the practitioner mixed and formed the device into the general shape of the defect and then placed the device into the defect site. It was reported that the improved device was more easily handled and shaped, and did not stick to the surgical gloves. The device maintained its integrity when placed in the defect during irrigation and during/after suturing.

Experimental Design

Adult male mongrel dogs were utilized because of their well-known bone repair and remodeling characteristics. All animals were at least two years old and weighed from 40 to 50 pounds. All animals were supplied by Martin Creek Kennels, USDA number 71-B-108, Willowford, Ak. Special attention was paid in selecting animals of uniform size and weight to limit the variability in bone geometry and loading. The animals were radiographically screened pre-operatively to ensure proper size, skeletal maturity, and that no obvious osseous abnormalities existed.

A total of 3 adult male dogs were utilized. Bilateral 2.5 cm ulna segmental defects were created. All right side defects received the improved device (CMC/OP-1 device). All left side defects received standard OP-1 device. Biweekly radiographs were taken to study the progression of healing and graded on a 0-6 scale. At sacrifice, all ulnae were retrieved en bloc, and those that were healed sufficiently upon manual manipulation were mechanically tested in torsion. Segments were evaluated by histology for tissue response, bone architecture and remodelling, and quality and amount of new bone formation and healing; grading was on a 0-16 scale.

Surgery

Using standard aseptic techniques, surgery was performed under halothane gas anesthesia. A lateral incision approximately 4.0 cm in length was made and exposure of the ulna was obtained using blunt and sharp dissection. A 2.5 cm segmental osteoperiosteal defect was created in the mid-ulna using an oscillating saw. This defect was about 2-2.5 times the mid-shaft diameter, and represents a critical size defect, i.e., the defect would not heal spontaneously. Intra-operative measurements were made of the removed bone segment. The radius was maintained for mechanical stability, but no internal or external fixation was used. The site was irrigated with saline to remove bone debris and spilled marrow cells. After the site was dried and homeostasis was achieved, the implants were carefully placed into the defects. The soft-tissues were meticulously closed in layers to contain the implant. The procedure was then repeated on the contralateral side.

Radiographs

Radiographs of the forelimbs were obtained biweekly until eight weeks post-operative and then again at sacrifice at twelve post-operative weeks. Standardized exposure times and intensities were used, and sandbags were used to position the extremities in a consistent manner. Radiographs were evaluated and compared to earlier radiographs to appreciate quality and speed of defect healing. Grading of radiographs was in accordance with the following scale:

TABLE 5

Radiographic Grading Scale

| | Grade: |
|---|---|
| No change from immediate post-operative appearance | 0 |
| Trace of radiodense material in defect | 1 |
| Flocculent radiodensity with flecks of calcification | 2 |
| Defect bridged at least one point with material of non-uniform radiodensity | 3 |
| Defect bridged on both medial and lateral sides with material of uniform radiodensity, cut end of the cortex remain visible | 4 |
| Same as grade 3; at least one of four cortices is obscured by new bone | 5 |
| Defect bridged by uniform new bone; cut ends of cortex are no longer distinguishable | 6 |

Sacrifice

At the end of the study period, animals were sacrificed using an intravenous barbiturate overdose. The ulna and radius were immediately harvested en bloc and placed in saline soaked diapers. Both ulna were macrophotographed and contact radiographs with labels were taken. Soft tissues were carefully dissected away from the defect site. A water-cooled saw was used to cut the ulna to a uniform length of 9 cm with the defect site centered in the middle of the test specimen.

Mechanical Testing

Immediately after sectioning, if healing was deemed sufficient by manual manipulation, specimens were tested to failure in torsion using routine procedures on an MTS closed-loop hydraulic test machine (Minneapolis, Minn.) operated in stroke control at a constant displacement rate of 50 mm/min. Briefly, each end of the bone segment was mounted in a cylindrical aluminum sleeve and cemented with methylmethacrylate. One end was rigidly fixed and the other was rotated counterclockwise. Since the dog ulna has a slight curvature, the specimens were mounted to keep specimen rotation coaxial with that of the testing device. The torsional force was applied with a lever arm of 6 cm, by a servohydraulic materials testing system. Simultaneous recordings were made of implant displacement, as measured by the machine stroke controller, while load was recorded from the load cell. Force-angular displacement curves were generated from which the torque and angular deformation to failure were obtained, and the energy absorption to failure computed as the area under the load-displacement curve.

Histology

The individual specimens were fixed by immersion in 10% buffered formalin solution immediately following mechanical testing or after sectioning in untested specimens. On a water cooled diamond saw the specimens were divided by bisecting the specimen down its long axis. This procedure, resulted in two portions of each specimen for different histologic preparations, including undecalcified ground sections and undecalcified microtome sections.

Following fixation, the specimens designated for undecalcified sections were dehydrated in graduated ethyl alcohol solutions from 70% to 100%. The specimens were then placed in methylmethacrylate monomer and allowed to polymerize. The ground sections were obtained by cutting the specimens on a high speed, water cooled Mark V CS600-A (Grandby, Conn.) sectioning saw into sections approximately 700 to 1,000 μm thick. Sections were mounted on acrylic slides and ground to 100 μm thickness using a metallurgical grinding wheel, and microradiographs were made using standardized techniques. Following microradiography, the sections were further ground to approximately 50 μm and stained with basic fuchsin and toluidine blue for histologic grading that evaluated the following parameters of repair: quality of the union, the appearance and quality of the cortical and cancellous bone, the presence of bone marrow elements, bone remodelling, and inflammatory response. Grading of histologic parameters was in accordance with the following scale:

TABLE 6

Histologic Grading Scale

| | Grade: |
|---|---|
| Quality of Union: | |
| no sign of fibrous or other union | 0 |
| fibrous union | 1 |
| osteochondral union | 2 |
| bone union | 3 |
| bone union with reorganization of cortices | 4 |
| Cortex Development: | |
| none present in the defect | 0 |
| densification of borders | 1 |
| recognizable formation | 2 |
| intact cortices but not complete | 3 |
| complete formation of normal cortices | 4 |
| Residual Implant Material/Internal Architecture: | |
| large amounts of implant material visible | 0 |
| moderate amount of residual implant material | 1 |
| small amount of residual implant material/unorganized architecture | 2 |
| no residual implant/return of marrow cavity/some marrow elements | 3 |
| normal marrow elements and architecture | 4 |
| Inflammatory Response: | |
| severe | 0 |
| severe/moderate | 1 |
| moderate response | 2 |

TABLE 6-continued

Histologic Grading Scale

| | Grade: |
|---|---|
| mild | 3 |
| no response | 4 |
| TOTAL POINTS | 16 |

Results

Radiographic Evaluation

In this study, there were no significant differences in the radiographic bone healing characteristics of sites that received a CMC/OP-1 device as compared to segmental defects treated with the standard OP device. In general, new bone formation was evident as early as two weeks post-operative in all defects. The new bone continued to densify, consolidate and remodel until sacrifice at twelve post-operative weeks. New cortex development with early medullary cavity formation occurred between the 6 and 8 week evaluations. The final radiographic grade for defects treated with the CMC/OP-1 device was 5.33±0.58. The final radiographic grade for defects receiving the standard OP-1 device was 4.67±0.58.

As an example, specific representative observations for one of the test animals are set forth below:

Right Defect (CMC/OP-1 Device)

At two weeks post-operative, traces of radiodense material were present in the right defect, but, the defect was not completely bridged or filled with new bone. By four weeks post-operative, the amount and radiodensity of the new bone significantly increased. The defect was spanned, but, the new bone was not well contained. There was some consolidation of new bone along the periosteal borders. An equivalent amount of new bone had formed compared to the left defect of this animal. At six weeks post-operative, the radiodensity of the new bone increased and the defect was completely spanned and filled with extensive new bone. Early remodelling was evident with the host bone ends beginning to incorporate with the new bone. At eight weeks post-operative, new bone continued to remodel and the new bone volume better approximated the defect borders. The host bone ends were incorporated with the new bone with densification of new bone along the borders suggestive of new cortex formation. There was no radiographic evidence of any residual carrier material. At sacrifice a radiolucent region was present within the center of the right side defect, but, densification of the new bone borders was suggestive of new cortex formation. The final radiographic grade was 5 out of 6 possible points.

Left Defect (OP-1 Device)

At two weeks post-operative, traces of radiodense material were present in the defects, but, the defect was not bridged or filled with new bone. At four weeks post-operative, the amount and radiodensity of the new bone significantly increased and the defect was spanned and filled with new bone. At six weeks post-operative, the radiodensity of the new bone increased and the defect was completely spanned and filled with extensive new bone. Early remodelling was evident, and the new bone volume better approximated the defect borders. The new bone was uniformly dense, and the host bone ends were beginning to incorporate. At eight weeks post-operative new bone continued to remodel, the host bone ends were incorporated, and densification of the new bone had begun along the defect borders. At sacrifice densification of the new bone along the defect borders was suggestive of early reformation of new cortices. The density of the new bone within the center of the defect was greater than new bone that had formed in the right side defect, although there were no significant differences in the radiographic appearances of the right and left sides in this animal. The final radiographic grade was 5 out of 6 possible points.

Gross Observations

Both right and left specimens from all animals had similar gross appearances. In two animals, the right and left defects were firmly united and had approximately the same volume of new bone. In a third animal, both the right and left side had a similar new bone volume, but, the left side was not completely united.

Mechanical Testing

The mean load to failure for defects treated with the CMC/OP-1 device was 59.33 N±26.77 (n=3). The mean load to failure was 79% of the mean load to failure of the contralateral sides, which received the standard OP-1 devices. This represented 91% of the strength of intact controls tested previously. The mean angular deformation was 38.22±0.69 degrees. The mean energy absorbed to failure was 97.47±47.21 Nm degrees.

The mean load to failure of the defects treated with the standard OP-1 device was 75.39 N±1.88 (n=2). This represented 115% of the strength of intact controls tested previously. The mean angular deformation was 59.06±27.80 degrees. The mean energy absorbed to failure was 93.40±17.49 Nm degrees. As noted, one defect treated with the standard OP-1 device was not tested due to gross instability.

Histology

In general, normal bone formation consistent with defects treated with the standard rhOP-1 device with a collagen matrix were observed. Both final volume and quality and degree of remodelling were equivalent in comparison of CMC/OP-1 and standard OP-1 devices. A variation in the final new bone formation and degree of remodelling was noted in animal to animal comparisons. The mean histologic grade for defects treated with the CMC/OP-1 device was 12.67±1.04 out of 16 total possible points. The mean histologic grade for defects treated with the standard OP-1 device was 11.41±0.95 out of a total of 16 possible points.

Generally, both the left and right defects were spanned by a large volume of new bone. The new bone was beginning to reorganize and had lamellar characteristics. Along the defect borders, the new bone became more dense and was suggestive of new cornices. In certain instances, remodelling was not as uniformly advanced on the left as the right side. The volume of new bone on the left side was slightly less than on the right in certain instances. At the center of all the defects, the return of medullary components was evident.

In conclusion, improved osteogenic devices (unitary configuration) were used to repair critical size segmental defects. Rates of endochondral bone repair, mechanical strength indicia, radiographic indicia and histological indicia suggested improved devices result in defect repair at least comparable to standard osteogenic devices.

2. Experiment 2: OP-1 Dose Response Using Non-unitary Device Configuration (Dogs)

This study further illustrates the efficacy of standard osteogenic device admixed with carboxymethylcellulose (CMC) using both standard and low OP-1 dose formulations to heal large, critical size segmental defects in the canine ulna segmental defect model.

As described in detail below, various dosages of OP-1 were employed in this study. Briefly, the low dose formulations of the OP-1 device without CMC were found effective at inducing new bone formation, but less so than the standard dose OP-1 device. However, and unexpectedly, defects treated with the low dose CMC-containing device demonstrated earlier and larger volumes of new bone formation compared to the low dose OP-1 device without CMC. The standard or low dose OP-1 device was prepared by combining a 1 g OP-1 device with 3.2 ml sterile saline. The standard or low dose OP-1 device containing CMC was prepared by combining 1 g OP-1 device with 0.2 g CMC and approximately 2 ml sterile saline. The devices were prepared intra-operatively. Radiographically, standard dose OP-1 treated sites with and without CMC had similar radiographic appearances. Standard dose OP-1 sites had earlier and greater volumes of new bone formation compared to the low dose sites. Histologic results demonstrated more advanced segmental bone defect healing in sites treated with the CMC-containing device compared to the standard OP-1 device. Sites treated with low dose OP-1 device containing CMC achieved an equivalent degree of remodeling and incorporation with the host bone relative to sites treated with the standard dose OP-1 device, but, the volume of new bone induced was less. Defect sites treated with standard dose device containing CMC obtained the greatest mean torsional load to failure at twelve weeks post-operative compared to all other treatment groups (61.91±35.37 N, 95% of the torsional strength of intact controls). The torsional strength of the low dose device containing CMC sites was similar to the standard OP-1 device, having 78% of the strength of intact ulnae and 99% of the strength of previously tested sites treated with the standard device. In contrast, the torsional strength of the low dose OP-1 sites without CMC was only 44% of the torsional strength of intact ulnae and 56% of previously tested segmental defects treated with the standard OP-1 device.

Test Material

The standard OP-1 device (designated OP in Table 11) consisted of recombinant human osteogenic protein-1 (rhOP-1) admixed with bovine bone Type I collagen matrix at a ratio of 2.5 mg rhOP-1/g of collagen matrix. One CMC device (standard dose, designated OP-1/CMC, OPCMC in Table 11) consisted of an OP-1 device combined with carboxymethylcellulose. The low dose OP-1 device consisted of 1.25 mg rhOP-1/g of collagen matrix (designated LOP in Table 10). Each OP-1 device in both standard and low dose consisted of 1 g of device packaged separately from CMC. CMC was packaged 200 mg per vial. This is in contrast to the unitary device described above wherein CMC was co-packaged with the other components of collagen matrix and osteogenic protein.

Experimental Design

A total of 12 adult mongrel dogs were utilized. Bilateral 2.5 cm critical size ulna segmental defects were created. The right side defects of six animals received the standard OP-1 device. The left side defects of this group received the standard dose OP-1/CMC devices. The second group of six animals received the low dose OP-1 devices in the right side defect and received low dose OP-1/CMC devices in the left side defects. Biweekly radiographs were taken to study the progression of healing. At sacrifice, all were retrieved in bloc and mechanically tested in torsion. Ulna segments were evaluated by histology for tissue response, residual implant, and quality and amount of new bone formation and healing.

Animal Model

As described above, adult male mongrel dogs were utilized because of their anatomical size, and known bone repair and remodeling characteristics. All animals were skeletally mature and weighed from 35 to 50 pounds.

Surgery

Using standard surgical techniques similar to those described above, a lateral incision approximately 4 cm in length was made and exposure of the ulna was obtained using blunt and sharp dissection. A 2.5 cm segmental osteoperiosteal defect was created in the mid-ulna using an oscillating saw. This defect was about 2-2.5 times the mid-shaft diameter, and represented a critical-sized defect, i.e., the defect would not heal spontaneously. Intra-operative measurements were made of the removed bone segment. The length of the segment, the two outer diameters of the segment, and the central diameter of the segment was recorded in millimeters in the surgical records. The radius was maintained for mechanical stability. The site was irrigated with saline to remove bone debris and spilled marrow cells. After the site was dried and homeostasis was achieved, the implants were placed in the defect. The soft-tissues were closed in layers to contain the implant. The procedure was then repeated on the contralateral side.

Radiographs

As described above, radiographs of the forelimbs were obtained biweekly until eight weeks post-operative and then again at sacrifice at twelve post-operative weeks.

Sacrifice

Procedures were similar to these described above. At the end of the study period, animals were sacrificed, the ulna and radius immediately harvested en bloc and placed in saline soaked diapers. Soft tissues were carefully dissected away from the defect site. A band saw was used to cut the ulna to a uniform length of 9 cm with the defect site centered in the middle of the test specimen.

Mechanical Testing

Protocols were similar to those described above. Briefly, specimens were tested to failure in torsion on an MTS closed-loop hydraulic test machine (Minneapolis, Minn.) operated in stroke control at a constant displacement rate of 50 mm/min. Torsional force was applied with a lever arm of 6 cm, by a servohydraulic materials testing system. Simultaneous recordings were made of implant displacement, as measured by the machine stroke controller, while load was recorded from the load cell. Force-angular displacement curves were generated from which the torque and angular deformation to failure were obtained, and the energy absorption to failure was computed as the area under the load-displacement curve.

Histology

As described above, fixed specimens designated for undecalcified sections were dehydrated in graduated ethyl alcohol solutions from 70% to 100%. The specimens were then placed in methylmethacrylate monomer and allowed to polymerize. The ground sections were obtained by cutting the specimens on a high speed, water cooled sectioning saw into sections approximately 700 to 1,000 µm thick. These sections were mounted on acrylic slides and ground to 100 µm thickness. Following routine microradiography, the sections were further ground to approximately 50 µm and stained with basic fuchsin and toluidine blue for histologic grading that evaluated the following parameters of repair: quality of the union, the appearance and quality of the cortical and cancellous bone, the presence of bone marrow elements, bone remodeling, and inflammatory response.

Radiographic Evaluation

At twelve weeks post-operative (sacrifice), the standard dose OP-1/CMC sites achieved the greatest mean radiographic grade, 5.17/6.0 points. The final radiographic grade for the standard OP-1 devices was 5.00/6.0. The low dose OP-1 sites had a mean final radiographic grade of 3.83/6.0. Low dose OP-1/CMC sites had a mean grade of 4.67/6.0. At all time periods the standard dose OP-1/CMC sites had greater mean radiographic grades than standard OP-1 without CMC. At all time periods the low dose OP-1 CMC sites had greater mean radiographic grades than low dose OP-1 without CMC sites.

Statistical analysis demonstrated a significant effect for implant type when all radiographic grades were combined (Kruskal-Wall is one way analysis of variance, p=0.0049). Multiple comparisons demonstrated that the standard OP-1 and the standard dose OP-1/CMC devices mean radiographic grades for all time periods were significantly greater than the low dose OP-1 sites without CMC (at $\alpha=0.10$ and at $\alpha=0.05$, respectively). Multiple comparisons also demonstrated that the mean radiographic grade of the standard dose OP-1/CMC sites was significantly greater than the low dose OP-1/CMC sites ($\alpha=0.10$). However, and unexpectedly, the standard dose OP-1 devices mean radiographic grades were not significantly greater than the mean radiographic grades for the low dose OP-1/CMC sites.

Low Dose OP-1 Sites without CMC

At two weeks post-operative, new bone formation was evident in one of six defects treated with low dose OP-1. Traces of radiodense material were present around the defect, but new bone did not bridge or span the defect. The mean radiographic grade at two week post-operative was 0.17/6.0 points. At four weeks post-operative, the same site demonstrating new bone formation at two weeks demonstrated an increase in new bone volume. Four defects were spanned and one defect was filled with new bone at four weeks. Two sites demonstrated little activity at four weeks post-operative. The mean radiographic grade at four weeks was 1.83/6.0. By six weeks post-operative, two sites treated with low dose OP-1 were spanned and filled with new bone. Two sites were spanned but incompletely filled with new bone. One animal demonstrated some early new bone formation. One animal did not demonstrate any new bone formation. The mean radiographic grade at six weeks was 2.83/6.0. From six to eight weeks additional new bone formation was not evident, but, some densification of new bone was apparent and some early remodeling had occurred. The mean radiographic grade at eight weeks was 3.17/6.0. At sacrifice, twelve weeks post-operative, all defects demonstrated some well contained new bone, but, the density was significantly less than the surrounding host bone. Occasional radiolucencies at the host bone new bone junction were present. The mean radiographic grade at twelve weeks was 3.83/6.0.

Low Dose OP-1/CMC Sites

At two weeks post-operative, early new bone formation was evident in three of six defects treated with low dose OP-1/CMC. New bone did not span or fill the defects, but was well contained within the surgical sites. The mean radiographic grade at two weeks was 0.83/6.0. At four weeks post-operative, new bone formation was present in five of six defects, spanning and almost filling the defects. The mean radiographic grade at four weeks was 2.33/6.0. At six weeks the density of new bone present in the defects increased. Early incorporation of the host bone was evident in three of six defects. One animal did not demonstrate any new bone formation bilaterally at six weeks. The mean radiographic grade at this time was 3.00/6.0. From six to eight weeks, no additional new bone formation occurred. Early remodeling and incorporation with the host bone was apparent. One animal did not demonstrate any changes in radiographic appearance. The mean radiographic grade at eight weeks was 3.33/6.0. Unexpectedly, the low dose OP-1/CMC sites demonstrated more extensive new bone formation and remodeling than the low dose OP-1 sites without CMC. In sites where the defect was completely filled with new bone, the density of the new bone was less than the surrounding host bone. The mean radiographic grade at twelve weeks (sacrifice) was 4.67/6.0.

Standard OP-1 Device Sites

The results in this study were consistent will all previous studies of the standard OP-1 device. At two weeks post-operative, four of six defects treated with the OP-1 device demonstrated early new bone formation. In two defects, extensive new bone spanned the defects, but, new bone did not fill the defects. Overall, the new bone was not well contained. The mean radiographic grade at two weeks was 1.50/6.0. At four weeks post-operative, an increase in the amount and density of new bone occurred in all six defects. New bone spanned all defects. In four of six sites the defect appeared completely filled with new bone. The mean radiographic grade at four weeks was 3.00/6.0. At six weeks post-operative, the density of new bone increased. New bone was not well contained in the remaining defects. Generally, early incorporation at the host bone ends was observed in three of the six sites. The mean radiographic grade at six weeks was 3.67/6.0. From six to eight weeks, nearly complete incorporation with the host bone was evident in three of six sites, although remodeling toward the ulna contours had occurred in all defects. The mean radiographic grade at eight weeks was 4.50/6.0. By twelve weeks post-operative (sacrifice) extensive remodeling had occurred, although the new bone volume did not yet approximate the ulna contours. New bone often extended into the surrounding soft tissues, although some reformation of cortices was apparent in all defects treated with the standard OP-1 device. The mean radiographic grade at twelve weeks was 5.00/6.0.

Standard Dose OP-1/CMC Sites

At two weeks post-operative, early new bone formation was evident in four of six defects treated with OP-1/CMC device. New bone was well contained in only one of the four defects. New bone appeared to span and fill two of the six defects. The mean radiographic grade at two weeks was 1.67/6.0. At four weeks post-operative, extensive new bone had occurred in all six defects. New bone was not well contained, but, early incorporation with the host bone was observed in two sites. The mean radiographic grade at four weeks was 1.67/6.0. From four to six weeks, extensive remodeling and incorporation of the host bone occurred in all defects. New bone was not well contained, but, new bone in the soft tissue had begun to resorb. The mean radiographic grade at six weeks was 4.33/6.0. By eight weeks, complete incorporation with the host bone was appreciated in two sites, and early new cortex formation was evident in at least one site. The mean radiographic grade at eight weeks was 4.67/6.0. At twelve weeks post-operative (sacrifice), three of six defects had extensive incorporation with the host bone ends. New bone was still present outside of the defects, although extensive remodeling had occurred. The mean radiographic grade at twelve weeks was 5.17/6.0.

Gross Observations

Sites treated with low dose implants with and without CMC demonstrated less new bone volume compared to the high dose OP-1 sites with and without CMC. All high dose sites were firmly united grossly, but three of twelve sites treated with low dose OP-1 were not yet firmly united at sacrifice.

Low Dose OP-1 Sites without CMC

In all cases, the amount of new bone formed did not exceed the original defect volume. New bone formation was well contained, although in two of six segments the bone was not completely united.

Low Dose OP-1/CMC Sites

Similar to defects treated with low dose OP-1, new bone formation was well contained. One of six sites treated with low dose OP-1/CMC was not completely united. Typically, new bone volume was less than the original defect volume.

Standard OP-1 Device Sites

Similar to previous studies, new bone volume in sites treated with the standard OP-1 device was 2 to 3 times greater than the original defect volume. All defects were firmly united. In five of six defects, extensive new bone extended into the soft tissues and was fused to the radius. In one defect, the volume of new bone formed was less than other sites.

Standard Dose OP-1/CMC Sites

New bone volume in five of six defects treated with OP-1/CMC exceeded the original host bone volume and extended into the soft tissues. The new bone volume was 2 to 3 times the volume of the original defect. As noted above in one animal, reduced bone volume was observed bilaterally.

Mechanical Testing

Mechanical testing summaries appear in Tables 7 and 8.

Unexpectedly, defect sites treated with the standard dose OP-1/CMC device obtained the greatest mean torsional load to failure at twelve weeks post-operative compared to all other treatment groups, including the standard device group. The mean load to failure was 61.91±35.37 N (n=6). This represented 95% of the torsional strength of previously tested intact ulnae and 121% of the strength of previously tested segmental defects treated with the standard OP-1 device. The standard OP-1 device treated sites had a mean torsional strength of 55.84±37.26 N (n=6), 86% of previously tested intact control ulnae, and 110% of previously tested segmental defects treated with the OP-1 device. The mean load to failure for the low dose OP-1/CMC sites was 50.66±31.68 N (n=5), or 78% of the strength of intact control ulnae and 99% of the strength of previously tested segmental defects treated with the standard OP-1 device. The mean load to failure for the low dose OP-1 sites was 28.72±14.71 N (n=4). This represented 44% of the torsional strength of previously tested intact control ulnae and 56% of previously tested segmental defects treated with the standard OP-1 device.

Unexpectedly, paired t-tests of the failure load within animals demonstrated a significant effect for implant type when comparing low dose OP-1 standard devices to low dose OP-1/CMC devices (p=0.0597). The paired mean load for low dose OP-1 sites was 28.72±14.71 (4). The paired mean load to failure for the low dose OP-1/CMC sites was 62.89±18.47 (4). No significant difference was found in paired t-tests of mean load to failure standard OP-1 devices compared to the mean load to failure standard dose OP-1/CMC device.

Histology

Unexpectedly, the sites treated with the standard dose OP-1/CMC device achieved the greatest mean histologic score, 12.08/16.0 points. The low dose OP-1/CMC sites achieved a score of 11.07/15.0, slightly greater than the mean histologic score for the standard OP-1 device sites, 10.88/16.0. The mean histologic grade for the low dose OP-1 sites was 9.58/16.0 points.

Statistical analysis of the mean histologic grades by treatment group demonstrated a significant effect for implant type (Kruskal-Wallis one way analysis of variance, p=0.0282). Multiple comparisons of group means demonstrated that the

TABLE 7

Mechanical Testing Results

| Animal Number | side | Implant Type | Load to Failure | Torque (Nm) | % Intact Controls (%) | Angulation (degrees) | Energy absorbed to failure (NmDegrees) |
|---|---|---|---|---|---|---|---|
| H19 | Right | LOP | 35.17 | 2.11 | 53.88 | 36.74 | 53.93 |
| H21 | Right | LOP | 9.76 | 0.59 | 14.95 | 66.64 | 16.96 |
| H24 | Right | LOP | * | | * | * | * |
| H26 | Right | LOP | 25.75 | 1.55 | 39.45 | 41.33 | 44.42 |
| H30 | Right | LOP | * | | | * | * |
| H34 | Right | LOP | 44.18 | 2.65 | 67.69 | 25.35 | 41.51 |
| | | MEAN | 28.72 | 1.72 | 43.99 | 42.52 | 39.21 |
| | | STANDARD DEVIATION | 14.71 | 0.88 | 22.53 | 17.43 | 15.75 |
| | | SAMPLE SIZE | 4 | 4 | 4 | 4 | 4 |
| H19 | Left | LOPCMC | 39.76 | 2.39 | 60.92 | 37.13 | 55.84 |
| H21 | Left | LOPCMC | 57.51 | 3.45 | 88.11 | 52.47 | 59.47 |
| H24 | Left | LOPCMC | 1.74 | 0.10 | 2.67 | 5.54 | 0.34 |
| H26 | Left | LOPCMC | 82.33 | 4.94 | 126.14 | 37.85 | 120.58 |
| H30 | Left | LOPCMC | * | * | * | * | |
| H34 | Left | LOPCMC | 71.94 | 4.32 | 110.22 | 42.47 | 127.67 |
| | | MEAN | 50.66 | 3.04 | 77.61 | 35.09 | 72.78 |
| | | STANDARD DEVIATION | 31.68 | 1.90 | 48.54 | 17.62 | 52.46 |
| | | SAMPLE SIZE | 5 | 5 | 5 | 5 | 5 |

TABLE 8

Mechanical Testing Results

| Animal Number | side | Implant Type | Load to Failure | Torque (Nm) | % Intact Controls (%) | Angulation (degrees) | Energy absorbed to failure (NmDegrees) |
|---|---|---|---|---|---|---|---|
| H22 | Right | OP | 65.44 | 3.93 | 100.26 | 52.95 | 139.25 |
| H23 | Right | OP | 2.73 | 0.16 | 4.18 | 15.90 | 8.91 |
| H25 | Right | OP | 52.78 | 3.17 | 80.86 | 31.36 | 70.65 |
| H28 | Right | OP | 27.24 | 1.63 | 41.73 | 53.04 | 49.49 |
| H32 | Right | OP | 79.68 | 4.78 | 122.08 | 19.33 | 57.83 |
| H33 | Right | OP | 107.14 | 6.43 | 164.15 | 29.3 | 98.59 |
| | | MEAN | 55.84 | 3.35 | 85.54 | 33.65 | 70.79 |
| | | STANDARD DEVIATION | 37.26 | 2.24 | 57.08 | 16.08 | 44.52 |
| | | SAMPLE SIZE | 6 | 6 | 6 | 6 | 6 |
| H22 | Left | OPCMC | 76.52 | 4.59 | 117.24 | 44.86 | 150.86 |
| H23 | Left | OPCMC | 6.53 | 0.39 | 10.10 | 68.10 | 10.66 |
| H25 | Left | OPCMC | 50.22 | 3.01 | 76.94 | 43.94 | 69.48 |
| H28 | Left | OPCMC | 100.44 | 6.03 | 153.88 | 40.9 | 177.13 |
| H32 | Left | OPCMC | 43.82 | 2.63 | 67.14 | 40.2 | 70.58 |
| H33 | Left | OPCMC | 93.93 | 5.64 | 143.91 | 43.96 | 156.09 |
| | | MEAN | 61.91 | 3.71 | 94.85 | 46.99 | 105.80 |
| | | STANDARD DEVIATION | 35.37 | 2.12 | 54.19 | 10.51 | 65.21 |
| | | SAMPLE SIZE | 6 | 6 | 6 | 5 | 6 |

*Specimen was not tested mean total grade for the standard dose OP-1/CMC sites was significantly greater than the low dose OP-1 without CMC sites (at $\alpha=0.05$).

Statistical analysis of the grade for quality of union also demonstrated a significant effect for implant type. Unexpectedly, the mean quality of union grade for the standard dose OP-1/CMC sites (3.5/4.0) was again significantly greater than the low dose OP-1 sites (2.0/4.0, at $\alpha=0.05$). No significant differences were found for implant type when comparing mean grades for cortex development, residual implant, and inflammatory response.

Low Dose OP-1 Sites without CMC

New bone formation was apparent in all defects treated with low dose OP-1, but the amount of new bone within the defect often did not fill the defect and was not continuous with the host bone ends. In one site the defect completely united histologically. New bone was in the early stages of organization and remodeling. Some areas of newly mineralizing bone were also evident.

Low Dose OP-1/CMC Sites

The low dose OP-1/CMC sites had a similar histologic appearance compared to the low dose OP-1 sites. However, and unexpectedly, new bone was continuous with the host bone more frequently in the low dose OP-1/CMC sites compared to the low dose OP-1 sites. In cases where the bone was continuous with the host bone, early remodeling and densification of the new bone borders was apparent. In cases where new bone healing was not complete, areas of newly mineralizing bone were apparent, as well as areas of fibrous tissues within the defect. In general, the new bone was well contained. Some areas of advanced remodeling along the defect borders was observed.

Standard OP-1 Device Sites

Extensive new bone formation bridged all defects. Early densification of the new bone borders had occurred. In some cases, areas of newly mineralizing bone joined areas of mature bone. At the center of the defects, occasional small areas of residual carrier material was present. No inflammatory response was observed. New bone often extended into the soft tissues. Remodeling was most advanced at the defect/new bone borders. The bone had remodeled to a lamellar structure in these areas.

Standard Dose OP-1/CMC Sites

There were no marked differences in the histologic appearance between the standard OP-1 sites and the standard dose OP-1/CMC sites. Extensive new bone spanned and filled the defects. The most extensive remodeling occurred at the new bone/host bone borders. The remodeled bone had a lamellar structure in these areas. Densification of new cortices was evident, but not yet complete. Occasional small amounts of trapped residual carrier material surrounded by new bone formation were observed. There was no associated, inflammatory response.

Conclusion

Improved osteogenic devices unexpectedly induced earlier and larger volumes of new bone formation at low doses of OP-1 than were induced by standard devices at low doses of OP-1. Moreover, and unexpectedly, defect sites treated with improved osteogenic devices achieved the greatest mean torsional load to failure at twelve-weeks post-operative. Histologically, improved devices unexpectedly achieved the greatest mean score and more frequently demonstrated continuous new bone with host bone.

B. Repair of Non-Critical Size Segmental Defects Using Improved Osteogenic Devices Containing Carboxymethylcellulose 1. Experiment 1: Time Course of Repair of Closed Defect as Treated With a Unitary Device (Dogs)

This non-critical size gap study was conducted to evaluate injectable configurations of improved osteogenic devices. The study design used the 3 mm gap at 4 week model. The study evaluated the healing of the defect after injection of OP-1/CMC/collagen matrix configuration. The contralateral arm of each animal was a control. In addition, a healing time course for an untreated defect was evaluated at 4, 8 and 12 weeks.

The details of the protocol used are summarized below.

Test System

Adult mongrel dogs (18) bred for purpose were utilized in this study because of their anatomical size and known bone repair and remodeling characteristics. The animals were approximately 2 to 4 years old at onset of study and weighed 20 to 30 kg (approximately). The animals were radiographically screened to ensure proper size, skeletal maturity, and that no obvious osseous abnormalities exist.

Test Material Description

Improved osteogenic device formulations comprising recombinant human osteogenic protein-1 (rhOP-1) in a collagen matrix admixed with CMC were tested. Controls consisted of mock device alone.

Formulation 1: 0.350 mg rhOP-1 in 100 µl CMC gel (7%) w/o collagen matrix

Formulation 2: 0.350 mg rhOP-1 in 100 µl acetate/lactose buffer

Formulation 3: 0.350 mg rhOP-1 in 170 mg collagen-CMC matrix wetted with saline

Control 1: 0 mg rhOP-1 in 100 µl gel

Control 2: 0 mg rhOP-1 in 100 µl acetate/lactose buffer

Control 3: 0 mg rhOP-1 in 170 mg collagen-CMC matrix wetted with saline

Experimental Design

Bilateral 3 mm ulna segmental defects were created in all animals. Nine animals received one of the three experimental test formulations in the right side defect, such that three sites of each type were studied. The left defect was implanted with mock device. These animals were sacrificed at four weeks post-operative. The remaining nine animals received non-implanted defects bilaterally and were sacrificed at periods at four, eight, and 12 weeks (three at each time period). As discussed above, radiographs were taken to study the progression of healing. Final determination of sacrifice dates of the nine animals receiving rhOP-1 formulations was based upon the weekly radiographs. At sacrifice, all ulnae were retrieved en bloc and mechanically tested in torsion. Segments were evaluated by histology, as described above, for tissue response, and quality and amount of new bone formation, and extent of healing.

Using standard surgical techniques, a lateral incision approximately two centimeters in length was made, and exposure of the ulna was obtained using blunt and sharp dissection. The 3 mm defect was created in the right mid-ulna using an oscillating saw. The radius was maintained for mechanical stability, but no internal or external fixation was used. The soft-tissues were meticulously closed in layers around the defect. The rhOP-1 sample or mock device was then injected into the site as per the treatment schedule. The procedure was then repeated on the contralateral side with the appropriate sample.

Radiographs of the forelimbs were obtained weekly until six weeks post-operative and then biweekly until 12 weeks in the surviving animals. One additional x-ray was obtained from the remaining animals at sacrifice at twelve weeks post-operative. Radiographs were graded by the investigator on a 0-6 grading scale and compared to earlier radiographs to appreciate quality and speed of defeat healing.

Testing Procedures

As discussed above, the animals were sacrificed at the designated times, and the ulna and radius were immediately harvested en bloc. Both ulna were macrophotographed and contact radiographs taken. Soft tissues were meticulously dissected away from the defect site. A water-cooled saw was used to cut the ulna to a uniform length of 9 cm with the defect site centered in the middle of the test specimen. Immediately after sectioning, the specimen was tested in torsion to failure on an MTS closed-loop hydraulic test machine (Minneapolis, Minn.), as described above.

Both tested and untested specimens were prepared for histologic evaluation, as already described above. Following microradiography, the sections were further ground to approximately 50 μm and stained with basic fuchsin and toluidine blue for histologic evaluation of parameters of repair including: the quality of the union, the appearance and quality of the cortical and cancellous bone, and the inflammatory response.

Descriptive statistics of mechanical testing, radiographic grading and histology were evaluated to characterize healing.

Results

The following observations and representative data were collected to date (4 weeks post-operative):

Mechanical testing summaries appear in Tables 9, 10 and 11. Table 11 is a summary of control subjects in previous, unrelated experiments. Generally and overall, the results of this study indicate that animals treated with OP-1 exhibit accelerated healing. The OP-1 treated defects healed in one-third to one-half the time of untreated controls. Additionally, and unexpectedly, the CMC/OP-1/collagen formation resulted in better bone containment than observed in the absence of CMC. These observations were confirmed mechanically, radiographically and histologically.

Conclusion

CMC-containing osteogenic devices (injectable configuration) can be used to repair non-critical size, 3 mm ulna segmental defects at a closed defect site.

TABLE 9

Evaluation of Improved Device Formulations of rhOP-1 for Repair of Noncritical Size Defects
MECHANICAL TESTING RESULTS

| Animal Number | Side | Time Period | Implant | Maximum Load to Failure (N) | Torque (Nm) | Percent intact control (%) | Angulation | Energy absorbed to failure (Nm-degrees) |
|---|---|---|---|---|---|---|---|---|
| 18750 | right | 4 weeks | FORMULATION 1 | 49.37 | 2.96 | 75.65 | 35.72 | 63.57 |
| 18643 | right | 4 weeks | FORMULATION 1 | 16.56 | 0.99 | 25.37 | 14.04 | 6.78 |
| 18043 | right | 4 weeks | FORMULATION 1 | 33.32 | 2.00 | 51.05 | 43.62 | 54.56 |
| | | | MEAN | 33.08 | 1.99 | 50.69 | 31.13 | 41.64 |
| | | | STANDARD DEVIATION | 16.41 | 0.98 | 25.14 | 15.32 | 30.52 |
| | | | SAMPLE SIZE | 3 | 3 | 3 | 3 | 3 |
| 17884* | right | 4 weeks | FORMULATION 2 | 32.47 | 1.95 | 49.75 | 50.11 | 55.91 |
| 18473 | right | 4 weeks | FORMULATION 2 | 43.83 | 2.63 | 67.15 | 37.53 | 51.77 |
| | right | 4 weeks | FORMULATION 2 | 10.79 | 0.65 | 16.53 | 20.78 | 5.94 |
| | | | MEAN | 20.03 | 1.74 | 44.48 | 36.14 | 37.87 |
| | | | STANDARD DEVIATION | 16.79 | 1.01 | 25.72 | 14.71 | 27.73 |
| | | | SAMPLE SIZE | 3 | 3 | 3 | 3 | 3 |
| 18772 | right | 4 weeks | FORMULATION 3 | 42.64 | 2.56 | 65.33 | 55.06 | 55.74 |
| 18640 | right | 4 weeks | FORMULATION 3 | 20.95 | 1.26 | 32.10 | 24.77 | 14.62 |
| 18508 | right | 4 weeks | FORMULATION 3 | 7.24 | 0.43 | 11.09 | 17.08 | 3.04 |
| | | | MEAN | 23.61 | 1.42 | 36.17 | 32.30 | 24.47 |
| | | | STANDARD DEVIATION | 17.85 | 1.07 | 27.35 | 20.08 | 27.70 |
| | | | SAMPLE SIZE | 3 | 3 | 3 | 3 | 3 |

*Calculations based on raw data from mechanical testing printout.

TABLE 10

Evaluation of Improved Device Formulations of rhOP-1 for Repair of Noncritical Size Defects
MECHANICAL TESTING RESULTS

| Animal Number | Side | Time Period | Implant | Maximum Load to Failure (N) | Torque (Nm) | Percent intact control (%) | Angulation | Energy absorbed to failure (Nm-degrees) |
|---|---|---|---|---|---|---|---|---|
| 18750 | left | 4 weeks | CONTROL 1 | 12.81 | 0.77 | 19.63 | 33.26 | 14.06 |
| 18643 | left | 4 weeks | CONTROL 1 | 11.00 | 8.00 | 16.85 | 59.35 | 16.83 |

TABLE 10-continued

Evaluation of Improved Device Formulations of rhOP-1 for Repair of Noncritical Size Defects
MECHANICAL TESTING RESULTS

| Animal Number | Side | Time Period | Implant | Maximum Load to Failure (N) | Torque (Nm) | Percent intact control (%) | Angulation | Energy absorbed to failure (Nm-degrees) |
|---|---|---|---|---|---|---|---|---|
| 18043 | left | 4 weeks | CONTROL 1 | 4.14 | 0.25 | 6.34 | 7.46 | 0.70 |
| | | | MEAN | 9.32 | 3.01 | 14.27 | 33.36 | 10.53 |
| | | | STANDARD DEVIATION | 4.57 | 4.33 | 7.01 | 25.95 | 8.62 |
| | | | SAMPLE SIZE | 3 | 3 | 3 | 3 | 3 |
| 17884* | left | 4 weeks | CONTROL 2 | 4.82 | 0.29 | 7.38 | 11.12 | 0.73 |
| 18473 | left | 4 weeks | CONTROL 2 | 4.53 | 0.27 | 6.94 | 30.63 | 2.50 |
| | left | 4 weeks | CONTROL 2 | 7.52 | 0.45 | 11.52 | 33.29 | 8.59 |
| | | | MEAN | 5.62 | 0.34 | 8.62 | 24.91 | 3.94 |
| | | | STANDARD DEVIATION | 1.65 | 0.10 | 2.53 | 12.03 | 4.12 |
| | | | SAMPLE SIZE | 3 | 3 | 3 | 3 | 3 |
| 18772 | left | 4 weeks | CONTROL 3 | 15.41 | 0.92 | 23.61 | 49.91 | 15.40 |
| 18640 | left | 4 weeks | CONTROL 3 | 10.28 | 0.62 | 15.75 | 40.50 | 11.23 |
| 18508 | left | 4 weeks | CONTROL 3 | 4.32 | 0.26 | 6.62 | 4.89 | 0.41 |
| | | | MEAN | 10.00 | 0.60 | 15.33 | 31.77 | 9.01 |
| | | | STANDARD DEVIATION | 5.55 | 0.33 | 8.50 | 23.75 | 7.74 |
| | | | SAMPLE SIZE | 3 | 3 | 3 | 3 | 3 |

*Calculations based on raw data from mechanical testing printout.

TABLE 11

Evaluation of Improved Device Formulations of rhOP-1 for Repair of Noncritical Size Defects - Unrelated Controls
MECHANICAL TESTING RESULTS

| Animal Number | Side | Time Period | Implant | Maximum Load to Failure (N) | Torque (Nm) | Percent intact control (%) | Angulation | Energy absorbed to failure (Nm-degrees) |
|---|---|---|---|---|---|---|---|---|
| 17932 | right | 8 weeks | Unrelated Control | 35.40 | 2.12 | 54.24 | 61.58 | 34.63 |
| 18926 | right | 8 weeks | Unrelated Control | 6.20 | 0.37 | 9.50 | 59.65 | 6.96 |
| 18754 | right | 8 weeks | Unrelated Control | 25.68 | 1.54 | 39.34 | 33.53 | 27.87 |
| 17932 | left | 8 weeks | Unrelated Control | 29.14 | 1.54 | 39.34 | 33.53 | 27.87 |
| 18926 | left | 8 weeks | Unrelated Control | 5.67 | 0.34 | 8.69 | 47.20 | 6.20 |
| 18754 | left | 8 weeks | Unrelated Control | 12.23 | 0.73 | 18.74 | 39.43 | 15.10 |
| | | | MEAN | 19.05 | 1.14 | 29.19 | 44.64 | 18.43 |
| | | | STANDARD DEVIATION | 12.68 | 0.76 | 19.42 | 14.14 | 11.36 |
| | | | SAMPLE SIZE | 6 | 6 | 6 | 6 | 6 |

2. Experiment 2: Accelerated Repair of a Closed Fracture Defect as Treated With a Unitary Device (Dogs)

The following is a comparative experimental study of the efficacy of injectable, CMC-containing rhOP-1 formulations for accelerating fracture healing in dogs.

Test System

Adult male mongrel dogs bred for purpose were utilized in this study. Special attention was paid in selecting animals of uniform size and weight to limit the variability in bone geometry and loading. The animals were screened clinically and radiographically to exclude acute and chronic medical conditions during a two-week quarantine period.

Using standard aseptic techniques, surgery was performed under isofluorane gas anesthesia and was monitored by electrocardiogram and heart rate monitors. Pre-surgical medication was administered approximately 20-30 minutes prior to anesthesia induction. The pre-surgical medication consisted of atropine (dosage 0.02 mg/lb body weight) and acepromizine (dosage 0.1 mg/lb body weight). Anesthesia was administered by intravenous injection of sodium pentothal at the dosage of 5.0 mg/lb body weight. Following induction, an endotracheal tube was placed and anesthesia was maintained by isofluorane inhalation. Both forelimbs were prepped and draped in sterile fashion. A lateral incision approximately two centimeters in length was made and exposure of the ulna was obtained using blunt and sharp dissection. The 3.0 mm noncritical sized defect was created in the mid-ulna using an oscillating saw. The radius was maintained for mechanical stability and no internal or external fixation was used. The site was irrigated with saline and the soft tissues meticulously closed in layers around the defect. The appropriate implant device was injected into the defect site as per the treatment schedule. The procedure was then repeated on the contralateral side with the appropriate implant.

Acepromizine (0.75 cc/50 lb body weight) and butorphanol tartrate (0.025 mg/lb body weight) was administered as required postoperatively. Animals were administered intramuscular antibiotics for four days post-surgery and routine anterior-posterior radiographs was taken immediately after surgery to insure proper surgical placement. Animals were kept in 3×4 foot recovery cages until weight bearing was demonstrated after which they were transferred to runs and allowed unrestricted motion.

Radiographs of the forelimbs were obtained weekly until four weeks, and then biweekly to 16 weeks in surviving animals using standardized exposure times and intensities. Radiographs were evaluated and compared to earlier radiographs to appreciate quality and speed of defect healing. Changes in radiographic appearance were evaluated based on presence and density of new bone formation, extent of defect bridging and incorporation of the host bone cortices.

Test Material Description

The implant materials consisted of recombinant human osteogenic protein-1 (rhOP-1) in an acetate buffer formulation and rhOP-1 in CMC-collagen. The rhOP-1 formulations were compared to vehicle only controls. The acetate buffer rhOP-1 formulation consisted of 3.5 mg/ml OP-1 in a lactose/acetate buffer delivered in a 100 µl volume. The vehicle control consisted of a 100 µl volume of lactose/acetate buffer. The rhOP-1/CMC-collagen formulation consisted of 0.35 mg rhOP-1 in 170 mg CMC-collagen matrix wetted with approximately 0.43 ml of saline and had the consistency of a paste. The control CMC-collagen consisted of 170 mg CMC-collagen matrix wetted with approximately 0.43 ml of saline and was also delivered in a 100 µl injectable volume.

Experimental Design

A total of 36 adult mongrel dogs were utilized. Bilateral ulna segmental defects, 3.0 mm in length, were created in all animals. Fourteen animals received an injection of 0.35 mg rhOP-1/acetate buffer formulation in one defect and the acetate buffer without rhOP-1 in the contralateral defect. Nine animals received an injection of 03.5 mg rhOP-1/CMC-collagen formation in one defect and CMC-collagen alone in the contralateral defect. the 23 animals were sacrificed at periods of 4, 8 and 12 weeks postoperative. Thirteen dogs received bilateral defects with no implant (defect only) and were evaluated at periods of 4, 8, 12 and 16 weeks postoperative.

Testing Procedures

At the end of the study period, animals were sacrificed using an intravenous barbiturate overdose. The ulna and radius were immediately harvested en bloc and placed in saline soaked diapers. Both ulna were macrophotographed and contact radiographs taken before soft tissues were carefully dissected away from the defect site. A watercooled saw was then used to cut the ulna to a uniform length of 9 cm with the defect centered in the middle of the test specimen for biomechanical testing evaluation.

If defect healing was sufficient based upon manual manipulation, specimens were tested to failure in torsion on an MTS closed-loop hydraulic test machine (Minneapolis, Minn.) operated in stroke control at a constant displacement rate of 50 mm/min. Each end of the bone segment was mounted in a cylindrical aluminum sleeve and cemented with methylmethacrylate. One end was rigidly fixed and the other was rotated counterclockwise. Since the dog ulna has a slight curvature, the specimens were mounted eccentrically to keep specimen rotation coaxial with that of the testing device. The torsional force was applied with a lever arm of 6 cm. Force-angular displacement curves were generated from which the torque and angular deformation to failure were obtained, and the energy absorption to failure computed as the area until the load-displacement curve.

Both tested and untested specimens were prepared for histologic evaluation. The individual specimens were fixed by immersion in 10% buffered formalin solution immediately following mechanical testing or after sectioning in untested specimens. On a water cooled diamond saw the specimens were divided by bisecting the specimen down its long axis. This procedure resulted in two portions of each specimen for histologic preparations including undecalcified ground sectioning and undecalcified microtome sectioning. The histologic sections were evaluated for the quality of union, the appearance and quality of the cortical and cancellous bone, and bone remodeling.

Results

Gross Observations

All rhOP-1 treated defects had new bone formation as early as 4 weeks postoperative. All treated defects were manually stable and bridged with solid new bone that began to remodel between 8 and 12 weeks postoperative. In some defects, the new bone extended beyond the defect ends and into the overlying soft tissues surrounding the defects.

Most control defects were not completely stable upon manual manipulation at 4 weeks postoperative, although most were mechanically tested. Fibrous tissue was often present and defect ends remained visible with some signs of new bone. By 12 weeks postoperative, most control defects were stable with only occasional slight motion of the defect ends.

Radiographic Evaluation

In the rhOP-1 treated defects, traces of new bone were seen by two weeks postoperative in and around the defect sites. The amount and density of new bone increased from 2 to 4 weeks with the host bone cortices beginning the obscure. Between 4 and 8 weeks postoperative, rhOP-1 treated defects had significant amounts of radiodense new bone at the defect ends and bridging the defect laterally. By 12 weeks, the host cortices were obscured with radiodense bridging bond.

The radiographic appearance of the treated and untreated control defects was significantly different from the appearance of the rhOP-1 treated defects. Between 2 and 3 weeks postoperative, there were no significant changes in the radiographic appearances compared to postoperative appearances. By 4 weeks, faint changes in the radiodensity of the host bone defect ends were visible. From 8 to 12 weeks, some new bone extended from the endosteal regions and host bone ends, although bridging was not complete. By 16 weeks postoperative, only one-half of the untreated controls showed radiographic signs of complete bony defect healing.

Mechanical Testing

The mean mechanical testing results by treatment group and time period are summarized in Tables 11A and 11B. Torsional strengths of defects treated with rhOP-1 were significantly greater than untreated controls and vehicle only controls and approached the strength of previously tested intact ulnae. The mechanical strength of the rhOP-1/acetate buffer formulation defects was 59% of intact ulna strength at 4 weeks postoperative, 77% at 8 weeks postoperative, and 98% at 12 weeks postoperative. The mechanical strength of the rhOP-1/CMC-collagen defects was 36%, 53% and 66% of intact strength at 4 weeks, 8 weeks and 12 weeks, respectively.

Mechanically, the control defect sites had little mechanical stability at the early time periods although defect strength did improve with time. The mechanical strength of defects receiving the control acetate buffer solution was between 23% to 30% of the rhOP-1/acetate buffer treated defects at equivalent time periods. The control defects had a mechanical strength equivalent to 16% of intact ulna strength at 4 weeks postoperative, 18% at 8 weeks, and 29% at 12 weeks. The CMC-collagen only defects were similar in mechanical strength to the control acetate buffer defects. The mechanical strength of untreated defects increased from 9% at 4 weeks to 70% at 12 weeks postoperative. The mean mechanical strength at 16 weeks postoperative decreased to 28% which was similar to the 8-week strength of 29%.

ally completed by 8 weeks postoperative, although areas of mineralizing cartilage were present. Defects were bridged and filled with dense woven bone and reorganization of the host bone cortices was observed by 12 weeks.

Treated and untreated control defects showed only signs of fibrous tissue union with small amounts of new bone formed along the lateral ulna periosteum or from the endosteal region at 4 weeks postoperative. At 8 weeks, fibrocartilage filled the control defects with areas of mineralizing cartilage present

TABLE 11A

Mechanical testing results, mean ± standard deviation (n)

| Implant | Weeks | Maximum Load to Failure (N) | Torque (Nm) | Percent Intact Control (%) | Angulation (degrees) | Energy absorbed to Failure (Nm-degrees) |
|---|---|---|---|---|---|---|
| rhOP-1/ acetate buffer | 4 weeks | 38.46 ± 17.3 (8) | 2.31 ± 1.0 (8) | 58.92 ± 26.5 (8) | 25.18 ± 16.2 (8) | 35.71 ± 39.3 (8) |
| rhOP-1/ acetate buffer | 8 weeks | 50.57 ± 23.0 (3) | 3.03 ± 1.4 (3) | 77.48 ± 35.3 (3) | 39.56 ± 14.6 (3) | 70.51 ± 38.0 (3) |
| rhOP-1/ acetate buffer | 12 weeks | 63.70 ± 22.1 (3) | 3.82 ± 1.3 (3) | 97.60 ± 33.8 (3) | 18.79 ± 2.4 (3) | 40.40 ± 7.2 (3) |
| Acetate buffer only | 4 weeks | 10.72 ± 6.4 (8) | 0.64 ± 0.4 (8) | 16.42 ± 9.7 (8) | 23.85 ± 22.3 (8) | 5.46 ± 7.9 (8) |
| Acetate buffer only | 8 weeks | 11.47 ± 9.4 (3) | 0.69 ± 0.6 (3) | 17.57 ± 14.5 (3) | 39.38 ± 32.4 (3) | 11.83 ± 10.2 (3) |
| Acetate buffer only | 12 weeks | 18.91 ± 29.9 (3) | 1.13 ± 1.8 (3) | 28.97 ± 45.9 (3) | 35.72 ± 11.4 (3) | 43.69 ± 72.7 (3) |
| rhOP-1/ CMC-collagen | 4 weeks | 23.61 ± 17.9 (3) | 1.42 ± 1.1 (3) | 36.17 ± 27.4 (3) | 32.30 ± 20.1 (3) | 24.47 ± 27.7 (3) |
| rhOP-1/ CMC-collagen | 8 weeks | 34.33 ± 22.6 (3) | 2.06 ± 1.4 (3) | 52.60 ± 34.6 (3) | 42.76 ± 20.2 (3) | 37.08 ± 14.4 (3) |
| rhOP-1/ CMC-collagen | 12 weeks | 43.39 ± 22.3 (3) | 2.60 ± 1.3 (3) | 66.47 ± 34.2 (3) | 32.07 ± 10.1 (3) | 47.65 ± 21.8 (3) |
| CMC-collagen only | 4 weeks | 10.00 ± 5.55 (3) | 0.60 ± 0.3 (3) | 15.33 ± 8.5 (3) | 31.77 ± 23.8 (3) | 9.01 ± 7.7 (3) |
| CMC-collagen only | 8 weeks | 4.45 ± 4.0 (3) | 0.27 ± 0.2 (3) | 6.81 ± 6.2 (3) | 31.90 ± 25.6 (3) | 5.09 ± 6.3 (3) |
| CMC-collagen only | 12 weeks | 18.82 ± 8.6 (3) | 1.13 ± 0.5 (3) | 28.84 ± 13.2 (3) | 43.87 ± 11.0 (3) | 23.55 ± 16.4 (3) |
| Untreated (5/8 tested) | 4 weeks | 6.04 ± 1.8 (5) | 0.36 ± 0.1 (5) | 9.25 ± 2.8 (5) | 43.71 ± 12.3 (5) | 6.00 ± 1.8 (5) |
| Untreated | 8 weeks | 19.05 ± 12.7 (6) | 1.14 ± 0.8 (6) | 29.19 ± 19.4 (6) | 44.64 ± 14.1 (6) | 18.43 ± 11.4 (6) |
| Untreated | 12 weeks | 45.91 ± 40.6 (6) | 2.75 ± 2.4 (6) | 70.34 ± 62.1 (6) | 38.04 ± 17.8 (6) | 38.26 ± 21.4 (6) |
| Untreated (5/6 tested) | 16 weeks | 18.55 ± 9.3 (5) | 1.11 ± 0.56 (5) | 28.43 ± 14.2 (5) | 39.15 ± 8.3 (5) | 20.19 ± 9.8 (5) |

TABLE 11B

Mechanical testing results in terms of percentage of intact ulna strength, mean ± standard deviation (n)

| Implant | 4 weeks | 8 weeks | 12 weeks | 16 weeks |
|---|---|---|---|---|
| rhOP-1 acetate buffer | 59 ± 26 (8) | 77 ± 35 (3) | 98 ± 34 (3) | — |
| Acetate buffer only | 16 ± 10 (8) | 18 ± 15 (3) | 29 ± 46 (3) | — |
| rhOP-1 CMC-collagen | 36 ± 27 (3) | 53 ± 35 (3) | 66 ± 34 (3) | — |
| CMC-collagen only | 15 ± 9 (3) | 7 ± 6 (3) | 29 ± 13 (3) | — |
| Untreated | 9 ± 3 (5) | 29 ± 19 (6) | 70 ± 62 (6) | 28 ± 14 (5) |

Histologic Evaluation

The histology of the rhOP-1 and control defects correlated well with gross, radiographic and mechanical testing results. In the rhOP-1 treated defects, proliferative new bone formation was observed spanning the defects and in some cases extending into the subcutaneous tissue. New bone formed from the endosteal ulna regions and from the periosteum near the defect cortices. Bridging with new bone was gener-
between new bone growth. Significant amounts of new bone formed at the host bone cortices and extended into the defects. Defect cortices were obscured with dense new bone formation and endochondral healing was advanced, although union was not complete. By 16 weeks, control defects were bridged with new bone with some gaps of mineralizing cartilage present. New bone extended from the host cortices and adjacent periosteal tissue layers across the defect.

Conclusion

The results of this study demonstrate that osteogenic proteins injected into noncritical sized defects can accelerate bone repair. The local percutaneous injection of rhOP-1 to the noncritical sized defect in the canine ulna resulted in a proliferative periosteal and endosteal new bone formation compared to untreated and vehicle only treated control defects. Radiographically, the rhOP-1 injection resulted in diffuse calcifications of new bone and early fracture callus formation as early as 2 to 3 weeks postoperative with significant bone bridging and incorporation of the host cortices by 8 to 12 weeks postoperative. The mechanical strength of noncritical sized defects treated with rhOP-1 approached the strength of intact ulna at 12 weeks and were 2 to 3 times that observed in control defect healing.

C. Repair of Fracture Defects Using Improved Osteogenic Devices Containing Carboxymethylcellulose 1. Experiment 1: Goat Fracture Study Using Varying Doses of OP-1 (Closed Defect Site)

The following is a comparative randomized experimental study of fresh closed tibial midshaft fracture defects (distracted to 5 mm) in goats.

Choice of Experimental Animal

It is generally recognized in the art that goats have a bone healing rate comparable to that of humans. Thus, the results of this study can be extrapolated to a clinical setting.

Moreover, it is appreciated by the skilled artisan that the bones of goats show similarity to those of humans regarding size, shape and mechanical load.

As disclosed and described herein, an animal model for a closed diaphyseal fracture has been developed. This model promotes the study of natural and accelerated fracture healing, with or without an internal fracture fixation device, by permitting creation of a reproducible standard fracture of the hind limb. Briefly, in fully anesthetized goats, a closed fracture of the midshaft of the tibia is created with the aid of a three point bending device. After closed reduction and distraction to 5 mm of the fracture, an external cast is applied. Because of a decrease in the swelling of the hind limb, the cast is replaced biweekly to retain stability. After 2 weeks, the animals are full weight bearing on the fractured limb, and after 4-6 weeks the fracture is healed clinically and radiographically. The cast is removed after 6 weeks.

The animals are purchased from Ruiter (Netherlands), a goat breeding specialist. Random bred adult female milkgoats will be used. To circumvent the influence of a developing skeleton on the results, adult animals will be used. The animals are skeletally mature, 1 to 2 years old and weigh about 50 kg.

Experimental Procedure

As a premedication, ketamin 10 mg/kg i.m. and atropine 1.5 mg i.m. (or art-recognized equivalents of the foregoing medications) are administered about 15 minutes before fully anesthetizing the animals. The latter is accomplished with etomidates (or art-recognized equivalents thereof) 0.3 mg/kg i.v. After intubation, anesthesia is maintained with an $O_2/N_2O$-mixture (1:1, vol/vol) supplemented with 1 to 2% isoflurane (or art-recognized equivalents thereof).

With a 3-point bending device, a varus trauma is applied to the left tibia until a closed midshaft fracture is obtained. The fracture is then reduced manually, and the skin over the fracture area is shaved. The whole left hind limb is iodinated with an alcohol containing disinfectant solution for closed osteogenic device administration by injection and to dry the skin for subsequent cast immobilization. The osteogenic device is injected at the fracture site in the vicinity of the fracture gap to maximize contact with the medullary cavity. For example, an osteogenic device is injected intramedullary with a thick bone marrow aspiration needle. After the injection, cast immobilization is applied.

Study Design

The animals are divided into 5 groups (I-V) of 3 animals and 1 group (VI) of 9 animals according to treatment: 0.5 mg OP-1 in an injectable configuration of osteogenic device containing at least OP-1, collagen matrix, and binding agent such as CMC, formulated as described above (directly after creation of the fracture) (Group I), 1.0 mg OP-1 in an injectable device containing at least OP-1, collagen, and binding agent, such as CMC, (directly after creation of the fracture) (Group IV), 1.0 mg OP-1 in a standard configuration of OP-1 device (corresponding to 0.4 grain OP-1 device) injected directly after creation of the fracture (Group V), and no treatment with OP-1 (Group VI, controls). The treatment groups are summarized as follows:

| Group | Time of injection (days) | Device | Amount of OP-1 (mg) | Approximate Number of animals |
|---|---|---|---|---|
| I | 0 | Injectable | 0.5 | 3 |
| II | 0 | Injectable | 1.0 | 3 |
| III | 3 | Injectable | 1.0 | 3 |
| IV | 0 | Injectable | 1.0 | 3 |
| V | 0 | Standard Device | 1.0 | 3 |
| VI | None | None | 0 | 9 |

The animals are sacrificed 2, 4 and 6 weeks after creation of the fracture. In groups I to V, one animal is sacrificed at each time interval, and in group VI, three animals are sacrificed at each time interval. By comparing the treated groups to the controls, the accelerating effect of treatment on fracture healing can be determined. Information about the OP-1 dose effect and the time of injection can be obtained by comparison of group I to group II, respectively, and group II to group III. Differences in efficacy between different configurations are assessed by evaluating the results of groups II, IV and V.

In other related experiments, doses of osteogenic protein such as OP-1 will range from approximately 0.125 to 10.0 mg. Certain other configurations of improved osteogenic devices will contain varying amounts of binding agent such as CMC, ranging from below 200 mg CMC/1000 mg collagen matrix to above 200 mg CMC/1000 mg collagen matrix. Wetting agent volumes will be varied as earlier described to achieve the desired consistency/configuration of osteogenic device. In yet other related experiments, other binding agents such as fibrin glue and/or other matrices such as β-TCP will be used.

Evaluating Defect Repair

Radiography

X-rays are made following a standardized procedure and depict the fracture site in two directions, anteroposterior and mediolateral. The first radiographs are taken immediately after creation of the fracture and thereafter biweekly until sacrifice of the animals. The radiographs at the time of sacrifice are made after removal of the casting material; all others are made with the casting material in situ. They are judged qualitatively by two blinded radiologists or surgeons, and, if possible, the following grading scale for evaluating the healing process is applied:

Grade 0: No difference compared to directly after creation of the fracture
Grade, 1: Small amount of callus
Grade 2: Moderate amount of callus
Grade 3: Large amount of callus
Grade 4: Fading of the fracture ends Special attention is paid to the type of fracture and alignment.

Computed Tomography

After removal of the left hindlimb and casting material, and after making of the radiographs, a CT-scan of the fracture area is made. The soft tissues should remain in situ for a better quality of scans. Remnants of the fracture gap and callus can be made visible in this way. Moreover, the amount of callus can be calculated. More detailed information about the progress of the healing process can be obtained with CT scans than with plain radiographs.

Biomechanical Test

After CT scanning and subsequent removal of all soft tissues from the tibia, biomechanical investigations are performed. A method for advanced mechanical testing of bone is developed as follows: the bending stiffness in 24 directions at angular increments of 15° is measured and depicted as a vector in a X-Y coordinates system, by which an ellipse is obtained. The ellipse is compared with that of the contralateral intact tibia. Parameters can be derived from this comparison that serve as measures of the healing efficiency. Finally, a torsion-test-to-failure is done and the measured torsion strength, torsion stiffness, angular displacement and energy absorption-to-failure is expressed as a percentage of the contralateral healthy tibia. This comparison with the contralateral tibia is made to reduce the interindividual variation.

Histology

After biomechanical testing, the bone fragments are held together with special rings for histologic examination. Standard fixation, imbedding and staining techniques for bone and cartilage are used. Special attention is paid to signs of fibrous, osteochondral or bony union. A histologic scoring system is applied to quantitate the amount of fibrous tissue, cartilage, newly formed bone and bone marrow in the fracture gap.

Experimental Results

It is expected that mechanical, radiographic, tomographic and histological data will indicate that injectable configurations of improved osteogenic devices can induce accelerated repair of closed site fracture defects.

Conclusion

Improved osteogenic devices (injectable configuration) can be used to repair fresh tibial midshaft fracture defects (distracted to 5 mm) at a closed defect site.

2. Experiment 2: Goat Fracture Study Using Varying Doses of OP-1 at Varying Times (Closed Defect Site)

This independent study also uses goats as the animal model for studying repair of fracture defects using improved osteogenic devices. Using techniques similar to those described above, fresh closed diaphyseal fractures (mostly transverse and simple oblique) with reduction with external fixation and distraction to 5 mm are treated using CMC-containing osteogenic devices.

The study design is as follows:

| Group | Treatment | No. Goats |
|---|---|---|
| I | No injection | 10 |
| II | CMC + collagen alone via injection | 10 |
| III | CMC + collagen + OP-1 (2.5 mg OP-1/1000 mg collagen) via injection | 10 |
| IV | CMC + collagen + OP-1 (half-maximal dosage of 1.25 mg OP-1/1000 mg collagen) via injection | 10 |

Five goats in each group are sacrificed at 2 weeks post-treatment and five goats in each group are sacrificed at 4 weeks post-treatment.

Other related studies investigate repair of fracture defects at time points greater than 4 weeks, and investigate both lower and higher dosages of OP-1. Additionally, repair of fracture defects using differing total amounts (mg) of the CMC-containing OP-1 device administered at the defect site are studied. One study utilizes a device of 400 mg total weight administered at the defect site. Yet other related studies will utilize any if the aforementioned binding agents, such as fibrin glue, and/or any of the aforementioned matrices, such as β-TCP.

Defect repair is evaluated using a variety of routine clinical protocols, including radiography, CT scan, biomechanical testing, and histology, as described in more detail above.

Experimental Results

It is expected that mechanical, radiographic, tomographical, histological data will indicate that injectable configurations of improved osteogenic devices can induce accelerated repair of closed site fracture defects. It is also anticipated that, in certain preferred embodiments, low doses of osteogenic protein will be effective to induce repair, especially in improved osteogenic devices.

Conclusion

Improved osteogenic devices (injectable configuration) can be used to repair fresh closed diaphyseal fractures (distracted to 5 mm) at a closed defect site.

D. Repair of Osteochondral Defects Using Improving Osteogenic Devices Containing Carboxymethylcellulose 1. Experiment 1: Full-Thickness Osteochondral Defects (Dogs)

A study using the dog osteochondral plug defect model was conducted to demonstrate the efficacy of improved osteogenic devices for repairing osteochondral/chondral defects. Four formulations of implants were evaluated, including, (1) standard osteogenic device, including rhOP-1 and collagen matrix, (2) improved osteogenic device, including rhOP-1, collagen matrix and carboxymethylcellulose (CMC) binding agent, (3) collagen matrix only, or (4) collagen matrix and CMC binding agent.

Briefly, full thickness defects 5 mm in diameter and extending 6 mm into the subchondral bone were created bilaterally on the medial femoral condyle of 4 adult mongrel dogs. Adult male mongrel dogs were chosen because of their anatomical size and bone repair and remodeling characteristics. Special attention was paid in selecting animals of uniform size and weight to limit the variability in bone geometry and joint loading. The animals were radiographically screened pre-operatively to ensure proper size, skeletal maturity, and that no obvious osseous abnormalities existed. The left side defects received standard osteogenic device in two animals, and the improved osteogenic device in the other two animals. The right side defects received matrix alone in one animal, a matrix/binding agent mixture in one animal, and was untreated in the remaining two animals.

Test Device Description

The standard osteogenic device consisted of rhOP-1 admixed with bovine Type I bone collagen matrix (2.5 mg rhOP-1/g matrix). The improved osteogenic device comprised 100 mg of the OP-1/collagen matrix standard osteogenic device combined with 20 mg of CMC (total of 120 mg). Controls consisted of bovine Type I bone collagen matrix alone, and the collagen matrix with CMC. Both were supplied in 100 mg quantities.

Study Design

Study design is summarized in Table 12.

TABLE 12

Dog Osteochondral Defect Repair using OP-1

| Animal Number | Left Implant | Right Implant |
|---|---|---|
| H122 | OP-1 | Matrix |
| H130 | OP-1 | None |
| H125 | OP-1/CMC | None |
| H132 | OP-1/CMC | None |

OP-1: 100 mg OP-1/Collagen Device (standard osteogenic device).
OP-1/CMC: 120 mg OP-1/CMC/Collagen Device (improved osteogenic device).
Matrix: 100 mg Collagen.
CMC/Matrix: 100 mg CMC/Collagen.
Devices and controls were wetted with saline (approx. 0.21 to 0.26 ml) to achieve a putty consistency prior to implantation.

Surgery

Using standard aseptic techniques, surgery was performed under isofluorane gas anesthesia. Anesthesia was administered by intravenous injection of sodium pentothal at a dosage of 5.0 mg/lb body weight. A medial parapatellar incision approximately four centimeters in length was made. The patella was retracted laterally to expose the femoral condyle. A 5 mm drill bit with a specially designed sleeve to prevent over drilling of the defect depth (6 mm) was used to create the final defect. Sterile saline was added to the improved osteogenic device and mixed just prior to implantation. After irrigation of the defect with saline to remove bone debris and spilled marrow cells, the appropriate device was packed into the defect site using a blunt probe. Enough device was placed within the defect so that it was flush with the articulating surface. The joint capsule and soft-tissues were then closed in layers. The procedure was repeated on the contralateral side with the appropriate implant.

Evaluations and Terminal Procedures

Osteochondral healing was evaluated grossly and histologically using routine protocols, as described below. Radiographs were utilized to evaluate healing.

At twelve weeks post-operative each animal was sacrificed by an intravenous barbiturate overdose. Both right and left distal femurs were harvested en bloc and kept in cool saline until gross grading and microphotography were completed. The specimens were then placed in 4% paraformaldehyde fixative, labeled with all necessary identifications, and stored at 4° C. until shipped approximately 10 days post-sacrifice. Just prior to shipping the specimens were trimmed into small blocks, with the articular defect in the center.

Gross Analysis

Each harvested defect was graded for gross appearance. This analysis apportions points based upon the formation of intra-articular adhesions, restoration of articular surface, erosion and appearance of the cartilage. A total of eight points is possible. The gross grading scale is set forth in Table 13.

TABLE 13

Gross Grading Scale

| | Grades |
|---|---|
| Intra-articular adhesions | |
| None = | 2 |
| Minimal/fine loose fibrous tissue = | 1 |
| Major/dense fibrous tissue = | 0 |
| Restoration of articular surface | |
| Complete = | 2 |
| Partial = | 1 |
| None = | 0 |
| Erosion of cartilage | |
| None = | 2 |
| Defect site/site border = | 1 |
| Defect site and adjacent normal cartilage = | 0 |
| Appearance of cartilage | |
| Translucent = | 2 |
| Opaque = | 1 |
| Discolored or irregular = | 0 |
| TOTAL SCORE | 8 possible points |

Histology

All specimens were prepared for histologic evaluation. The individual specimens were fixed by immersion in 4% paraformaldehyde solution. In addition, using routine procedures as described elsewhere herein, tissue typing analysis was performed in order to characterize the collagen type and percent tissue composition. Non-decalcified sections, one from each specimen, stained with Safranin-O and Fast Green stains (to indicate glycosaminoglycan content in the matrix), were returned for evaluation.

Histologic sections were based upon the nature of the repair cartilage, structural characteristics, and cellular changes. The histologic grading scale is set forth in Table 14.

TABLE 14

Histology Grading Scale

| Nature of the Predominant Tissue: | | |
|---|---|---|
| Cellular morphology | Hyaline articular cartilage = | 4 |
| | Incompletely differentiated = | 2 |
| | Fibrous tissue or bone = | 0 |
| Safranin-O staining of the matrix | Normal/near normal = | 3 |
| | Moderate = | 2 |
| | Slight | 1 |
| | None = | 0 |
| STRUCTURAL CHARACTERISTICS: | | |
| Surface regularity | Smooth/intact = | 3 |
| | Superficial horizontal lamination = | 2 |
| | Fissures, 25-100% of thickness = | 0 |
| | Severe disruption, fibrillation = | 0 |

TABLE 14-continued

Histology Grading Scale

| | | |
|---|---|---|
| Structural integrity | Normal = | 2 |
| | Slight disruption, including cysts = | 1 |
| | Severe disintegration = | 0 |
| Thickness | 100% of normal cartilage thickness = | 2 |
| | 50-100% = | 1 |
| | 0-50% = | 0 |
| Bonding to the adjacent cartilage | Bonded at both ends of the defect = | 2 |
| | Bonded at one end or partially bonded at both ends = 1 | 1 |
| | Not bonded = | 0 |
| FREEDOM FROM CELLULAR CHANGES OF DEGENERATION: | | |
| Hypocellularity | None = | 3 |
| | Slight = | 2 |
| | Moderate = | 1 |
| | Severe = | 0 |
| Chondrocyte clustering | None = | 2 |
| | <25% of cells = | 1 |
| | >25% of cells = | 0 |
| Freedom from degenerative changes in adjacent cartilage | Normal cellularity, no clusters, normal staining = | 3 |
| | Normal cellularity, mild clusters, moderate staining = | 2 |
| | Mild or moderate hypocellularity, slight staining = | 1 |
| | Severe hypocellularity, poor or no staining = | 0 |
| TOTAL | | 24 possible points |

Results

All surgeries were uneventful with no post-operative complications. In general, some medial knee swelling was observed on post-operative day four bilaterally in all four animals and subsided by post-operative day ten. No animal experienced any adverse reaction related to the implanted materials or experimental procedures.

Gross Evaluation

A summary of the mean gross evaluation grades appears in Table 15.

TABLE 15

Mean Gross Evaluation Grade ± standard deviation (n)

| | Standard Osteogenic Device | Improved Osteogenic Device | Collagen Matrix Only | Collagen Matrix/CMC | No Treatment |
|---|---|---|---|---|---|
| Intra-Articular | 2.0 ± 0.0 | 2.0 ± 0.0 | 2.0 ± 0.0 | 2.0 ± 0.0 | 2.0 ± 0.0 |
| Restoration of Surface | 1.5 ± 0.6 | 1.5 ± 0.6 | 0.0 ± 0.0 | 0.5 ± 0.6 | 2.0 ± 0.0 |
| Erosion | 1.8 ± 0.5 | 1.23 ± 0.5 | 1.5 ± 0.7 | 1.0 ± 1.4 | 1.8 ± 0.5 |
| Appearance | 0.8 ± 0.5 | 1.0 ± 0.8 | 0.0 ± 0.0 | 1.0 ± 0.0 | 1.5 ± 0.6 |
| Total (out of 8 possible points) | 6.0 ± 1.4 (2) | 5.8 ± 1.7 (2) | 3.5 ± 0.7 (1) | 4.5 ± 0.7 (1) | 7.3 ± 0.5 (2) |

Histological Evaluation

The non-treated defects and defects treated with the improved osteogenic device of OP-1, collagen matrix and CMC received the greatest mean histologic grade, 15 and 16.5 out 24 possible points, respectively. In each of these groups, however, one specimen looked markedly better than the other. The collagen matrix only, collagen matrix with CMC, and the standard osteogenic device treated sites however, scored slightly more consistently, and lower than, the sites treated with improved osteogenic device (n≤2). A summary of the mean histological grades appears in Table 16.

TABLE 16

Mean Histologic Evaluation Grade ± standard deviation (n)

| | Standard Osteogenic Device | Improved Osteogenic Device | Collagen Matrix Only | Collagen Matrix/CMC | Non Implanted |
|---|---|---|---|---|---|
| Nature of the Predominant Tissue | 3.5 ± 0.7 (2) | 4.5 ± 2.1 (2) | 1.0 (1) | 2.0 (1) | 4.0 ± 2.8 (2) |
| Structural Characteristics | 1.5 ± 0.1 (2) | 5.5 ± 0.6 (2) | 7.0 (1) | 6.0 (1) | 5.0 ± 2.8 (2) |
| Freedom from Cellular Changes of Dengeneration | 4.5 ± 0.7 (2) | 6.5 ± 2.1 (2) | 3.0 (1) | 4.0 (1) | 6.0 ± 1.4 (2) |
| Total (out of 24 possible points) | 12.5 ± 0.7 (2) | 16.5 ± 7.8 (2) | 11.0 (1) | 12.0 (1) | 1.5 ± 7.1 (2) |

Unexpectedly, sites treated with the improved osteogenic device achieved the highest mean scores for the nature of the new repair tissue, for the structural characteristics of the repair, and for minimizing the degeneration of the repair cartilage or the surrounding intact cartilage. The improved osteogenic device sites also received the highest overall total score. These results were weighted by the score of one animal, in which the cellular and tissue morphology was consistent with articular cartilage. The repair cartilage was continuous with the intact cartilage and the thickness of the repair was the same as the intact cartilage. The subchondral bone layer was also completely restored. Healing was not as advanced in the other sites treated with the OP-1/collagen matrix with or without CMC. Lower scores were the result of incomplete differentiation of the repair tissue, incomplete subchondral bone restoration, and uneven thickness of the repair. Residual implant or carrier material was not observed in any section.

Comparisons within animals demonstrated that, in three animals, the defects receiving devices containing OP-1, with or without CMC (all left defects), achieved histologic grades equal to or greater than the contralateral defect receiving the control matrix or no treatment.

Unexpectedly, the OP-1 device without CMC induced bone and cartilage formation, but in a more disorganized fashion with considerable fibrous tissue present. Untreated or carrier alone samples were filled by fibrous cartilage and dense connective tissue.

These data suggest that the unexpected superior repair achieved with improved osteogenic device is associated with the differences in its consistency relative to that of the standard osteogenic device without binding agent, which in turn affects the containment of the device per se at the defect site. Formulation adhesion and disintegration properties are expected to be critical in articular cartilage defects given the dynamic nature of the joint.

Immunostaining of Type I and Type II Collagen and Polarized Light Microscopy

This study also stained sections to compare collagen repair at defect sites treated with: no device, two types of matrix only compositions (matrix and matrix/binding agent), or both matrix compositions with OP-1.

In general, using the collagen Type I antibody, staining of the existing underlying subchondral bone, as well as the newly regenerated bone, was observed. The newly regenerated bone differed slightly from the existing bone by the presence of regions of more disorganized matrix when viewed under phase contrast microscopy. Using the Type II collagen antibody, the existing articular cartilage stained qualitatively as well as the reparative tissue in the defects, although staining of the new tissue was less intense. In at least one defect treated with improved osteogenic device, complete regeneration of the subchondral bone was observed with articular-like cartilage regenerated along the top. The cellular matrix of this regenerated cartilage was not identical to the existing articular cartilage, but a visible cellular matrix composed of large loose bundles could be seen under phase contrast.

Defects Treated with Improved Osteogenic Device.

In defects treated with improved osteogenic device, at least one animal evidenced repair of articular cartilage at a macroscopic level. The subchondral bone was regenerated and a new cartilage layer of near normal thickness was seen by histological staining with toluidine blue and Safarnin O. These layers and tissues stained appropriately, with Type I antibody localized in the subchondral bone and Type II collagen localized in the new cartilage-like layer. There was also some evidence of the regeneration of a zone of calcified cartilage and distinct tidemark in the regenerated cartilage. However, some differences were seen between the new and existing articular cartilage layer. The new cartilage had a higher density of chondrocytes and contained loose, disorganized bundles of fibers visible by phase contrast microscopy or with polarized light. It should be noted that only a single time point during the repair process is represented here and that the results of longer or shorter periods is unknown.

Defects Treated with Standard Osteogenic Device.

Defects treated with standard osteogenic devices showed approximately 50% of the bone was regenerated in the defect site with in-growth of articular cartilage from the edges of the defect. There appeared to be some additional areas of articular cartilage formation next to the newly regenerated bone, with the remainder of the defect filled with reparative tissue. The reparative tissue stained lightly with collagen Type II, and not with Type I collagen, antibodies. More chondrocytes were present with large loose bundles of matrix surrounding the cells. Treatment with the standard osteogenic device differed from treatment of the improved osteogenic device in that the subchondral bone failed to regenerate to its normal level, and dense disorganized fibrous tissue appeared above the new cartilage, which caused the top of the defect to bulge with an irregular surface. This fibrous tissue appeared to have more fibroblast-like cells with fibrous bundles arranged parallel to the articular surface.

Defects Treated with Matrix/Binding Agent.

A defect with only matrix/binding agent without OP-1 showed regeneration of about one-third of the removed subchondral bone, with the remainder filled with a reparative tissue This regenerated tissue stained lightly with Type I collagen antibodies, especially near the bottom of the defect, and showed stronger staining with the Type II collagen antibody, with strongest staining near the surface. A dense disorganized visible matrix is apparent in the top half of the reparative tissue, and a more organized horizontal pattern of fibers appears in the bottom half. Toluidine blue did not stain the reparative tissue, whereas Safranin O stained the top and bottom half differentially. The half near the articular surface stained lightly with Safranin O, and the bottom stained with Fast Green. A similar distinction was observed between the two halves of the reparative tissue when stained with Masson Trichrom. Although the reparative tissue did not look like articular cartilage, the region near the articular surface did appear to contain Type II collagen, an acidic matrix with perhaps some mucopolysaccharides. The bottom half had more Type I collagen with less carbohydrate and may be more connective tissue-like in nature.

The single defect treated with collagen matrix alone did not show any regeneration of the subchondral bone. The reparative tissue that filled the defect stained lightly with both collagen Type I and II antibodies. This tissue had an increased fibrous matrix with fibroblastic like cells and appeared in some areas to be similar to fibrocartilage. This sample was similar to the treatment with the CMC/collagen matrix alone, with slight localization of both Type I and II collagen in the reparative tissue. In addition, the defect site showed the same differential staining with Safranin O/Fast Green, with staining of the top half of the reparative tissue with Safranin O and the bottom with Fast Green.

Summary and Conclusion

Osteochondral defects treated with the improved osteogenic devices unexpectedly demonstrated more advanced cartilage regeneration, chondrocyte and cartilage phenotype compared to defects treated with the standard osteogenic device, collagen matrix alone, or collagen matrix admixed with CMC, all of which demonstrated less organized repair cartilage and subchondral bone formation. Poor repair by treatment with the collagen matrix or collagen matrix with CMC indicates that the presence of a collagen scaffold alone is not sufficient to induce healing and may actually deter the progression of healing and organization of repair tissue.

Full-thickness osteochondral defects can be repaired using CMC-containing osteogenic devices in accordance with the methods of the instant invention. It is expected that full-thickness osteochondral defects can also be repaired using improved osteogenic devices containing any of the aforementioned preferred binding agents such as fibrin glue and/or any of the aforementioned preferred matrices.

2. Experiment 2: Long Term Evaluation of Repair of Full-Thickness Osteochondral Defects (Dogs)

This study was conducted to further evaluate repair of osteochondral/chondral defects by improved osteogenic devices. To date, the study examined the effects of the improved osteogenic device at 6 and 12 weeks and will continue to examine effects at 26 and 52 weeks. This provides long term repair stability data. The organization of new cartilage over time was followed to determine if it approximates normal tissue with respect to its structure and function. Two formulations of devices were evaluated in osteochondral/chondral defects including: 1) improved osteogenic device, or 2) mock devices containing CMC and collagen matrix only.

Briefly, full thickness defects 5 mm in diameter extending 6 mm into the subchondral bone were created bilaterally on the medial femoral condyle of 16 adult mongrel dogs. Adult mongrels were utilized in this study because of their anatomical size and known bone repair and remodeling characteristics. All animals were between 1 and 4 years old and weigh approximately 20 to 30 kg. Specific attention was paid to selecting animals of uniform size and weight to limit the variability in joint loading. The animals were radiographically screened to ensure proper size, skeletal maturity, and that no obvious osseous abnormalities exist. In each group of four dogs, the left side defects received improved osteogenic device. The right side defects received matrix/binding agent in two animals, and the remaining two animals were untreated. At sacrifice, the distal femurs were retrieved en bloc, and the defect sites evaluated histologically and grossly based on upon the above-described scheme.

The improved osteogenic device comprises standard device (2.5 mg rhOP-1/1 g matrix) admixed with CMC. To formulate the improved device, 100 mg of the rhOP-1/collagen mixture were admixed with 20 mg of CMC immediately prior to implantation (total 120 mg). The collagen only device consists of bovine Type I collagen (100 mg). The study design is summarized in Table 17.

TABLE 17

Dog Osteochondral Defect Repair

| Group | Dogs (2 defects/animal) | Left Implant | Right Implant | Duration |
|---|---|---|---|---|
| I | 4 | OP-1/CMC | None/Vehicle | 6 weeks |
| II | 4 | OP-1/CMC | None/Vehicle | 12 weeks |
| III | 4 | OP-1/CMC | None/Vehicle | 26 weeks |
| IV | 4 | OP-1/CMC | None/Vehicle | 52 weeks |

OP 1/CMC: 120 mg OP-1 CMC/Collagen Device (improved osteogenic device)
Vehicle: 100 mg CMC/Collagen.

Surgery

Using standard aseptic techniques, surgery was performed under isofluorane gas anesthesia. A medial parapatellar incision approximately four centimeters in length was made. The patella was retracted laterally to expose the femoral condyle. Using a ⅛ inch drill bit, a pilot hole was made in the weight bearing region of the medial femoral condyle. A 5 mm drill bit with a specially designed sleeve to prevent over drilling of the defect depth (6 mm) was used to create the final defect. After copious irrigation with saline to remove bone debris and spilled marrow cells, the appropriate experimental device was packed into the defect site using a blunt probe. The joint capsule and soft-tissues were then meticulously closed in layers. The procedure was repeated on the contralateral side with the appropriate implant.

Evaluation

Four animals each were sacrificed at 6 and 12 weeks and four animals will be sacrificed at 26 and 53 weeks postoperative. Animals were sacrificed using an intravenous barbiturate overdose. The femurs were immediately harvested en bloc and stored in a saline soaked diaper. High power photographs of the defect sites were taken. Soft-tissues were meticulously dissected away from the defect site. The proximal end of the femur was removed.

The gross appearance of the defect sites and repair tissue were graded based upon the above-described parameters by two independent observers blinded to the treatment assignment. Points were apportioned according to the presence of intra-articular adhesions, restoration of the articular surface, cartilage erosion and appearance.

All specimens were prepared for histologic evaluation immediately after gross grading and photography. The individual distal femurs were fixed by immersion in 10% buffered formalin solution or in 4% paraformaldehyde solution. On a water cooled diamond saw, each defect site was isolated. Three sections from three levels were cut from each block. Levels 1 and 3 were closest to the defect perimeter. Level 2 was located at the defect center. Three sections from each level were stained with either hematoxylin and eosin, Goldner's trichrome, Safranin O, or Fast Green. Sections were then graded based upon the above-described scheme. This analysis apportioned points based upon the nature of the repair tissue, structural characteristics, and cellular changes. A total of 24 points are possible.

Result and Conclusion

After 6 weeks, certain of the above-treated animals were sacrificed and immunohistochemical evaluations were conducted as described elsewhere herein. The results were as follows: In all cases, defects treated with OP-1 CMC/collagen device exhibited superior repair. With the OP-1 CMC/collagen device, there was unexpectedly complete or nearly complete bridging of the defect with cartilage tissue. Type II collagen staining was observed in the reparative cartilage with little or no Type I collagen staining. Proteoglycan staining followed the type II collagen localization with darker staining in areas that more closely resembled mature hyaline cartilage. Based on Safranin-O staining, regeneration of surface layer of cartilage was not yet complete at 6 weeks post-treatment.

After 12 weeks, healing had significantly progressed in defects treated with improved devices. No appreciable healing was observed in the controls. The mean gross grading score observed with improved devices at 12 weeks was 6.50±0.89 (n=8); control means was 3.69±0.70 (n=8). At all remaining time points, it is anticipated that defects treated with the improved osteogenic devices will demonstrate more advanced cartilage regeneration, chondrocyte and cartilage phenotype, in an accelerated manner relative to defects treated with only collagen/CMC or left untreated. The defects treated with improved osteogenic device are anticipated to exhibit cartilage and subchondral bone tissue, whereas the collagen/CMC treated or untreated defects are expected to induce disorganized bone and cartilage formation with considerable fibrous tissue present.

Full-thickness osteochondral defects can be stably repaired using CMC-containing osteogenic devices in accordance with the methods of the instant invention. It is expected that experiments similar to those described above, in which other preferred binding agents such as fibrin glue are evaluated, will demonstrate that improved osteogenic devices can stably repair full-thickness osteochondral defects.

E. Repair of Chondral Defects Using Improved Osteogenic Devices Containing Carboxymethylcellulose 1. Experiment 1: Long Term Evaluation of Repair Chondral vs. Osteochondral Defects (Sheep)

This study evaluates repair of both chondral and osteochondral defects by improved osteogenic devices using a large animal model. The increased thickness of the articular cartilage and the similarities to humans in size and weight-bearing characteristics make the sheep a model from which human clinical applications can be extrapolated, especially for clinical application of improved osteogenic devices for repair of chondral defects. The study groups are as follows:

A-Osteochondral (full-thickness) Defects (5 mm diameter);
Group A I: no treatment
Group A II: carboxymethylcellullose/collagen
Group A III: carboxymethylcellullose/OP-1/collagen
Group A IV: lyophilized allograft
Group A V: lyophilized allograft+OP-1
B-Chondral (partial thickness) defects (5 mm diameter);
Group B I: no treatment
Group B II: carboxymethylcellullose/collagen
Group B III: carboxymethylcellullose/OP-1/collagen
Group B IV: hyaluronic acid+chondroitin sulfate paste
Group B V: hyaluronic acid+chondroitin sulfate paste+OP-1

Both foreknee joints of each sheep are operated on, and two defects per joint are created (one each on the medial and the lateral condyle). One of the joints has two standardized partial thickness chondral defects (5 mm in diameter) created on each condyle, while the other joint has two deeper, full thickness osteochondral defects (about 1-2 mm into the subchondral bone) created. Each group has a subgroup sacrificed early at 8 weeks and another kept for longer term evaluation for 6-7 months.

There are a total of 20 groups and 12 defects per group. Therefore, the total number of defects is 240 and total number of sheep is 60. There are five different treatment groups; three controls (no treatment and two different mock devices) and two different OP-1 formulations for each defect type. Improved osteogenic devices comprising OP-1 in CMC/collagen will be used for osteochondral defect repair and chondral defect repair. The devices are formulated such that 2.5 mg OP-1/g collagen are added to each defect site receiving this improved osteogenic device. Repair is evaluated at 8 weeks and 6-7 months. The treatment protocol is shown in Table 18.

TABLE 18

Sheep Chondral and Osteochondral Defect Repair using OP-1

| Group | Sheep (4 defects/ sheep) | Osteochondral (2 defects/ sheep) | Chondral Defects (2 defects/sheep) | Duration |
|---|---|---|---|---|
| I | 12 | Untreated Control | Untreated Control | 8 weeks (6) >26 weeks (6) |
| II | 12 | CMC/Collagen Control | CMC/Collagen Control | 8 weeks (6) >26 weeks (6 |
| III | 12 | OP-1 + CMC/Collagen | OP-1 + CMC/Collagen | 8 weeks (6) >26 weeks (6 |

Surgeries on the two knees are staggered by two weeks to allow healing of the first knee prior to surgery on the second knee. The first surgery is used to generate chondral defects, the second is for osteochondral defects. The surgery is performed in a fully equipped operating room using standard techniques and equipment used in human surgery. The sheep are allowed to ambulate freely in their pasture territory postoperatively. Staggered surgeries result in 8 week healing times for chondral defects and 6 week healing times for osteochondral defects. At sacrifice, the joints are perfused, fixed and processed according to standard cytological protocols.

At the end of the study periods, the animals are sacrificed and the joints are harvested en bloc. The gross appearance of the defect sites and repair tissue is graded using routine methods such as those described above. Points are apportioned according to the presence of intra-articular adhesions, restoration of articular surface, cartilage erosion and appearance.

Using methods similar to those described above, specimens are prepared for histologic evaluation immediately after gross grading and photography.

It is expected that defects treated with OP-1/CMC/collagen devices will exhibit superior repair similar to that in Experiment D.2 above. It is further expected that improved osteogenic devices containing any of the aforementioned preferred binding agents, such as fibrin glue, will also exhibit repair of both chondral and osteochondral defects.

2. Experiment 2: Long Term Evaluation of Repair of Using Varying Doses Of OP-1 Subchondral Defects (Goats)

A study using skeletally mature milk-goats is conducted to demonstrate the efficacy of improved osteogenic device for repairing osteochondral/chondral defects. Formulations of improved osteogenic device with varying concentrations of rhOP-1 are used, along with mock or no-device controls. The mock device consists of collagen admixed with carboxymethylcellulose (CMC). Furthermore, the animal groups are sacrificed at 4, 12 and 24 months after surgery to compare the rate and stability of defect repair. The following summarizes the experimental parameters.

Groups

|  | Post-operation time: | | |
| --- | --- | --- | --- |
|  | 4 mo. | 12 mo. | 2 year |
| 1. rhOP-1 800 µg/ml | A | B | C |
| 2. rhOP-1 1600 µg/ml | A | | |
| 3. rhOP-1 3200 µg/ml | A | | |
| 4. Mock device | A | B | |
| 5. No device | A | B | |

Briefly, subchondral defects are made in the left knees of 56 skeletally mature milk-goats: The defects are 8 mm in diameter and 3 mm in depth. This defect configuration prevents very high shear stresses in the defect leading to collagen Type I formation. Dutch milk-goats, about 2 years old and weighing approximately 50 kg are used in this experiment. Devices corresponding to 2.5 mg rhOP-1/gram collagen are provided. In each case, 0.2 grams of CMC are added to standard osteogenic device, then approximately 2.6 ml of saline are added and mixed. This yields material of approximately 3-4 ml of improved osteogenic device. This material is then used to fill the defect volume.

Surgical Technique

Anesthesia is induced and the left knee is opened via a medial parapatellar approach. The patella is dislocated to the lateral side and the medial condyle is exposed. With a sharp hollow tube, the outlines of a defect are made in the anterior weight bearing part of the medial condyle. With a square pointed handburr that is placed inside the tube, a defect down to the subchondral bone is created. The proximal tibia is then exposed, and a periosteal flap of the same diameter as the defect in the medial condyle is taken. The periosteal flap is partially fixed, with its cambium layer towards the defect, to the remnants. The defect is filled with the appropriate test material and covered with the periosteal flap, using a resorbable suture. The CMC device is added via a syringe until the defect is filled, and the flap is then completely sutured. In control animals, a mock device including collagen and CMC only is used. A second control group received no implant at all, but received only a periosteal flap.

Post-Operative Treatment

Unrestricted, weight-bearing activity is allowed as much as can be tolerated post-operatively.

Clinical Performance

The weight bearing pattern is assessed at 2, 4, 6, and 8 weeks, and then every 4 weeks.

Gross Analysis

Gross evaluations are made based upon the scheme presented above. After sacrificing the animal, the presence or absence of knee contractures is recorded, and both the patella and condyles of the femur are examined for adhesions, articular surface contour, the appearance of the restored cartilage, and the presence or absence of cartilage erosions. Each of these characteristics is given a score. Color slides are taken using a macro-lens.

Histological Analysis

To aid in visualization of the regenerated subchondral bone and to localize the borders of the defect during histological evaluation, the goats receive a double labeled tetracycline before sacrificing. This allows histomorphometry of the bony filling of the deeper part of the defect. The histological samples are also viewed by incorporating polarized microscopy to provide information on regular structural features.

For histological analysis, the specimens, including the subchondral bone, are fixed in 10% phosphate buffered formalin and are embedded undecalcified in methylmethacrylate (MMA). With a heavy duty microtome, sections of 5 µm thick are made. The sections are stained with toluidine blue to identify cartilage and with Goldner's Trichrome to identify bone. Assessment is made of tissue hyalinity, affinity of the matrix for toluidine blue (metachromasia), surface irregularity, chondrocyte clustering regenerated subchondral bone, bonding to the adjacent articular cartilage, inflammatory cell infiltration around the implant, and freedom from degenerative changes in the adjacent cartilage. Each of these characteristics is given a score.

Biochemical Analysis

Extraction of proteoglycans: For biochemical analysis, control cartilage and tissue from the defect is collected in cold phospate-buffered saline (PBS). Proteoglycans are extracted from lyophilized sections by treatment with 4 M guanidine HCl, 0.15 M potassium acetate at pH 5.8 in the presence of proteinase inhibitors (5 mM benzamidine, 0.1 M 6-amino-n- hexanoic acid, 10 mM EDTA, 5 mM phenylmethylsulfonyl fluoride, and 5 mM n-ethylmaleimide) at 4° C. for 60 hours. The extract and residue are separated. The residue is thoroughly rinsed with extraction buffer, which is added to the extract. The extracts are analyzed for chondroitinsulphate content and used for gel filtration.

Gel filtration: Aliquots of extracts are applied to Sepharose C 12 B columns (0.66×145 cm) (Pharmacia AB, Uppsala, Sweden) and eluted with a dissociative buffer at pH 6.1, containing 4 M guanidine HCl, 0.1 sodium sulfate, 0.05 M sodium acetate, and 0.1% triton X-100. The flow rate is 1.2 ml/hr. Fractions are analyzed for chondroitinsulphate content. The amount of large cartilage-specific molecules, probably aggrecans, can be calculated.

MRI

Magnetic resonance imaging (MRI) is performed for 2 purposes. First, to monitor 1 month post-operatively that the flap plus implant has remained in place. Second, group 1C (2 years or more post-op) is followed longitudinally with MRI at 4 months, 12 months and at sacrifice.

Summary

It is anticipated that defects treated with improved osteogenic device will demonstrate advanced cartilage regeneration, chondrocyte and cartilage phenotype compared to the mock or no-device controls. It is also anticipated that low doses of OP-1 will at least achieve repair quantitatively and qualitatively similar to that of higher doses.

F. Repair of Chondral Defects Using Osteogenic Protein

This study investigated mammalian cartilage formation in subchondral lesions treated with recombinant human osteogenic protein-1 (rhOP-1) (alone or in combination with a collagen matrix) and/or autologous perichondrium.

Material and Methods

In the medial femoral condyle of the left knee joint of 15 goats, a subchondral defect of 9 mm diameter was made. The defect was filled with an implant consisting of fresh coagulated blood mixed with: (a) small particles of autologous ear perichondrium; or (b) rhOP-1; or (c) rhOP-1 plus ear perichondrium. Rh—OP-1 was either added in combination with a collagen matrix (OP-1 Device) or without a collagen matrix (OP-1 alone). The defect was closed with a periosteal flap, which was stitched to the cartilage. After implantation times of 1, 2 and 4 months, the extent of repair of each defect was investigated with standard histological techniques (metachromasia and hyalinity) and well-known biochemical methods (gel chromatography of proteoglycans).

Results

After 1 and 2 months in this particular study, there were no apparent differences between control (implant (a) above) and the various OP-1 treated defects. However, after 4 months, only one out of three control defects showed detectable cartilage formation, while all four OP-1 treated defects were completely or partly filled with cartilage, as indicated by the histological and biochemical analysis set forth in Table 19.

TABLE 19

| Implant | % of defect[1] | A Biochemical Score | B Histology Score | Cartilage Score[2] partial | Cartilage Score[2] total |
|---|---|---|---|---|---|
| Control | 86% | 0.7 | 0.0 | 0.60 | |
|  | 14% | 3.0 | 4.0 | 0.98 | 1.58 |
| OP-1 Device | 62% | 2.0 | 4.0 | 3.72 | |
|  | 38% | 3.3 | 6.0 | 3.53 | 7.25 |
| OP-1 Device + perichon. | 79% | 1.2 | 2.0 | 2.53 | |
|  | 21% | 5.7 | 6.0 | 2.46 | 7.99 |
| OP-1 alone | 79% | 2.0 | 5.0 | 5.53 | |
|  | 21% | 2.1 | 6.0 | 1.70 | 4.23 |
| OP-1 + perichon. | 78% | 1.0 | 2.0 | 2.34 | |
|  | 22% | 4.2 | 5.0 | 2.02 | 4.36 |

[1]The defect was divided into homogeneous parts, the % is indicated.
[2]Calculated as follows: % × (A + B), e.g. 0.86 × (0.7 + 0.0) = 0.60.

Table 19 sets forth the cartilage score of condylar defects, treated for 4 months without OP-1 (control) or with OP-1 plus or minus perichondrium in the presence or absence of a collagen matrix.

Biochemical score (A) was assigned a value from 0-5 based on gel chromatography.

Histology score (B) is based on undecalcified plastic sections on a grading scale of 0 to 6.

Conclusion

The results of this study confirm that OP-1 has cartilage-promoting utility in large subchondral defects in goats. This indicates that OP-1 is of clinical relevance in treating large lesions of articular cartilage and is particularly useful for chondral repair of weight-bearing skeletal defects caused by trauma or disease in mammals.

In related studies, it is anticipated that other improved osteogenic devices such as fibrin-glue containing devices, will result in repair of large subchondral defects. Moreover, such repair will be accompanied by regeneration of more stable, pristine articular cartilage. It is further anticipated that subchondral defect repair will occur at an accelerated rate with reduced amounts of OP-1 when admixed with collagen matrix and a binding agent, such as CMC, relative to OP-1 admixed with collagen alone. Moreover, such repair will be accompanied by regeneration of more stable, pristine articular cartilage.

G. Segmental Defect Repair (Critical and Non-Critical Size) Using Improved Osteogenic Devices Comprising Apatites and/or TriCalcium Phosphates (TCP) and/or Collagen Matrices Improved devices comprising a variety of matrices or admixtures thereof will be used to repair segmental ulna defects (critical and non-critical size) at varying doses of OP-1 in rabbits and dogs. Improved devices will comprise: Pyrost® matrix (Osteo AG, Switzerland), a HAp block derived from bovine bone; 100% HAp granules (approximately 300-400 or 350-450μ); 100% TCP (approximately 400μ); and 50% HAp/50% TCP (approximately 400μ). Other embodiments will comprise one or more of the earlier-described matrices of appropriate porosity. One particularly preferred embodiment of improved osteogenic device will comprise Collapat® matrix (Osteo AG, Switzerland), a sponge of HAp and collagen. Another particularly preferred embodiment comprises approximately 0.6 g CMC per g HAp granules or per g granules of 75% HAp/25% TCP, especially when a device with putty consistency is desired. Another preferred embodiment described above contains β-TCP and fibrin glue.

It is expected that improved devices such as those described above will induce repair of segmental defects, and certain preferred embodiments will do so at low doses of OP-1.

H. Bone Formation Using Fibrin Glue as Binding Agent

Four rat subcutaneous studies were completed for evaluating fibrin glue OP-1 formulation on bone formation. The amount of bone formation at 10 µg OP-1 using the three different sources of fibrin glue were similar, ranging from 25% to 40% (See Tables 19A-19F). There was no clear correlation between inflammation and bone formation in these studies. Results indicated that rat reacted differently to fibrin glue from different species; For example, human fibrin glue from Tissucol® elicited an inflammation response from 2 to 2.7 (See Table 19A), bovine fibrin glue caused an inflammation response from 2 to 3.5 (See Tables 19B and 19C) and rat fibrin glue had the lowest inflammation response from 1 to 1.3 (See Table 19D) on a scale of 0-4. Typically, an inflammation response of 3-4 is defined as severe and 1-2 is defined as mild to medium.

TABLE 19A

IN VIVO data of Tissucol ®/OP-1

| Study | OP-1, µg n = 4 | Half Explant wt, mg | $Ca^{+2}$, µg/mg | % Bone/ Histology | Fibrosis (0-4) | Inflammation (0-4) |
|---|---|---|---|---|---|---|
| Tissucol ® | 0 | n.d. | <1 | 0 | 2.3 +/− 0.6 | 2.7 +/− 1.2 |
| Tissucol ® | 10 | 16 +/− 6 | 15 +/− 23 | 25 +/− 25 | 3.3 +/− 1.0 | 2.5 +/− 0.6 |
| Tissucol ® | 20 | 58 +/− 42 | 39 +/− 9 | 66 +/− 32 | 1.8 +/− 0.5 | 2 +/− 0.8 |
| OP-1 | 10 | 29 +/− 21 | 49 +/− 8 | 95 +/− 6 | 0.8 +/− 0.5 | 0.5 +/− 0.6 |

Twenty µL OP-1 (10 µg or 20 µg in 5% lactose) was mixed with 50 µL fibrinogen (70-110 mg/mL) and 50 µL thrombin solution (500 U/mL) prior to subcutaneous implantation.

TABLE 19B

IN VIVO data of Bovine Fibrin Glue

| (Implant) | OP-1, µg n = 4 | Half Explant wt, mg | $Ca^{+2}$, µg/mg | % Bone/ Histology | Fibrosis (0-4) | Inflammation (0-4) |
|---|---|---|---|---|---|---|
| 6% fibrin glue | 0 | n.d. | | | | |
| 6% fibrin glue | 10 | 18 +/− 8 | 25 +/− 12 | 40 +/− 43 | 2.3 +/− 0.6 | 2 +/− 1 |
| OP-1 | 10 | 58 +/− 8 | 65 +/− 10 | 100 +/− 0 | 0.75 +/− 0.5 | 0 +/− 0 |

Twenty µL OP-1 (10 µg in 5% lactose) was mixed with 50 µL bovine fibrinogen (60 mg/mL) and 50 µL bovine thrombin solution (300 U/mL) prior to subcutaneous implantation.

TABLE 19C

IN VIVO data of Bovine Fibrin Glue

| (Formulation) | OP-1, µg n = 4 | Half Explant wt, mg | $Ca^{+2}$, µg/mg | % Bone/ Histology | Fibrosis (0-4) | Inflammation (0-4) |
|---|---|---|---|---|---|---|
| 4% fibrin glue | 0 | n.d. | <3 | 0 | 2.25 +/− 1 | 3 +/− 1.4 |
| 4% fibrin glue | 10 | 15 +/− 7 | 10 +/− 8 | 24 +/− 25 | 2.5 +/− 0.6 | 3.5 +/− 1 |
| OP-1 | 10 | 8 +/− 5 | 42 +/− 7 | 88 +/− 10 | 1 +/− 0 | 0 +/− 0 |

Twenty µL OP-1 (10 µg in 5% lactose) was mixed with 50 µL bovine fibrinogen (40 mg/mL) and 50 µL bovine thrombin solution (200 U/mL) prior to subcutaneous implantation.

TABLE 19D

IN VIVO data of Rat Fibrin Glue

| | OP-1, µg n = 4 | Half Explant, mg | $Ca^{+2}$, µg/mg | % Bone/ Histology | Fibrosis (0-4) | Inflammation (0-4) | % Cyst |
|---|---|---|---|---|---|---|---|
| Rat fibrin | 10 | 32 +/− 13 | 2 +/− 0.6 | 13 +/− 19 | 1.3 +/− 0.5 | 1.0 +/− 0.8 | 9 +/− 12 |
| dil. 2 | 10 | 38 +/− 23 | 2 +/− −0.8 | 23 +/− 21 | 1.8 +/− 0.5 | 1.3 +/− 0.5 | 26 +/− 18 |

Twenty µL OP-1 (10 µg in 5% lactose) was mixed with 50 µL bovine fibrinogen (40 mg/mL) and 50 µL bovine thrombin solution (200 U/mL) prior to subcutaneous implantation.

Two other rat in vivo studies were completed for evaluating devices containing fibrin glue and OP-1 on bone formation. In the first study, bovine fibrinogen (504, Sigma F8630, 10 mg/mL) and bovine thrombin (50 μL, 50 U/mL) were mixed with OP-1 devices right before subcutaneous implantation. The positive controls are OP-1 devices wetted with 100 μL phosphate buffered saline. The OP-1 devices were prepared by mixing 10 μg OP-1 in 47.5% ethanol/0.01% TFA with 25 mg collagen and lyophilized overnight. Results are shown in TABLE 19E. There was no significant difference in bone formation between standard OP-1 devices and OP-1 devices combined with bovine fibrin glue. Also, a lower inflammation response was observed to the OP-1 devices/bovine fibrin glue formulation compared with the combination of liquid OP-1 bovine fibrin glue (see TABLES 19B and 19C).

TABLE 19E

IN VIVO data of Bovine Fibrin Glue with OP-1 Device

| | OP-1, μg n = 4 | Half Explant, mg | $Ca^{+2}$, μg/mg | % Bone/ Histology | Fibrosis (0-4) | Inflammation (0-4) |
|---|---|---|---|---|---|---|
| Fibrin + OP-1 device | 0 | 62 +/− 15 | 20 +/− 7 | 0 +/− 0 | 2.0 +/− 0.0 | 1.0 +/− 0.0 |
| Fibrin + OP-1 device | 10 | 123 +/− 21 | 43 +/− −11 | 66 +/− 13 | 1.5 +/− 0.6 | 1.3 +/− 0.5 |
| OP-1 device | 10 | 144 +/− 33 | 54 +/− 5 | 78 +/− 13 | 1.0 +/− 0.8 | 0.5 +/− 0.6 |

In a second study, different concentrations of Tissucol® were combined with the standard OP-1 device. That is, one lyophilized OP-1 device (25 mg total weight, 10 μg OP-1) was combined with human fibrinogen solution (50 pit, fibrinogen 70-110 mg/mL or diluted 2 or 4 or 8 folds in phosphate buffered saline) and thrombin solution (50 μL, 500 U/mL or diluted 2 or 4 or 8 folds in phosphate buffered saline) immediately prior to implantation. The positive controls are OP-1 devices wetted with 100 μL phosphate buffered saline. Results are shown in TABLE 19F. There is no significant difference in bone formation between standard OP-1 devices and OP-1 devices combined with different concentration of Tissucol®. Also, the concentration of fibrinogen had no significant effect on bone formation.

TABLE 19F

IN VIVO data of Tissucol ® with OP-1 Devices

| 97-0137 (#1111) | OP-1, μg n = 4 | Half Explant, mg | $Ca^{+2}$, μg/mg | % Bone/ Histology | Fibrosis (0-4) | Inflammation (0-4) |
|---|---|---|---|---|---|---|
| OP-1 + Tissucol ® | 10 | 163 +/− 50 | 37 +/− 7 | 55 +/− 30 | 2.0 +/− 0.8 | 1.8 +/− 1.0 |
| OP-1 + 2 folds diluted Tissucol ® | 10 | 162 +/− 32 | 34 +/− 8 | 54 +/− 13 | 1.8 +/− 1.0 | 1.8 +/− 1.0 |
| OP-1 + 4 folds diluted Tissucol ® | 10 | 170 +/− 19 | 41 +/− 6 | 69 +/− 26 | 1.5 +/− 1.0 | 1.5 +/− 1.0 |
| OP-1 + 8 folds diluted Tissucol ® | 10 | 177 +/− 23 | 40 +/− 8 | 55 +/− 25 | 1.8 +/− 1.0 | 1.8 +/− 1.0 |
| OP-1 device | 10 | 137 +/− 43 | 58 +/− 10 | 84 +/− 8 | 1.0 +/− 0.0 | 1.0 +/− 0.0 |

In summary, the handling property of standard. OP-1 devices is improved by using fibrin glue, e.g., and the collagen particles remain integrated with the glue. The in vivo data indicated that OP-1 devices with fibrin glue promote bone formation.

I. Defect Repair Using Improved Osteogenic Devices Containing Fibrin Glue as Binding Agent Fibrin glue-containing improved devices comprising a variety of matrices or admixtures thereof will be used to repair bone, osteochondral or chondral defects at varying doses of OP-1 art-recognized animal models. Certain embodiments of preferred devices will comprise: fibrin glue, collagen and OP-1. Other embodiments of preferred devices will comprise: fibrin glue, β-TCP and OP-1. Finally, further testing will include any of the aforementioned matrix materials suitable for use with the present invention.

It is expected that fibrin glue-containing improved devices such as those described above will promote and accelerate bone formation in critical and non-critical sized defects, non-union fractures, and fractures, as well as promote and accelerate repair of osteochondral and chondral defects.

J. Segmental Defect Repair (Critical and Non-Critical Size) Using Fibrin Glue-Containing Improved Device The following is a comparative experimental study of the efficacy of fibrin glue-containing improved devices for healing segmental (critical and non-critical sized) defects.

Test System

As described above, adult male mongrel dogs bred for purpose are utilized in this study. Special attention is paid in selecting animals of uniform size and weight to limit the variability in bone geometry and loading.

As also described above surgery is performed using standard aseptic techniques under isofluorane gas anesthesia. Both forelimbs are prepped and draped in sterile fashion. A lateral incision approximately two centimeters in length is made and exposure of the ulna is obtained using blunt and sharp dissection. Either a critical or a noncritical sized defect is created in the mid-ulna using an oscillating saw. The radius is maintained for mechanical stability and no internal or external fixation is used. The site is irrigated with saline and the soft tissues meticulously closed in layers around the defect. The appropriate implant device is implanted or injected into the defect site. The procedure is then repeated on the contralateral side with the appropriate implant.

Animals are administered intramuscular antibiotics for four days post-surgery and routine anterior-posterior radiographs are taken immediately after surgery to insure proper surgical placement. Animals are kept in 3×4 foot recovery cages until weight bearing is demonstrated, after which they are transferred to runs and allowed unrestricted motion.

Radiographs of the forelimbs are obtained weekly until four weeks, and then biweekly to 16 weeks in surviving animals using standardized exposure times and intensities. Radiographs are evaluated and compared to earlier radiographs to appreciate quality and speed of defect healing. Changes in radiographic appearance are evaluated based on presence and density of new bone formation, extent of defect bridging and incorporation of the host bone cortices.

Test Material Description

The implant materials contain recombinant human osteogenic protein-1 (rhOP-1) in an acetate buffer formulation, and rhOP-1 in either fibrin glue plus collagen or fibrin glue plus β-TCP. The rhOP-1 formulations are compared to vehicle only controls. The acetate buffer rhOP-1 formulation consists of 3.5 mg/ml OP-1 in a lactose/acetate buffer delivered in a 100 μl volume. The vehicle control consists of a 100 μl volume of lactose/acetate buffer. Test formulations contain rhOP-1/fibrin glue-collagen or rhOP-1/fibrin glue β-TCP.

Experimental Design

Bilateral ulna segmental defects, critical or non-critical size, are created in all animals. One group of animals receive an injection of 0.35 mg rhOP-1/acetate buffer formulation in one defect and the acetate buffer without rhOP-1 in the contralateral defect. Another group of animals receive an injection of rhOP-1/fibrin glue-collagen or rhOP-1/fibrin glue-β-TCP formation in one defect and fibrin glue-β-TCP or collagen alone in the contralateral defect. Animals are sacrificed at periods of 4, 8 and 12 weeks postoperative. Certain dogs receive bilateral defects with no implant (defect only) and are evaluated at periods of 4, 8, 12 and 16 weeks postoperative.

Testing Procedures

At the end of the study period, animals are sacrificed using an intravenous barbiturate overdose. The ulna and radius are immediately harvested en bloc and placed in saline soaked diapers. Both ulna are macrophotographed and contact radiographs taken before soft tissues were carefully dissected away from the defect site. A water-cooled saw is then used to cut the ulna to a uniform length of 9 cm with the defect centered in the middle of the test specimen for biomechanical testing evaluation.

If defect healing is sufficient based upon manual manipulation, specimens are tested to failure in torsion on an MTS closed-loop hydraulic test machine (Minneapolis, Minn.) operated in stroke control at a constant displacement rate of 50 mm/min. Each end of the bone segment is mounted in a cylindrical aluminum sleeve and cemented with methylmethacrylate. One end is rigidly fixed and the other is rotated counterclockwise. Since the dog ulna has a slight curvature, the specimens are mounted eccentrically to keep specimen rotation coaxial with that of the testing device. The torsional force is applied with a lever arm of 6 cm. Force-angular displacement curves are generated from which the torque and angular deformation to failure are obtained, and the energy absorption to failure is computed as the area until the load-displacement curve.

Both tested and untested specimens are prepared for histologic evaluation. The individual specimens are fixed by immersion in 10% buffered formalin solution immediately following mechanical testing or after sectioning in untested specimens. On a water-cooled diamond saw the specimens are divided by bisecting the specimen down its long axis. This procedure results in two portions of each specimen for histologic preparations, including undecalcified ground sectioning and undecalcified microtome sectioning. The histologic sections are evaluated for the quality of union, the appearance and quality of the cortical and cancellous bone, and bone remodeling.

Results

It is expected that fibrin glue-containing improved devices with any of the aforementioned preferred matrices, such as collagen or β-TCP, will promote repair of both critical and non-critical size segmental defects.

VII. Human Clinical Studies: Methods of Use of Improved Osteogenic Devices

A. Repair of Bone Defects.

1. Trial 1: Fresh Open Tibial Fracture.

This study is a multi-center, prospective, randomized study of patients with fresh, fractures of the tibia requiring surgical intervention at the fracture site.

Introduction

Currently there are approximately 26 million fractures annually world wide. The majority of fractures heal without complication and are not considered "a problem". There is a "quality of life impact," however, with patients being out of work or prevented from engaging in normal activity, not being able to return to activity or, when they do, suffering with lingering pain. Patients, particularly in the western world, are growing to expect solutions to these problems.

The cost of fracture treatment is astounding. In 1988, fractures cost an estimated $20 billion in the United States. The largest segment, approximately 44% or $7.2 billion, was related to in-patient treatment. In that year, almost 900,000 persons were hospitalized for fractures, with an average length of stay of 8.8 days for a total of 7.9 million days. Nursing home costs were second at $2.8 billion, and out-patient hospital care third at $1.8 billion.

When the economic ramifications of fractures are considered in conjunction with the quality of life impact, there is indeed a need for improvement in treatment methodologies, especially fractures that are considered potentially problematic. These are fractures that because of the nature of the injury or mitigating host issues, may require additional surgical interventions, take an extended time to heal, and/or may prevent full functional recovery.

Thus the study described below is designed to investigate improved osteogenic devices as a healing accelerator for fresh fractures in humans and as a means to decrease the potential for post-injury problem healing requirement intervention to augment the healing process. Additionally, certain patients within this study will be treated with improved osteogenic devices as a bone graft substitute in patients requiring bone grafting post-injury or in cases of delayed healing.

As contemplated herein and described above, currently preferred embodiments of improved osteogenic devices have a consistency which can be injected through a large gauge needle or can be placed through an open incision such that it will remain generally in place in a bloody environment. In addition to more conventional packaging, the injectable improved osteogenic devices can be packaged in applicator/syringe ready to be used. A variety of nozzles and needles can be added to customize application. Other embodiments will also be rendered radio opaque by addition of radio opaque components such as described earlier.

It is expected that the improved osteogenic devices of the instant invention (injectable and implantable) will decrease the incidence of additional interventions, speed rate of healing, improve quality of life and speed return to normal activity. Furthermore, it is expected that the improved osteogenic devices disclosed herein will be used in fractures of all long bones, clavicle, and scapula to promote healing, leading to decreased incidence of intervention (including re-operation), increased speed of healing, increased rate of return to normal activity, and decreased morbidity. In contrast to currently available fracture repair modalities, there is no biomechanical requirement with the improved devices and methods disclosed herein.

Study Design

Patients will require surgical treatment of open fractures of the tibia acquired secondary to trauma. The fracture must have the potential to be adequately stabilized at the fracture site to permit healing. Patients will show radiographic evidence of skeletal maturity.

Type of Treatment

Type #1: Initial injury at ≤7 days at definitive closure.
Type #2 At up to 6 weeks post-initial injury in patients requiring bone grafting.

Type #1 fractures are those not requiring bone grafting. Patients will be randomized in a 1:1 ratio of standard treatment (debridement of fracture site, reduction and stabilization), which will be the control group versus standard treatment plus OP-1 device with and without a binding agent, such as carboxymethylcellulose (CMC). In certain patients, dosages of osteogenic protein OP-1 will vary. As described above, a currently preferred formulation of the improved osteogenic device contains 2.5 mg OP-1/1000 g collagen/200 mg CMC. OP-1 dosages will vary from ½ maximal to 4×; CMC content will vary from 100-300 mg. As also described above, variations of wetting agent volumes will be investigated by the attending surgeon/physician to achieve the desired consistency/configuration of device. Patients from the first group who are not healed 6 months post-treatment will again be randomized in a 1:1 ratio of bone grafting (control) versus OP-1.

Type #2 fractures are those requiring bone grafting. Patients will be randomized in a 1:1 ratio of bone grafting (control) versus OP-1. Patients from the first group who are not healed 6 months post-treatment will be crossed over from bone grafting to OP-1 and from OP-1 to bone grafting.

Study Plan

Patients will be followed for a minimum of 1 year post-treatment to assess healing, with a 24 month follow-up to assess status.

Follow-up assessments will be performed at 2 weeks, 4 weeks and every 4 weeks up to 6 months, and at 8, 10 and 12 months post-treatment. All patients will have an additional follow-up assessment at 24 months to determine overall health and fracture site status. The following assessments will be performed: changes in physical examination; radiographs; clinical pain assessments; clinical assessments of weight-bearing; clinical assessments of function; quality of life assessment (pre-discharge, 6 and 12 months); and documentation of any interventions to augment/promote healing (surgical and nonsurgical) and hardware failures/replacements.

It is expected that fractures treated with improved osteogenics will evidence an accelerated rate of healing.

Additionally, it is expected that the patients treated with improved osteogenic devices will experience at least the following additional benefits:

1) Potential for decreased healing time with faster restoration of function, weight bearing and ambulation;
2) Potential for prevention of delayed/mal/non-union;
3) Return to normal activities sooner/less time lost from jobs/school;
4) Potential saving from further intervention/surgical procedures for promotion of healing;
5) Less hardware complications; and
6) In those patients who require bond grafting, the benefit of no second site surgery for bone harvest with associated morbidity.

2. Trial 2; Fresh Closed Diaphyseal Fracture.

Repair of fresh closed diaphyseal fractures in human subjects will be evaluated using improved osteogenic devices. Specifically, patients will be treated with injectable improved osteogenic devices by injecting the device at the closed defect site. It is anticipated that accelerated repair of the defect will be observed relative to patients not treated with improved osteogenic devices.

3. Other Human Trials

It is anticipated that Trials 1 and 2 as set forth above will be repeated using various configurations of improved osteogenic devices containing fibrin glue. It is further anticipated that such devices will promote bone formation, and in certain embodiments accelerate defect repair relative to untreated subjects.

B. Repair of Osteochondral Defects.

1. Experiment 1: Osteochondritis Dessicans

Osteochondral defect models support the clinical use of rhOP-1 to treat Osteochondritis Dissecans (OD) and trauma defects. OD is a disease resulting in localized areas of osteochondral defects. One cause of the disease may be ischemia damage to the localized area, but its exact etiology is unknown. In patients with OD, the affected area becomes avascular, with subsequent changes in the overlying articular cartilage. Patient's suffering from OD of the knee experience symptoms including locking of the joint, localized pain, swelling and retropatellar crepitus. An experiment involving patients with OD of the knee is conducted in order to compare the ability of improved osteogenic device, against that of standard osteogenic device, to repair OD defects.

Current methods known in the art for the treatment of OD involve the use of highly invasive surgical techniques. In most skeletally mature patients with OD, surgery is required. Surgical techniques require arthroscopic drilling of the intact lesion. As a result, patients must undergo administration of general anesthesia during surgery. Post-operatively, patients must have movement of their knees restricted by an immobilizing brace and cannot walk without the use of crutches until healing is evidenced.

In this study, less invasive techniques for treatment of OD are conducted. The techniques involve the use of improved osteogenic device, which is delivered to the defect site via injection. The activity of improved osteogenic device in repair of OD is compared to that of standard osteogenic device.

It is anticipated that patients treated with the improved osteogenic device containing any of the aforementioned matrices and binding agents will show greater relief of symptoms of OD than those treated with standard osteogenic device. Patients treated with improved osteogenic device will experience at least a greater decrease in pain, swelling and locking of the knee than those treated with standard osteogenic device, all of which are indicia of amelioration and/or repair of the defect.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for inducing local bone or cartilage formation, comprising:
   an osteogenic protein selected from the group consisting of OP-1, OP-2, OP-3, BMP3, BMP4, BMP5, BMP6, BMP9, BMP10, BMP11, BMP12, BMP15, BMP16, DPP, Vgl, Vgr, 60A protein, GDF1, GDF3, GDF5, GDF6, GDF7, GDF8, GDF9, GDF10, and GDF11;
   a matrix selected from the group consisting of collagen, demineralized bone, apatites, hydroxyapatites, tricalcium phosphates, and admixtures thereof; and
   a low viscosity grade of an alkylcellulose; wherein when the alkylcellulose is carboxymethylcellulose, said carboxymethylcellulose has a viscosity of 10-200 cP at a concentration of 4% (w/v); and
   wherein the ratio of the alkylcellulose to the matrix in said device is 1 part by weight alkylcellulose to 2-10 parts by weight matrix.

2. The device of claim 1, wherein said osteogenic protein is selected from the group consisting of: OP-1, OP-2, BMP2, BMP4, BMP5, and BMP6.

3. The device of claim 1, wherein said osteogenic protein is OP-1.

4. The device of claim 1, wherein said device comprises at least two different osteogenic proteins.

5. The device of claim 1, wherein said matrix is collagen.

6. The device of claim 1, wherein said device comprises at least two different matrix materials.

7. The device of claim 1, wherein said alkylcellulose is selected from the group consisting of methylcellulose, methylhydroxyethylcellulose, hydroxyethylcellulose, hydroxypropylmethylcellulose, carboxymethylcellulose, sodium carboxymethylcellulose, hydroxyalkylcelluloses, and admixtures thereof.

8. The device of claim 1, wherein said alkylcellulose is carboxymethylcellulose or a sodium salt thereof.

9. The device of claim 1, wherein said device comprises at least two different alkylcelluloses.

10. The device of claim 1, further comprising a wetting agent.

11. The device of claim 10, wherein said wetting agent is saline.

12. The device of claim 1, wherein the ratio of the alkylcellulose to the matrix in said device is 1 part by weight alkylcellulose to 5parts by weight matrix.

13. A method for inducing local bone or cartilage formation, comprising the step of:
providing the device of claim 1 to a defect site.

14. The method of claim 13, wherein said bone formation is endochondral bone formation.

15. The method of claim 13, wherein said cartilage formation is articular cartilage formation.

16. The method of claim 13, wherein said defect site is selected from the group consisting of: critical size defect, non-critical size defect, segmental non-union defect, non-union fracture, fracture, osteochondral defect, and subchondral defect.

17. The method of claim 13, wherein the volume of said device provided to the defect site is sufficient to fill the defect site.

18. A kit for inducing local bone or cartilage formation using the device of claim 1, the kit comprising:
(a) a first receptacle adapted to house said osteogenic protein and said matrix; and
(b) a second receptacle adapted to house said alkylcellulose,
wherein the osteogenic protein and matrix are provided in the first receptacle of part (a), and the alkylcellulose is provided in the second receptacle of part (b).

19. The kit of claim 18, further comprising a third receptacle adapted to house a wetting agent.

20. A kit for inducing local bone or cartilage formation using the device of claim 1, the kit comprising a receptacle adapted to house said osteogenic protein, said matrix material, and said alkylcellulose.

21. The kit of claim 20, further comprising a second receptacle adapted to house a wetting agent.

22. The device of claim 8, wherein said carboxymethylcellulose or said sodium salt thereof has a degree of substitution range from 0.65 to 0.90.

23. The device of claim 5, wherein the amount of the OP-1 ranges from approximately 0.125 mg to 10.0 mg.

24. The device of claim 5, wherein the amount of the OP-1 is approximately 3.5 mg.

25. The method of claim 13, wherein the defect site is endochondral bone, osteochondral bone, or intramembraneous bone.

26. The method of claim 13, wherein the defect site is articular cartilage, fibrocartilage or elastic cartilage.

* * * * *